(12) United States Patent
Lin et al.

(10) Patent No.: US 10,058,276 B2
(45) Date of Patent: Aug. 28, 2018

(54) MEMS AFFINITY SENSOR FOR CONTINUOUS MONITORING OF ANALYTES

(71) Applicant: THE TRUSTEES OF COLUMBIA UNIVERSITY IN THE CITY OF NEW YORK, New York, NY (US)

(72) Inventors: Qiao Lin, New York, NY (US); Xian Huang, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 313 days.

(21) Appl. No.: 15/153,813

(22) Filed: May 13, 2016

(65) Prior Publication Data
US 2016/0249837 A1    Sep. 1, 2016

Related U.S. Application Data

(60) Division of application No. 14/160,092, filed on Jan. 21, 2014, now Pat. No. 9,364,174, which is a
(Continued)

(51) Int. Cl.
*G01N 33/50*  (2006.01)
*A61B 5/1473*  (2006.01)
(Continued)

(52) U.S. Cl.
CPC .......... *A61B 5/1473* (2013.01); *A61B 5/0015* (2013.01); *A61B 5/14532* (2013.01);
(Continued)

(58) Field of Classification Search
None
See application file for complete search history.

(56) References Cited

U.S. PATENT DOCUMENTS 4,979,509 A    12/1990    Hakky
5,508,164 A    4/1996    Kausch et al.
(Continued)

FOREIGN PATENT DOCUMENTS

EP    1 903 338 A2    3/2008
EP    2 138 587 A1    12/2009
(Continued)

OTHER PUBLICATIONS

U.S. Appl. No. 14/221,596, Nov. 14, 2017 Final Office Action.
(Continued)

*Primary Examiner* — Erik B Crawford
(74) *Attorney, Agent, or Firm* — Baker Botts L.L.P.

(57) ABSTRACT

Techniques for monitoring a target analyte in a sample using a polymer capable of binding to the target analyte are disclosed. An implantable monitor useful for the disclosed techniques includes a microdevice coupled with a wireless interface. The wireless interface can comprise a capacitance digital converter coupled with the microdevice and can be adapted to produce a digital signal representing a measurement of the target analyte. A microcontroller can be coupled with the capacitance digital converter and a transponder can be coupled with the microcontroller to transmit the digital signal received from the capacitance digital converter to an external reader.

5 Claims, 28 Drawing Sheets

Related U.S. Application Data continuation of application No. PCT/US2012/048819, filed on Jul. 30, 2012.

(60) Provisional application No. 61/513,335, filed on Jul. 29, 2011, provisional application No. 61/538,732, filed on Sep. 23, 2011, provisional application No. 61/542,113, filed on Sep. 30, 2011, provisional application No. 61/542,139, filed on Sep. 30, 2011.

(51) Int. Cl.
| | |
|---|---|
| *G01N 27/327* | (2006.01) |
| *G01N 33/543* | (2006.01) |
| *B01L 3/00* | (2006.01) |
| *A61B 5/00* | (2006.01) |
| *A61B 5/145* | (2006.01) |
| *G01N 33/66* | (2006.01) |
| *G01N 27/22* | (2006.01) |

(52) U.S. Cl.
CPC ...... *B01L 3/502753* (2013.01); *G01N 27/327* (2013.01); *G01N 33/5438* (2013.01); *G01N 33/66* (2013.01); *A61B 2562/028* (2013.01); *B01L 2200/10* (2013.01); *B01L 2200/147* (2013.01); *B01L 2200/148* (2013.01); *B01L 2300/023* (2013.01); *B01L 2300/0645* (2013.01); *B01L 2300/0663* (2013.01); *B01L 2300/0874* (2013.01); *B01L 2300/1822* (2013.01); *B01L 2400/043* (2013.01); *B01L 2400/0433* (2013.01); *G01N 27/226* (2013.01)

(56) References Cited

U.S. PATENT DOCUMENTS

| | | | |
|---|---|---|---|
| 5,649,947 | A | 7/1997 | Auerbach et al. |
| 5,968,820 | A | 10/1999 | Zborowski et al. |
| 5,998,588 | A | 12/1999 | Hoffman et al. |
| 6,016,686 | A | 1/2000 | Thundat |
| 6,132,580 | A | 10/2000 | Mathies et al. |
| 6,210,326 | B1 | 4/2001 | Ehwald |
| 6,221,677 | B1 | 4/2001 | Wu et al. |
| 6,344,326 | B1 | 2/2002 | Nelson et al. |
| 6,395,165 | B2 | 5/2002 | Bulan et al. |
| 6,397,661 | B1 | 6/2002 | Grimes et al. |
| 6,432,290 | B1 | 8/2002 | Harrison et al. |
| 6,479,242 | B1 | 11/2002 | Gou et al. |
| 6,514,718 | B2 | 2/2003 | Heller et al. |
| 6,641,783 | B1 | 11/2003 | Pidgeon et al. |
| 6,837,896 | B2 | 1/2005 | Matsutani et al. |
| 6,887,693 | B2 | 5/2005 | McMillan et al. |
| 6,933,114 | B2 | 8/2005 | Lupold et al. |
| 7,029,852 | B2 | 4/2006 | Liebholz et al. |
| 7,074,637 | B2 | 7/2006 | Lutz et al. |
| 7,141,375 | B2 | 11/2006 | Pietras et al. |
| 7,151,167 | B2 | 12/2006 | Gjerde et al. |
| 7,217,542 | B2 | 5/2007 | Tyvoll et al. |
| 7,256,695 | B2 | 8/2007 | Hamel et al. |
| 7,285,412 | B2 | 10/2007 | Casagrande et al. |
| 7,287,415 | B2 | 10/2007 | Borwick, III et al. |
| 7,338,762 | B2 | 3/2008 | Gorenstein et al. |
| 7,413,712 | B2 | 8/2008 | Liu et al. |
| 7,499,738 | B2 | 3/2009 | Gerber et al. |
| 7,704,704 | B2 | 4/2010 | Ibey et al. |
| 7,741,123 | B2 | 6/2010 | Pease et al. |
| 7,887,753 | B2 | 2/2011 | Quake et al. |
| 7,896,809 | B2 | 3/2011 | Simpson et al. |
| 7,932,034 | B2 | 4/2011 | Esfandyarpour et al. |
| 7,964,356 | B2 | 6/2011 | Zichi et al. |
| 8,003,397 | B2 | 8/2011 | Wang et al. |
| 8,124,015 | B2 | 2/2012 | Diercks et al. |
| 9,250,169 | B2 | 2/2016 | Ju |
| 2002/0039783 | A1 | 4/2002 | McMillan et al. |
| 2002/0099375 | A1 | 7/2002 | Hess et al. |
| 2002/0117517 | A1 | 8/2002 | Unger et al. |
| 2003/0022370 | A1 | 1/2003 | Casagrande et al. |
| 2003/0233827 | A1 | 12/2003 | Kuo et al. |
| 2004/0005582 | A1 | 1/2004 | Shipwash |
| 2004/0043509 | A1 | 3/2004 | Stahler et al. |
| 2004/0073100 | A1 | 4/2004 | Ballerstadt et al. |
| 2004/0126890 | A1 | 7/2004 | Gjerde et al. |
| 2004/0241718 | A1 | 12/2004 | McGown |
| 2005/0029236 | A1 | 2/2005 | Gambino et al. |
| 2005/0069910 | A1 | 3/2005 | Turner et al. |
| 2005/0142582 | A1 | 6/2005 | Doyle et al. |
| 2005/0161669 | A1 | 7/2005 | Jovanovich et al. |
| 2005/0208487 | A1 | 9/2005 | Burmeister et al. |
| 2005/0250117 | A1 | 11/2005 | Su et al. |
| 2005/0262943 | A1 | 12/2005 | Claydon et al. |
| 2006/0172429 | A1 | 8/2006 | Nilsson et al. |
| 2006/0205061 | A1 | 9/2006 | Roukes et al. |
| 2006/0207891 | A1 | 9/2006 | Althaus et al. |
| 2007/0122811 | A1 | 5/2007 | Buzby |
| 2007/0132043 | A1 | 6/2007 | Bradley et al. |
| 2007/0184456 | A1 | 8/2007 | Chee et al. |
| 2007/0202525 | A1 | 8/2007 | Quake et al. |
| 2007/0248958 | A1 | 10/2007 | Jovanovich et al. |
| 2007/0266801 | A1 | 11/2007 | Khademhosseini et al. |
| 2007/0292397 | A1 | 12/2007 | McNulty et al. |
| 2008/0004905 | A1 | 1/2008 | Jung et al. |
| 2008/0014576 | A1 | 1/2008 | Jovanovich et al. |
| 2008/0056946 | A1 | 3/2008 | Ahmad |
| 2008/0132188 | A1 | 6/2008 | Nivio et al. |
| 2008/0182759 | A1 | 7/2008 | West et al. |
| 2008/0245971 | A1 | 10/2008 | Wimberger-Friedl et al. |
| 2008/0264842 | A1 | 10/2008 | Hukari et al. |
| 2009/0011451 | A1 | 1/2009 | Rodriguez et al. |
| 2009/0047297 | A1 | 2/2009 | Kim et al. |
| 2009/0048124 | A1 | 2/2009 | Leamon et al. |
| 2009/0093013 | A1 | 4/2009 | Fang et al. |
| 2009/0117549 | A1 | 5/2009 | Tan et al. |
| 2009/0166196 | A1 | 7/2009 | Kayyem |
| 2009/0191642 | A1 | 7/2009 | Wang et al. |
| 2009/0227044 | A1 | 9/2009 | Dosev et al. |
| 2009/0253181 | A1 | 10/2009 | Vangbo et al. |
| 2010/0151465 | A1 | 6/2010 | Ju et al. |
| 2010/0203529 | A1 | 8/2010 | Kuslich et al. |
| 2010/0255471 | A1 | 10/2010 | Clarke et al. |
| 2010/0279283 | A1 | 11/2010 | Raghunath et al. |
| 2010/0297733 | A1 | 11/2010 | Lin et al. |
| 2010/0300978 | A1 | 12/2010 | Ramadan et al. |
| 2011/0143949 | A1 | 6/2011 | Heid et al. |
| 2012/0028811 | A1 | 2/2012 | Craighead et al. |
| 2012/0043203 | A1 | 2/2012 | Lin et al. |
| 2012/0100521 | A1 | 4/2012 | Soper et al. |
| 2012/0142088 | A1 | 6/2012 | Hsiao et al. |
| 2012/0263733 | A1 | 10/2012 | Lillard, Jr. |
| 2012/0264155 | A1 | 10/2012 | Frandsen et al. |
| 2013/0035630 | A1 | 2/2013 | Chen |
| 2013/0164755 | A1 | 6/2013 | Weng et al. |
| 2013/0274113 | A1 | 10/2013 | Kim et al. |
| 2014/0038301 | A1 | 2/2014 | Ju et al. |
| 2014/0248621 | A1 | 9/2014 | Collins |
| 2017/0067091 | A1 | 3/2017 | Lin et al. |

FOREIGN PATENT DOCUMENTS

| | | |
|---|---|---|
| KR | 10-2009-0032457 | 4/2009 |
| WO | WO 2005/021725 A2 | 3/2005 |
| WO | WO 2006/021410 A1 | 3/2006 |
| WO | WO 2007/092713 A2 | 8/2007 |
| WO | WO 2007/111639 A1 | 10/2007 |
| WO | WO 2008/042481 A2 | 4/2008 |
| WO | WO 2008/092213 A1 | 8/2008 |
| WO | WO 2009/038536 A1 | 3/2009 |
| WO | WO 2009/140326 A2 | 11/2009 |
| WO | WO 2010/073020 A1 | 7/2010 |
| WO | WO 2010/091400 A2 | 8/2010 |
| WO | WO 2010/123521 | 10/2010 |
| WO | WO 2010/141921 A1 | 12/2010 |
| WO | WO 2012/162779 A1 | 12/2012 |
| WO | WO 2013/044217 A1 | 3/2013 |
| WO | WO 2013/044240 A1 | 3/2013 |

(56) References Cited

FOREIGN PATENT DOCUMENTS

| WO | WO 2014/018688 | | 1/2014 |
|----|----------------|----|--------|
| WO | WO 2014/078521 | A1 | 5/2014 |
| WO | WO 2014/086956 | A2 | 6/2014 |

OTHER PUBLICATIONS

U.S. Appl. No. 14/743,303, Nov. 24, 2017 Final Office Action.
U.S. Appl. No. 15/269,494, Jan. 22, 2018 Non-Final Office Action.
U.S. Appl. No. 15/414,376, Jan. 2, 2018 Response to Restriction Requirement.
U.S. Appl. No. 15/414,376, Nov. 2, 2017 Restriction Requirement.
Inokuchi, et al., "Micro Magnetic Separator for Stem Cell Sorting System," Proceedings of the 22nd Sensor Symposium, Oct. 20-21, 2005, Tokyo, pp. 125-128.
Weng et al "An automatic microfluidic system for rapid screening of cancer stem-like cell-specific aptamers," Microfluid Nanofluid 14:753-765 (2013).
U.S. Appl. No. 14/221,596, Apr. 21, 2017 Non-Final Office Action.
U.S. Appl. No. 14/221,596, Mar. 30, 2017 Amendment and Request for Continued Examination (RCE).
U.S. Appl. No. 14/221,596, Jan. 30, 2017 Notice of Appeal Filed.
U.S. Appl. No. 14/221,596, Jan. 18, 2017 Applicant Initiated Interview Summary.
U.S. Appl. No. 14/743,303, Apr. 12, 2017 Non-Final Office Action.
U.S. Appl. No. 14/743,303, Mar. 1, 2017 Response to Restriction Requirement.
U.S. Appl. No. 14/223,767, Mar. 10, 2017 Non-Final Office Action.
U.S. Appl. No. 14/223,767, Feb. 15, 2017 Amendment and Request for Continued Examination (RCE).
U.S. Appl. No. 12/568,651 (Abandoned), filed Sep. 28, 2009.
U.S. Appl. No. 12/764,898 (U.S. Pat. No. 9,090,663), filed Apr. 21, 2010 (Jul. 28, 2015).
U.S. Appl. No. 13/652,214 (U.S. Pat. No. 9,250,169), filed Oct. 15, 2012 (Feb. 2, 2016).
U.S. Appl. No. 14/221,596 (US 2014/0295424), filed Mar. 21, 2014 (Oct. 2, 2014).
U.S. Appl. No. 14/223,767 (US 2014/0296095), filed Mar. 24, 2014 (Oct. 2, 2014).
U.S. Appl. No. 14/743,303 (US 2016/0146797), filed Jun. 18, 2015 (May 26, 2016).
U.S. Appl. No. 14/978,716 (US 2016/0169780), filed Dec. 22, 2015 (Jun. 16, 2016).
U.S. Appl. No. 15/269,494, filed Sep. 19, 2016.
U.S. Appl. No. 12/568,651, Dec. 31, 2012 Notice of Abandonment.
U.S. Appl. No. 12/568,651, Apr. 13, 2012 Final Office Action.
U.S. Appl. No. 12/568,651, Mar. 12, 2012 Response to Non-Final Office Action.
U.S. Appl. No. 12/568,651, Sep. 12, 2011 Non-Final Office Action.
U.S. Appl. No. 12/568,651, Aug. 1, 2011 Response to Restriction Requirement.
U.S. Appl. No. 12/568,651, May 5, 2011 Restriction Requirement Filed.
U.S. Appl. No. 12/764,898, Jul. 21, 2014 Non-Final Office Action.
U.S. Appl. No. 12/764,898, Jul. 23, 2015 Applicant Initiated Interview Summary.
U.S. Appl. No. 12/764,898, Jun. 23, 2015 Issue Fee Payment.
U.S. Appl. No. 12/764,898, Mar. 26, 2015 Notice of Allowance.
U.S. Appl. No. 12/764,898, Jan. 23, 2015 Applicant Initiated Interview Summary.
U.S. Appl. No. 12/764,898, Jan. 21, 2015 Response to Non-Final Office Action.
U.S. Appl. No. 12/764,898, Apr. 29, 2013 Amendment and Request for Continued Examination (RCE).
U.S. Appl. No. 12/764,898, Nov. 28, 2012 Final Office Action.
U.S. Appl. No. 12/764,898, Sep. 5, 2012 Response to Non-Final Office Action.
U.S. Appl. No. 12/764,898, Jun. 5, 2012 Non-Final Office Action.
U.S. Appl. No. 12/764,898, Apr. 25, 2012 Response to Restriction Requirement.
U.S. Appl. No. 12/764,898, Jan. 26, 2012 Restriction Requirement Filed.
U.S. Appl. No. 13/652,214, Dec. 17, 2015 Issue Fee Payment.
U.S. Appl. No. 13/652,214, Sep. 18, 2015 Notice of Allowance.
U.S. Appl. No. 13/652,214, Jun. 22, 2015 Amendment and Request for Continued Examination (RCE).
U.S. Appl. No. 13/652,214, Jun. 16, 2015 Applicant Initiated Interview Summary.
U.S. Appl. No. 13/652,214, Dec. 22, 2014 Final Office Action.
U.S. Appl. No. 13/652,214, Nov. 24, 2014 Response to Non-Final Office Action.
U.S. Appl. No. 13/652,214, May 28, 2014 Non-Final Office Action.
U.S. Appl. No. 13/652,214, Apr. 7, 2014 Response to Restriction Requirement.
U.S. Appl. No. 13/652,214, Feb. 6, 2014 Restriction Requirement Filed.
U.S. Appl. No. 14/221,596, Jul. 29, 2016 Final Office Action.
U.S. Appl. No. 14/221,596, May 6, 2016 Response to Non-Final Office Action.
U.S. Appl. No. 14/221,596, Jan. 22, 2016 Non-Final Office Action.
U.S. Appl. No. 14/221,596, Jan. 4, 2016 Response to Restriction Requirement.
U.S. Appl. No. 14/221,596, Aug. 17, 2015 Restriction Requirement Filed.
U.S. Appl. No. 14/223,767, Aug. 17, 2016 Final Office Action.
U.S. Appl. No. 14/223,767, May 6, 2016 Response to Non-Final Office Action.
U.S. Appl. No. 14/223,767, Jan. 13, 2016 Applicant Initiated Interview Summary.
U.S. Appl. No. 14/223,767, Sep. 11, 2015 Non-Final Office Action.
U.S. Appl. No. 14/743,303, Sep. 2, 2016 Restriction Requirement Filed.
AAAT Bioquest, "Classic reactive flourescent labeling dyes & their applications," AAT Bioquest, Inc. Product Technical Information Sheet, 2010 [online]. Retrieved on Jan. 29, 2013 at http://www.biomol.de.details/AB/Classic_Reactive_Flourescent_Labeling_Dyes.pdf>.
Adams et al., "Multitarget Magnetic Activated Cell Sorter," Proceedings of the National Academy of Sciences of the United States of America 105:18165-18170 (2008).
Ahn et al., "A sol-gel-based microfluidics system enhances the efficiency of RNA aptamer selection," Oligonucleotides 21(2):93-100 (2011).
Berger et al., "Design of a Microfabricated Magnetic Cell Separator," Electrophoresis 22:3883-3892 (2001).
Blazej et al., "Microfabricated bioprocessor for integrated nanoliter-scale Sanger DNA sequencing," PNAS 103(19):7240-7245 (2006).
Bock et al., "Selection of single-stranded-DNA molecules that bind and inhibit human thrombin," Nature 355:564-566 (1992).
Brody et al., "The use of aptamers in large arrays for molecular diagnostics," Molecular Diagnosis 4(4):381-388 (1999).
Broyles et al., "Sample filtration, concentration, and separation integrated on microfluidic devices," Anal. Chemistry 75:2761-2767 (2003).
Bruno, "Predicting the Uncertain Future of Aptamer-Based Diagnostics and Therapeutics," Molecules 20:6866-6887 (2015).
Burgstaller et al., "Aptamers as tools for target prioritization and lead identification," Drug Discovery Today 7(24):1221-1228 (2002).
Chang et al., "Electrokinetic Mixing in Microfluidic Systems," Microfluidics and Nanofluidics 3:501-525 (2007).
Chen et al., "An automatic microfluidic system that continuously performs the systematic evolution of ligands by exponential enrichment," Microfluidics and Nanofluidics 13(6):929-939 (2012).
Chen et al., "Total nucleic acid analysis integrated on microfluidic devices," Lab on a Chip 7(11):1413-1423 (2007).
Cho et al., "PDMS-glass serpentine microchannel chip for time domain PCR with bubble suppression in sample injection," Journal of Micromechanics and Microengineering 17(9):1810-1817 (2007).
Chou et al., "A microfabricated device for sizing and sorting DNA molecules," PNAS 96(1):11-13 (1999).

(56) References Cited

OTHER PUBLICATIONS

Collett et al., "Functional RNA microarrays for high-throughput screening of antiprotein aptamers," Analytical Biochemistry 338(1):113-123 (2005).
Cox et al., "Automated selection of anti-protein aptamers," Bioorganic & Medicinal Chemistry 9(10):2525-2531 (2001).
D'Orazio et al., "Biosensors in clinical chemistry," Clinica Chimica Acta 334:41-69 (2003).
Dahlin et al., "Poly(dimethylsiloxane)-based microchip for two-dimensional solid-phase extraction-capillary electrophoresis with an integrated electrospray emitter tip," Analytical Chemistry 77(16):5356-5363 (2005).
Darby, R., Chemical Engineering Fluid Mechanics, 2nd Edition, Revised and Expanded, (Marcel Dekker, New York, 2001) (Table of Contents).
Deng et al., "Aptamer affinity chromatography for rapid assay of adenosine in microdialysis samples collected in vivo," Journal of Chromatography A 1005(1-2):123-130 (2003).
Diehl et al., "BEAMing: single-molecule PCR on microparticles in water-in-oil emulsions," Nature Methods 3(7):551-559 (2006).
Dittmer et al., "A DNA-based machine that can cyclically bind and release thrombin," Angewandte Chemie-International Edition 43(27):3550-3553 (2004).
Doherty et al., "Sparsely cross-linked "nanogel" matrixes as fluid, mechanically stabilized polymer networks for high-throughput microchannel DNA sequencing," Anal. Chem. 76:5249-5256 (2004).
Drabovich et al., "Selection of smart aptamers by equilibrium capillary electrophoresis of equilibrium mixtures (ECEEM)," Journal of the American Chemical Society 127(32):11224-11225 (2005).
Drabovich et al., "Selection of smart aptamers by methods of kinetic capillary electrophoresis," Anal. Chem. 78(9):3171-3178 (2006).
Dua et al., "Patents on SELEX and Therapeutic Aptamers," Recent Patents on DNA & Gene Sequences 2:172-186 (2008).
Earhart et al., "Microfabricated magnetic sifter for high-throughput and high-gradient magnetic separation," Journal of Magnetism and Magnetic Materials 321:1436-1439 (2009).
El-Ali et al., "Cell stimulus and lysis in a microfluidic device with segmented gas-liquid flow," Analytical Chemistry 77(11):3629-3636 (2005).
Espy et al., "An Instrument for Sorting of Magnetic Microparticles in a Magnetic Field Gradient," Cytometry Part A, 69A:1132-1142 (2006).
Estes et al., "On Chip Cell Separator Using Magnetic Bead-Based Enrichment and Depletion of Various Surface Markers," Biomedical Microdevices 11:509-515 (2009).
Farokhzad et al., "Targeted nanoparticle-aptamer bioconjugates for cancer chemotherapy in vivo," PNAS 103(16):6315-6320 (2006).
Fivash et al., "BIAcore for macromolecular interaction," Current Opinion on Biotechnology 9(1):97-101 (1998).
Furdui et al., "Immunomagnetic T cell capture from blood for per analysis using microfluidic systems," Lab on a Chip 4:614-618 (2004).
Geiger et al., "RNA aptamers that bind L-arginine with sub-micromolar dissociation constants and high enantioselectivity," Nucleic Acids Research 24(6):1029-1036 (1996).
Giordano et al., "Towards dynamic coating of glass microchip chambers for amplifying DNA via the polymerase chain reaction," Electrophoresis 22(2):334-340 (2001).
Gopinath, "Methods developed for SELEX," Analytical and Bioanalytical Chemistry 387(1):171-182 (2007).
Green et al., "Aptamers as reagents for high-throughput screening," BioTechniques 30(5):1094-1110 (2001).
Hamula et al., "Selection and analytical applications of aptamers," Trends Anal. Chem. 25(7):681-691 (2006).
Handbook of Affinity Chromatography, 2 Edition. Edited by David S. Hage, Taylor and Francis, (Table of Contents) (2006).

Herr et al., "Aptamer-conjugated nanoparticles for selective collection and detection of cancer cells," Analytical Chemistry 78(9):2918-2924 (2006).
Hessel et al., "Micromixers—a Review on Passive and Active Mixing Principles," Chemical Engineering Science 60:2479-2501 (2005).
Hoffman et al., "Immobilized DNA aptamers used as potent attractors for porcine endothelial precursor cells," Journal of Biomedical Materials Research Part A, 84A(3):614-621 (2008).
Hsing et al., "Micro- and nano-magnetic particles for applications in biosensing," Electroanalysis 10(7-8):755-768 (2007).
Huang et al., "Integrated microfluidic system for rapid screening of CRP aptamers utilizing systematic evolution of ligands by exponential enrichment (SELEX)," Biosensors and Bioelectronics 25:1761-1766 (2010).
Hybarger et al., "A microfluic SELEX prototype," Analytical and Bioanalytical Chemistry 384(1):191-198 (2006).
Inglis et al., "Continuous Microfluidic Immunomagnetic Cell Separation," Applied Physics Letters 85(21):5093-5095 (2004).
Inokuchi et al., "Development of micro immuno-magnetic cell sorting system with lamination mixer and magnetic separator," Proc. 25th Sensor Symp., 2008, pp. 1-2.
International Search Report and Written Opinion for PCT/US2012/056888, dated Feb. 25, 2013.
International Search Report and Written Opinion for PCT/US2012/056926, dated Dec. 3, 2012.
International Search Report and Written Opinion for PCT/US2013/070075, dated Feb. 21, 2014.
International Search Report and Written Opinion dated Jun. 22, 2015 in International Application No. PCT/US2015/022044.
International Search Report for PCT/US2008/058433, dated Jun. 30, 2008.
James, W., "Aptamers in the virologists' toolkit," Journal of General Virology 88(8):351-364 (2007).
Jayasena, "Aptamers: An emerging class of molecules that rival antibodies in diagnostics," Clinical Chemistry 45(9):1628-1650 (1999).
Jellinek et al., "Potent 2'-amino-2'-deoxypyrimidine RNA inhibitors of basic fibroblast growth-factor," Biochemistry 34(36):11363-11372 (1995).
Jenison et al., "High-resolution molecular discrimination by RNA," Science 263(5152):1425-1429 (1994).
Jensen et al., "Kinetics for hybridization of peptide nucleic acids (PNA) with DNA and RNA studied with the BIAcore technique," Biochemistry 36(16):5072-5077 (1997).
Kanter et al., "Cell-free production of SCFV fusion proteins: an efficient approach for personalized lymphoma vaccines," Blood 109(8):3393-3399 (2007).
Kim et al., "A microchip for nucleic acid isolation and enrichment," 2012 IEEE 25th International Conference on Micro Electro Mechanical Systems, pp. 765-768 (2012).
Kim et al., "Solid phase capturable dideoxynucleotides for multiplex genotyping using mass spectrometry," Nucleic Acids Research 30(16):e85 (2002).
Kopp et al., "Chemical amplification: Continuous-flow PCR on a chip," Science 280(5366):1046-1048 (1998).
Lai et al., "Aptamer-based electrochemical detection of picomolar platelet-derived growth factor directly in blood serum," Analytical Chemistry 79(1):229-233 (2007).
Lee et al., "A therapeutic aptamer inhibits angiogenesis by specifically targeting the heparin binding domain of VEGF 165," PNAS 102(52):18902-18907 (2005).
Lermo et al., "In-situ DNA amplification with magnetic primers for the electrochemical detection of food pathogens," Biosensors and Bioelectronics 22(9-10):2010-2017 (2007).
Lien et al., "Purification and enrichment of virus samples utilizing magnetic beads on a microfluidic system," Lab on a Chip 7:868-875 (2007).
Lin et al., "Aptamer-Based Microfluidic Biosensors," 9th IEEE Conference on Nanotechnology, pp. 812-814 (2009).
Liu et al., "Passive Mixing in a Three-Dimensional Serpentine Microchannel," Journal of Microelectromechanical Systems 9:190-197 (2000).

(56) References Cited

OTHER PUBLICATIONS

Liu et al., "Micro air bubble formation and its control during polymerase chain reaction (PCR) in polydimethylsiloxane (PDMS) microreactors," Journal of Micromechanics and Microengineering 17:2055-2064 (2007).
Lowe et al., "Multiplex single nucleotide polymorphism genotyping utilizing ligase detection reaction coupled surface enhanced raman spectroscopy," Analytical Chemistry 82(13):5810-5814 (2010).
Lund-Olesen et al., "Capture of DNA in Microfluidic Channel Using Magnetic Beads: Increasing Capture Efficiency with Integrated Microfluidic Mixer," Journal of Magnetism and Magnetic Materials 311:396-400 (2007).
Lupold et al., "Identification and characterization of nuclease-stabilized RNA molecules that bind human prostate cancer cells via the prostate-specific membrane antigen," Cancer Research 62(14):4029-4033 (2002).
Mannironi et al., "In vitro selection of dopamine RNA ligands," Biochemistry 36(32):9726-9734 (1997).
Mendonsa et al., "In-vitro evolution of functional DNA using capillary electrophoresis," Journal of the American Chemical Society 126(1):20-21 (2004).
Miltenyi et al., "High gradient magnetic cell separation with MACS," Cytometry Part A. 11(2):231-238 (1990).
Misra et al., "Microbead device for isolating biotinylated oligonucleotides for use in mass spectrometric analysis," Analytical Biochemistry 384(1):96-100 (2009).
Mosing et al., "Capillary electrophoresis-SELEX selection of aptamers with affinity for HIV-1 reverse transcriptase," Anal. Chem. 77(19):6107-6112 (2005).
Murphy et al., "An improved method for the in vitro evolution of aptamers and applications in protein detection and purification," Nucleic Acids Research 31(18):e110 (2003).
Nguyen et al., "An aptamer-based microfluidic device for thermally controlled affinity extraction," Microfluid Nanofluid 6(4):479-487 (2009).
Nguyen et al., "Micromixers—a Review," Journal of Micromechanics and Microengineering 15:R1-R16 (2005).
Nieuwlandt et al., "In-vitro selection of RNA ligands to substance-P," Biochemistry 34(16):5651-5659 (1995).
Nimjee et al., "The potential of aptamers as anticoagulants," Trends Cardiovascular Medicine 15(1):41-45 (2005).
O'Sullivan et al., "Aptasensors—the future of biosensing," Analytical and Bioanalytical Chemistry 372:44-48 (2002).
Oh et al., "Screening of Molecular Libraries Using the Continuous-Flow, Micro-Magnetic Cell Sorter," 10th International Conference on Miniaturized Systems for Chemistry and Life Sciences, Nov. 5-9, 2006, Tokyo, Japan, pp. 975-977.
Pamme et al., "Continuous sorting of magnetic cells via on-chip free-low magnetophoresis," Lab on a Chip 6(8):974-980 (2006).
Prosek et al., "Aptamers—basic research, drug development, and clinical applications," Appl. Microbiol. Biotechnol. 69:367-374 (2005).
Ramsey et al., "Integrated microfluidic device for solid-phase extraction coupled to micellar electrokinetic chromatography separation," Anal. Chem. 77:6664-6670 (2005).
Ravelet et al., "Liquid chromatography, electrochromatography, and capillary electrophoresis applications of DNA and RNA aptamers," Journal of Chromatography A 1117:1-10 (2006).
Reigstad et al., "Platelet-derived growth factor (PDGF)-C, a PDGF family member with a vascular endothelial growth factor-like structure," The Journal of Biological Chemistry 278(19):17114-17120 (2003).
Reuter et al., "Kinetics of protein-release by an aptamer-based DNA nanodevice," European Physical Journal E. 22(1):33-40 (2007).
Romig et al., "Aptamer affinity chromatography: combinatorial chemistry applied to protein purification," Journal of Chromatography B—Analytical Technologies in the Biomedical and Life Sciences 731(2):275-284 (1999).
Sanchez-Freire et al., "Microfluidic single-cell real-time PCR for comparative analysis of gene expression patterns," Nature Protocols 7:829-838 (Apr. 2012).
Shamah et al., "Complex target SELEX," Accounts of Chemical Research 41(1):130-138 (2008).
Shangguan et al., "Cell-specific aptamer probes for membrane protein elucidation in cancer cells," Journal of Proteome Research 7(5):2133-2139 (2008).
Shao et al., "Emulsion PCR: A high efficient way of PCR amplification of random DNA libraries in aptamer selection," PlosOne 6(9):E24910 (2011).
Sikavitsas et al., "Transport and kinetic processes underlying biomolecular interactions in the BIACORE optical biosensor," Biotechnology Progress 18(4):885-897 (2002).
So et al., "Detection and titer estimation of *Escherichia coli* using aptamer-functionalized single-walled carbon-nanotube field-effect transistors," Small 4(2):197-201 (2008).
Stahlberg et al., "Single-cell gene-expression profiling and its potential diagnostic applications," Exp. Rev. of Mol. Diagnostics 11(7):735-740 (Sep. 2011).
Stroock et al., "Chaotic Mixer for Microchannels," Science 295:647-651 (2002).
Stroock et al., "Controlling flows in microchannels with patterned surface charge and topography," Accounts of Chemical Research 36(8):597-604 (2003).
Supplementary Partial European Search Report dated Aug. 28, 2015 in EP Application No. EP 12834427.
Suzuki et al., "Chaotic mixing of magnetic beads in microcell separator," Proc. 3rd Int. Symp. Turbulence and Shear Flow Phenomena, Jun. 24-27, 2003, pp. 817-822.
Tang et al., "Chip-based genotyping by mass spectrometry," PNAS 96(18):10016-10020 (1999).
Taylor et al., "Dynamics of an anti-VEGF DNA aptamer: A single-molecule study," Biochemical and Biophysical Research Communications 373(2):213-218 (2008).
Temples et al., "On-line coupling of size exclusion chromatography and capillary electrophoresis via solid-phase extraction and a Tee-split interface," Journal of Chromatography B 839:30-35 (2006).
Thorsen et al., "Microfluidic large-scale integration," Science 298 (5593):580-584 (2002).
Tombelli et al., "Analytical applications of aptamers," Biosensors and Bioelectronics 20:2424-2434 (2005).
Toriello et al., "Integrated affinity capture, purification, and capillary electrophoresis microdevice for quantitative double-stranded DNA analysis," Anal. Chem. 79(22):8549-8556 (2007).
Tuerk et al., "Systematic evolution of ligands by exponential enrichment: RNA ligands to bacteriophage T4 DNA polymerase," Science 249:505-510 (1990).
Unger et al., "Monolithic microfabricated valves and pumps by multilayered soft lithography," Science, 288:113-116 (2000).
Verpoorte, "Beads and Chips: New Recipes for Analysis," Lab on a Chip 3:60N-68N (2003).
Viskari et al., "Unconventional detection methods for microfluidic devices," Electrophoresis 27(9):1797-1810 (2006).
Wallis et al., "Vasopressin is a physiological substrate for the insulin-regulated aminopeptidase IRAP," Am. J. Physiol. Endocrinol. Metab. 293(4):E1092-E1102 (2007).
Wang et al., "Demonstration of MEMS-based differential scanning calorimetry for determining thermodynamic properties of biomolecules," Sensors and Actuators B: Chemical 134:953-958 (2008).
Wang et al., "Pre-binding dynamic range and sensitivity enhancement for immuno-sensor using nanofluidic preconcentrator," Lab on a Chip 8:392-394 (2007).
White et al., "High-throughput microfluidic single-cell RT-qPCR," PNAS 108(34):13999-14004 (Aug. 2011).
Williams et al., "Bioactive and nuclease-resistant L-DNA ligand of vasopressin," PNAS 94(21):11285-11290 (1997).
Wu et al., "MEMS flow sensors for nano-fluidic applications," Sensors and Actuators A. 89(1-2):152-158 (2001).
Xia et al., "Chaotic micromixers using two-layer crossing channels to exhibit fast mixing at low Reynolds numbers," Lab on a Chip 5(7):748-755 (2005).

(56) References Cited

OTHER PUBLICATIONS

Xiaoyu et al., "Polydimethylsiloxane (PDMS)-based spiral channel PCR chip," Electronics Letters 46(16):890-891 (2005).
Xu et al., "Review: Aptamers in microfluidic chips," Analytica Chimica Acta 683(1):12-20 (2010).
Xu et al., "Aptamer-Based Microfluidic Device for Enrichment, Sorting, and Detection of Multiple Cancer Cells," Anal. Chem. 81:7436-7442 (2009).
Yang et al., "Advances in SELEX and application of aptamers in the central nervous system," Biomolecular Engineering 24(6):583-592 (2007).
Yang et al., "DNA ligands that bind tightly and selectively to cellobiose," PNAS 95(10):5462-5467 (1998).
Yeung et al., "A DNA biochip for on-the-spot multiplexed pathogen identification," Nucleic Acids Res. 34(18):e118 (2006).
Yu et al., "Preparation of monolithic polymers with controlled porous properties for microfluidic chip applications using photoinitiated free-radical polymerization," Journal of Polymer Science Part A—Polymer Chemistry 40(6):755-169 (2002).
Zhang et al., "Differentiation and detection of PDGF isomers and their receptors by tunable aptamer capillary electrophoresis," Analytical Chemistry 81(18):7795-7800.
Zhang et al., "In-vitro selection of bacteriophage ø 29 prohead RNA aptamers for prohead binding," The Journal of Biological Chemistry 273(5):2947-2953 (1998).
U.S. Appl. No. 13/246,404 (U.S. Pat. No. 9,400,233), filed Sep. 27, 2011 (Jul. 26, 2016).
U.S. Appl. No. 14/160,092 (U.S. Pat. No. 9,364,174), filed Jan. 21, 2014 (Jun. 14, 2016).
U.S. Appl. No. 13/246,404, Jun. 22, 2016 Issue Fee Payment.
U.S. Appl. No. 13/246,404, Mar. 28, 2016 Notice of Allowance.
U.S. Appl. No. 13/246,404, Feb. 25, 2016 Response to Non-Final Office Action.
U.S. Appl. No. 13/246,404, Feb. 11, 2016 Applicant Initiated Interview Summary.
U.S. Appl. No. 13/246,404, Sep. 25, 2015 Non-Final Office Action.
U.S. Appl. No. 13/246,404, Sep. 17, 2015 Response to Restriction Requirement.
U.S. Appl. No. 13/246,404, Mar. 26, 2015 Restriction Requirement Filed.
U.S. Appl. No. 13/246,404, Jun. 27, 2014 Amendment and Request for Continued Examination (RCE).
U.S. Appl. No. 13/246,404, Jan. 30, 2014 Final Office Action.
U.S. Appl. No. 13/246,404, Oct. 18, 2013 Response to Non-Final Office Action.
U.S. Appl. No. 13/246,404, May 23, 2013 Non-Final Office Action.
U.S. Appl. No. 14/160,092, May 13, 2016 Issue Fee Payment.
U.S. Appl. No. 14/160,092, Apr. 12, 2016 Notice of Allowance.
U.S. Appl. No. 14/160,092 Mar. 24, 2016 Amendment and Response to Non-Final Office Action.
U.S. Appl. No. 14/160,092, Feb. 19, 2016 Notice of Allowance.
U.S. Appl. No. 14/160,092, Jan. 15, 2016 Response to Non-Final Office Action.
U.S. Appl. No. 14/160,092, Sep. 3, 2015 Non-Final Office Action.
U.S. Appl. No. 14/160,092, Jun. 30, 2015 Response to Restriction Requirement.
U.S. Appl. No. 14/160,092, Mar. 3, 2015 Restriction Requirement Filed.
Barnes et al., "A Femtojoule Calorimeter Using Micromechanical Sensors," AIP: Review of Scientific Instruments, 65:3793-3798 (Dec. 1994).
Cavicchi et al., "Micro-Differential Scanning Calorimeter for Combustible Gas Sensing," Sensors and Actuators B; Chemical, 97(1):22-30 (Jan. 2004).
Huang et al., "A Biocompatible Affinity MEMS Sensor for Continuous Monitoring of Glucose," IEEE 4th International Nano/Micro Engineered and Molecular Systems, Shenzhen, China, pp. 797-802 (2009).
Huang et al., "A Capacitive MEMS Viscometric Sensor for Affinity Detection of Glucose," Microelectromechanical System, 18(6):1246-1254 (2009).
Huang et al., "A Capacitively Based MEMS Affinity Glucose Sensor," IEEE Solid-State Sensors, Actuators and Microsystems Conference, Denver, Colorado, pp. 1457-1460 (2009).
Huang et al., "A MEMS Differential Affinity Sensor for Continuous Glucose Detection," Solid-State Sensors, Actuators and Microsystems Conference, (abstract only) Jun. 5-9, 2011.
Huang et al., "A MEMS Sensor for Continuous Monitoring of Glucose on Subcutaneous Tissue," IEEE 22nd International Conference on Microelectromechanical Systems (MEMS), Sorrento, Italy, pp. 352-355 (2009).
Huang, et al., "A MEMS Affinity Glucose Sensor Using a Biocompatible Glucose-Responsive Polymer," Sensors and Actuators B: Chemical, 140(2):603-609 (2009).
International Search Report and Written Opinion for PCT/US2009/062891, dated Jan. 13, 2010.
International Search Report and Written Opinion for PCT/US2012/048819, dated Nov. 15, 2012.
Lai et al., "High-speed ($10^4$ ° C./s) Scanning Microcalorimetry with Monolayer Sensitivity ($J/m^2$)," Applied Physics Letters, 67:1229-1231 (Aug. 1995).
Mansouri et al., "A Miniature Optical Glucose Sensor Based on Affinity Binding," Nature Biotechnology, 2:885-890 (1984).
Vanden Poel et al., "Performance and Calibration of the Flash DSC1, a New, MEMS-Based Fast Scanning Calorimeter," Journal of Thermal Analysis and Calorimetry, 110(3):1533-1546 (Dec. 2012).
Wang et al., "A MEMS Isothermal Titration Biocalorimeter," 16th International Conference on Miniaturized Systems for Chemistry and Life Sciences, pp. 195-197 (Oct. 28-Nov. 1, 2012) Okinawa, Japan.
Zhao et al., "A MEMS Viscometric Sensor for Continuous Glucose Monitoring," J. Micromech. Microeng., 17:2528-2537 (2007).
U.S. Appl. No. 15/414,376 (US 2017/0130218), filed Jan. 24, 2017 (May 11, 2017).
International Search Report dated Nov. 10, 2015 in International Application No. PCT/US15/43824.
Kim et al., "Nucleic acid isolation and enrichment on a microchip," Sensors and Actuators A: Physical 195:183-190 (2013).
Kristinsson et al., "Improved long-term survival in multiple myeloma up to the age of 80 years," Leukemia 28:1346-1348 (2014).
Rawstron et al., "Minimal Residual Disease Assessed by Multiparameter Flow Cytometry in Multiple Myeloma: Impact on Outcome in the Medical Research Council Myeloma IX Study," Journal of Clinical Oncology 31:2540-2547 (2013).
Shum et al., "Nucleic Acid Aptamers as Potential Therapeutic and Diagnostic Agents for Lymphoma," Journal of Cancer Therapy 4:872-890 (2013).
Tate et al., "Quantitative Serum Free Light Chain Assay—Analytical Issues," The Clinical Biochemist Reviews 30:131-140 (2009).
Yao et al., "Aptamer-based piezoelectric quartz crystal microbalance biosensor array for the quantification of IgE," Biosensors and Bioelectronics 24:2499-2503 (2009).
U.S. Appl. No. 15/492,656 (US 2017/0283859), filed Apr. 20, 2017 (Oct. 5, 2017) Qiao Lin, et al.
U.S. Appl. No. 14/221,596, Jul. 21, 2017 Response to Non-Final Office Action.
U.S. Appl. No. 14/223,767, Sep. 21, 2017 Notice of Abandonment.
U.S. Appl. No. 14/743,303, Oct. 5, 2017 Response to Non-Final Office Action.
U.S. Appl. No. 14/978,716, Aug. 29, 2017 Final Office Action.
U.S. Appl. No. 15/269,494, Nov. 2, 2017 Response to Restriction Requirement.
U.S. Appl. No. 15/269,494, Sep. 13, 2017 Restriction Requirement.
International Search Report dated Jan. 28, 2016 in International Application No. PCT/US15/57086.
Written Opinion of the International Searching Authority for PCT/US2008/057433 dated Sep. 3, 2008.

MEMS AFFINITY SENSOR FOR CONTINUOUS MONITORING OF ANALYTES

CROSS REFERENCE TO RELATED APPLICATIONS

This application is a divisional of U.S. application Ser. No. 14/160,092, filed Jan. 21, 2014, which is a continuation of International Patent Application No. PCT/US12/048819, filed Jul. 30, 2012, which claims priority from U.S. Provisional Application No. 61/513,335, filed Jul. 29, 2011; U.S. Provisional Application No. 61/538,732, filed Sep. 23, 2011; U.S. Provisional Application No. 61/542,113, filed Sep. 30, 2011; and U.S. Provisional Application No. 61/542,139, filed Sep. 30, 2011. The disclosure of each of the foregoing applications is herein incorporated by reference by its entirety.

STATEMENT REGARDING FEDERALLY SPONSORED RESEARCH

This invention was made with government support under grants DK063068 and 0702101 awarded by the National Institutes of Health, and the National Science Foundation, respectively. The Government has certain rights in this invention.

BACKGROUND

Diabetes mellitus is a metabolic disease characterized by persistent hyperglycemia (high blood sugar levels). Complications induced by diabetes, such as heart disease, stroke, hypertension, blindness, kidney failure, and amputation deprive the lives of 231,404 people in America as recently as 2007, making diabetes the seventh leading cause of death.

Glucose monitoring can reduce the occurrence rate and severity of complications caused by hyperglycemia or hypoglycemia. Thus, it is important to closely monitor abnormal blood sugar levels in diabetes patients so timely treatments (e.g., insulin injection, exercise, and diabetic diet, intake of carbohydrate) can be administered. This can be achieved by continuous glucose monitoring, which involves either noninvasive or minimally invasive detection of glucose. Noninvasive methods can extract interstitial fluid (ISF) glucose from the skin in minimally destructive approaches or measure blood glucose in contactless manners. Although noninvasive methods can be used for CGM, interferences, such as the complexity of skin structures, sweating, temperature, and exercise can impact the accuracy and reliability of the system, limiting their practical applications in CGM. Certain minimally invasive methods can use subcutaneous sensor implantation to monitor the glucose levels in ISF. In the steady state, ISF glucose concentration is identical to that in blood. However, when the blood glucose levels undergo rapid changes, time lags between the blood and the ISF glucose concentrations can occur.

Electrochemical glucose sensors, which use $O_2$ and $H_2O_2$ as the mediators, can also be subject to errors induced by fluctuations of oxygen levels. In addition, redox-active species, such as ascorbic and uric acids, can compromise the selectivity and the accuracy of the glucose sensors. Other devices utilize artificial mediators (e.g., ferro/ferricyanide, hydroquinone, and ferrocene) as alternatives to oxygen for electron transfer. However, competition of oxygen with the artificial mediators and potential leaching and toxicity of these artificial mediators can hinder the in-vivo applications of these devices.

MEMS devices offer miniature sizes and rapid time responses, and are suited for implantable or noninvasive glucose sensors. MEMS technology can be used in developing electrochemical CGM sensors. MEMS affinity glucose sensors can use Con A, boronic-acid based monomers and polymers, and GBP as the glucose receptors and measure the glucose-induced changes in the properties of these receptors. For example, viscosity changes due to the binding of Con A or boronic acid-based polymers with glucose can be exploited by optical or electrical detection of microcantilever vibration, piezoelectric detection of flow resistance, and hall effect detection of microrotors.

There is a need to develop implantable glucose monitoring systems that offer improved long term accuracy and stability, low drift, resistance to environmental parameter fluctuations, easier calibration, as well as the capability of providing real-time report of a subject's glucose level via wireless telemetry.

SUMMARY

The disclosed subject matter provides techniques for monitoring a target analyte in a sample using a polymer capable of binding to the target analyte. In one aspect, an exemplary microdevice includes a semi-permeable membrane structure, a substrate, first and second microchambers formed between the membrane structure and the substrate, and a suspended element positioned to be spaced apart from the substrate. The first microchamber can be adapted to receive a solution including the polymer. The second microchamber can be adapted to receive a reference solution for screening effects not caused by the target analyte. The semi-permeable membrane structure can be permeable to the target analyte and impermeable to the polymer, such that when the sample is placed in contact with the semi-permeable membrane structure, the target analyte, if present in the sample, permeates the semi-permeable membrane structure and enters the first microchamber and the second microchamber, respectively. The polymer can be prevented from escaping from the first microchamber through the semi-permeable membrane structure. The microdevice can further include the polymer solution in the first microchamber and the reference solution in the second microchamber.

In some embodiments of the microdevice, the binding of the polymer with the target analyte causes a change in the permittivity of the polymer solution. In alternative embodiments, the suspended element of each of the first microchamber and the second microchamber includes a vibrational element, and the binding of the polymer with the target analyte causes a change in the viscosity of the polymer solution, which in turn influences the vibration of the vibrational element in the first microchamber. The vibration of the vibrational element can be actuable by an external magnetic field. For example, the vibrational element can include permalloy.

In some embodiments, each of the first microchamber and the second microchamber further include a top electrode and a bottom electrode, respectively. The top electrode can be included in the suspended element, and the bottom electrode can be included in the substrate. In particular embodiments, the top electrode can be supported by at least one post formed from the substrate. In particular embodiments, the top electrode for each of the first microchamber and the second microchamber can also be perforated.

The disclosed subject matter also provides a microdevice for monitoring a target analyte in a sample using a polymer capable of binding to the target analyte. An exemplary microdevice includes a semi-permeable membrane structure; a substrate; a microchamber formed between the semi-permeable membrane structure and the substrate. The microchamber can be adapted to receive a solution including the polymer, and include a suspended element positioned to be spaced apart from the substrate. The suspended element can include a perforated electrode, which can be supported on one or more posts formed from the substrate. The semi-permeable membrane structure can be permeable to the target analyte and impermeable to the polymer, such that when the sample is placed in contact with the semi-permeable membrane structure, the target analyte, if present in the sample, permeates the semi-permeable membrane and enters the microchamber. The polymer can be prevented from escaping from the microchamber through the semi-permeable membrane structure. The microdevice can further include the polymer solution in the microchamber.

In various embodiments of the disclosed microdevices, the polymer reversibly binds with the target analyte. The microdevices can be adapted to be implantable in a subcutaneous tissue of a subject, e.g., a mammal or a human subject. The microdevices can include integrated microheaters and/or temperature sensors, and can be coupled with a wireless interface for transmitting signals representing measurement of the target analyte.

The disclosed subject matter also provides methods of using such microdevices. In one example, a method includes loading a solution including a target-analyte sensitive polymer into a first microchamber, and a reference solution into a second microchamber; placing a sample in contact with a semi-permeable membrane structure such that a target analyte in the sample permeates the semi-permeable membrane structure and enters the first microchamber and the second microchamber, respectively; and determining a presence and/or concentration of the target analyte in the sample.

BRIEF DESCRIPTIONS OF THE DRAWINGS

Figure 1A:
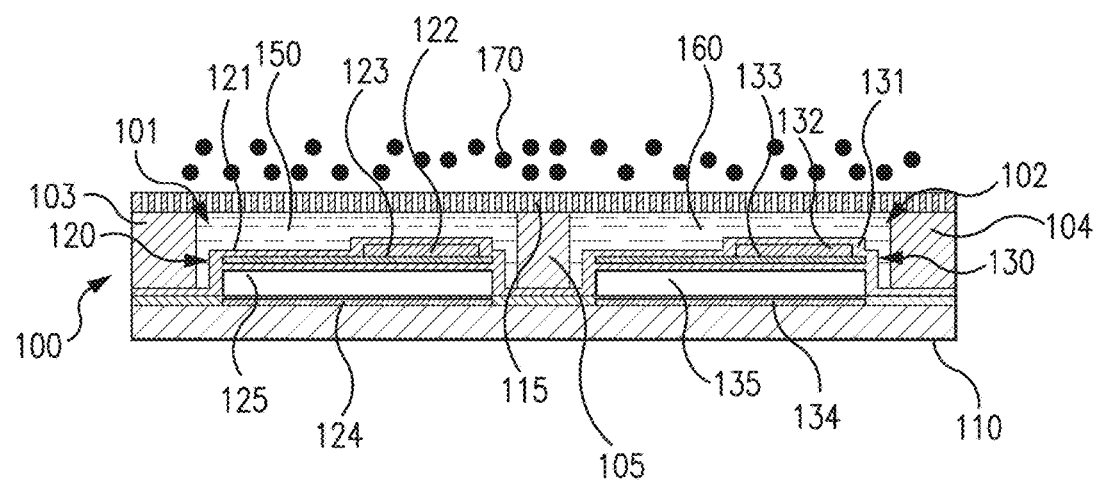
FIGS. 1A and 1B are schematic side views of microdevices according to some embodiments of the disclosed subject matter.

FIGS. 4A-4F are diagrams illustrating a representative fabrication process for the microdevice depicted in FIG. 1A. (A) Bottom electrode deposition. (B) Parylene deposition and sacrificial layer patterning. (C) Parylene deposition. (D) Moving electrode deposition and Permalloy electroplating. (E) Additional parylene layer deposition and aluminum mask deposition. (F) Sacrificial layer removal and diaphragm release.

Figure 5A:
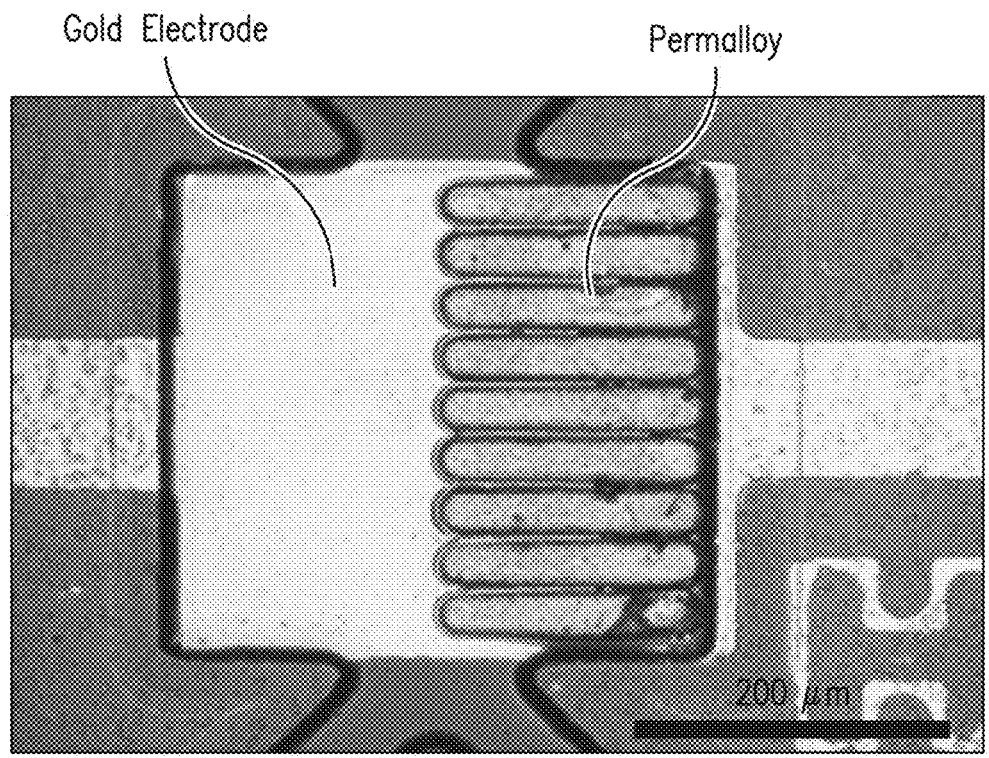
Figure 5B:
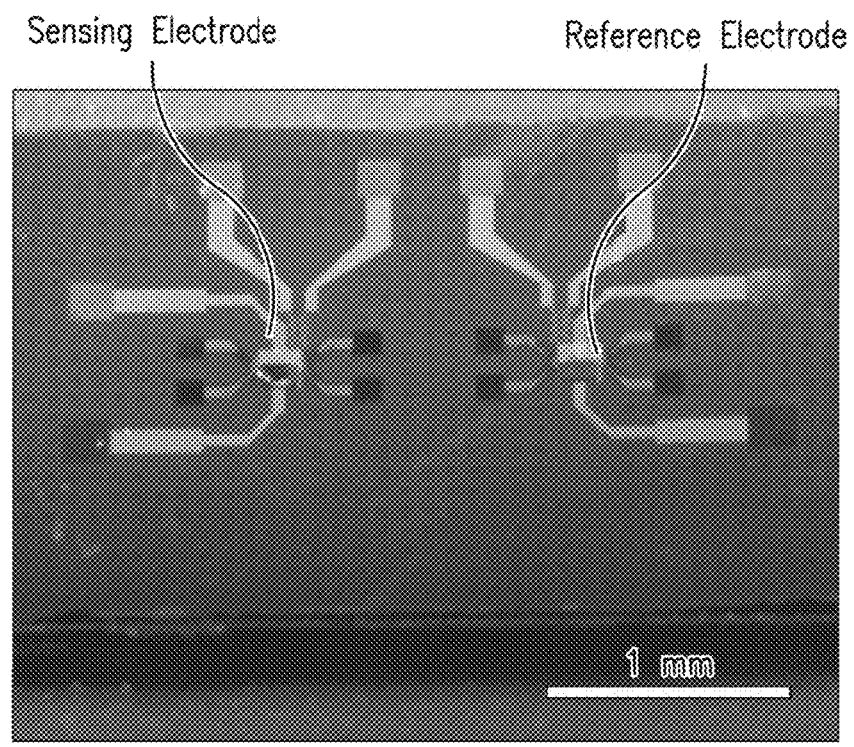

FIGS. 5A-5B are micrographs of (A) a single vibrational diaphragm and (B) a MEMS differential glucose sensor.

Figure 6:
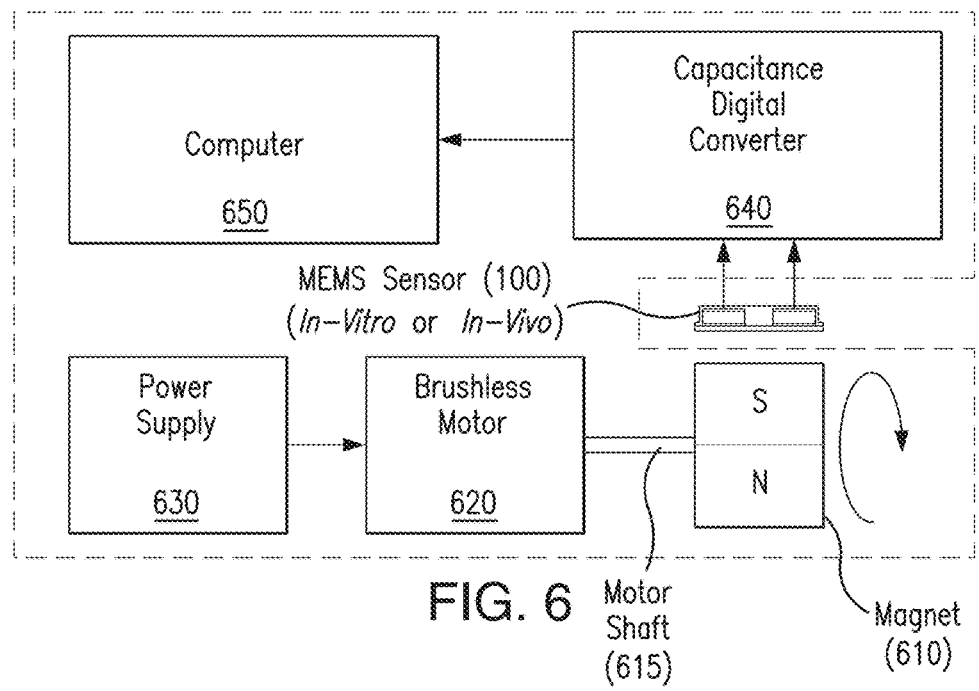

FIG. 6 is an exemplary setup for in-vitro and in-vivo characterization of a MEMS differential glucose sensor.

Figure 7:
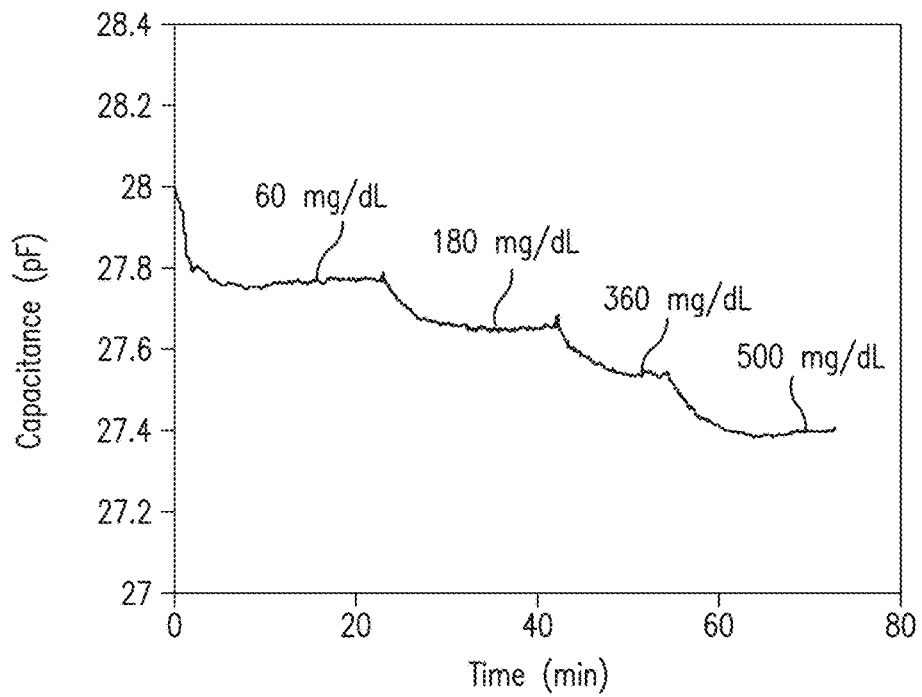

FIG. 7 is a plot illustrating the response of a MEMS differential glucose sensor of the disclosed subject matter to different glucose concentrations.

Figure 8:
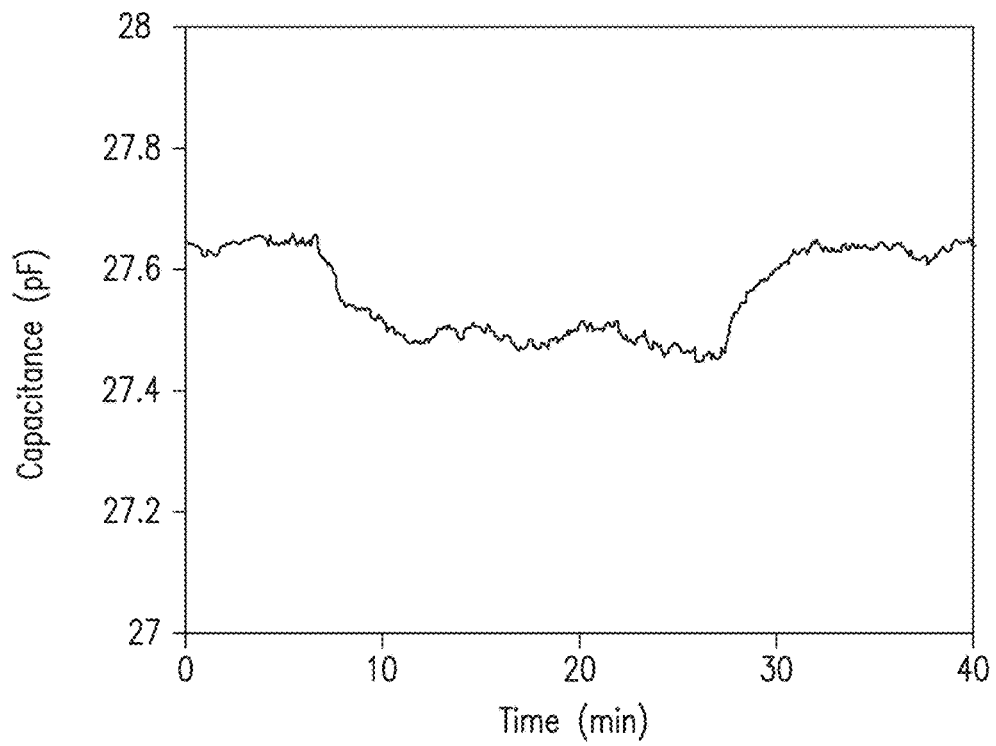

FIG. 8 is a plot illustrating the time-dependent vibration amplitude of a vibrational diaphragm (indicated by the sensor capacitance) of a MEMS differential glucose sensor of the disclosed subject matter as glucose concentration changes from 60 to 90 mg/dL, then back to 60 mg/dL.

Figure 9:
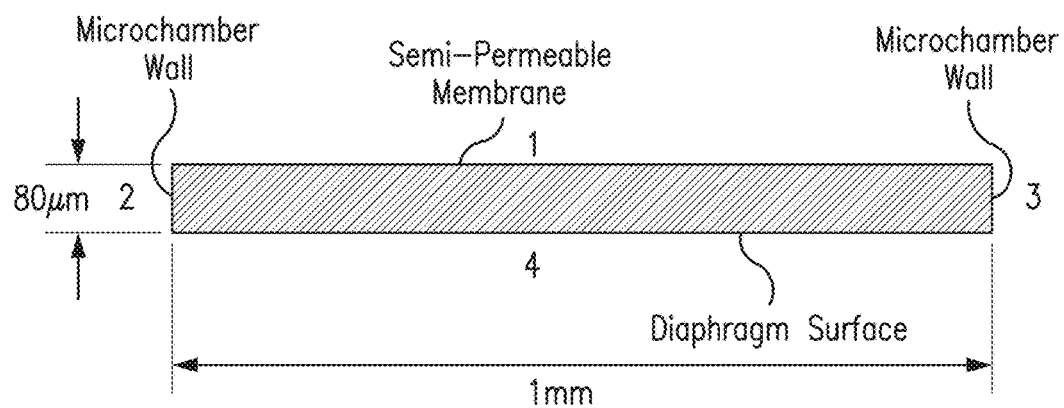

FIG. 9 is a plot depicting a simulation model to characterize the glucose diffusion in a MEMS differential glucose sensor.

Figure 10:
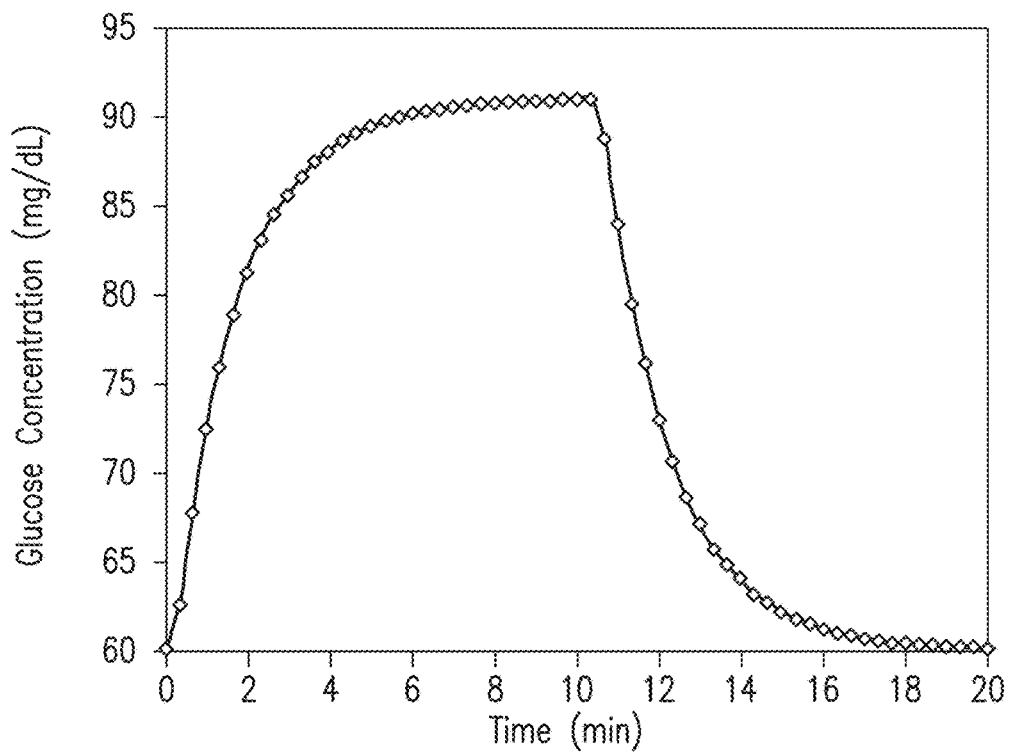

FIG. 10 is a plot showing the simulation result of the time-dependent glucose concentration on the surface of the vibrational diaphragm of glucose sensor as modeled in FIG. 9.

Figure 11:
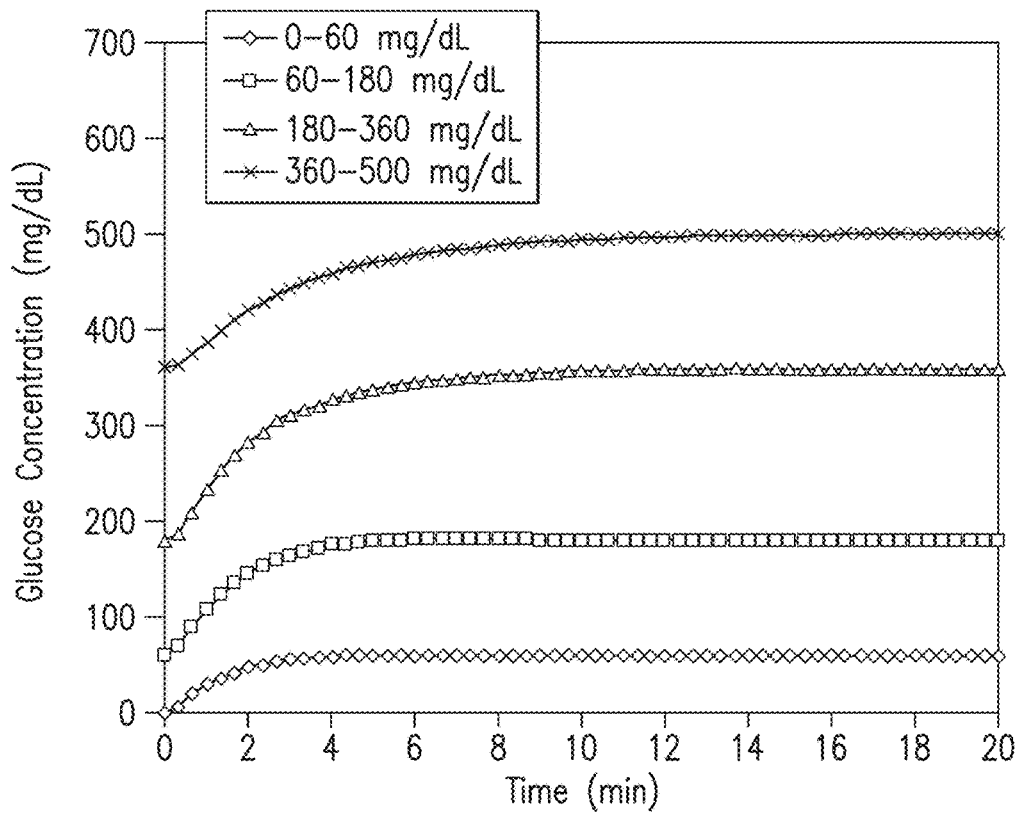

FIG. 11 is a plot showing simulated time-dependent glucose concentration on the surface of the vibrational diaphragm in response to additional glucose concentration increases.

Figure 12:
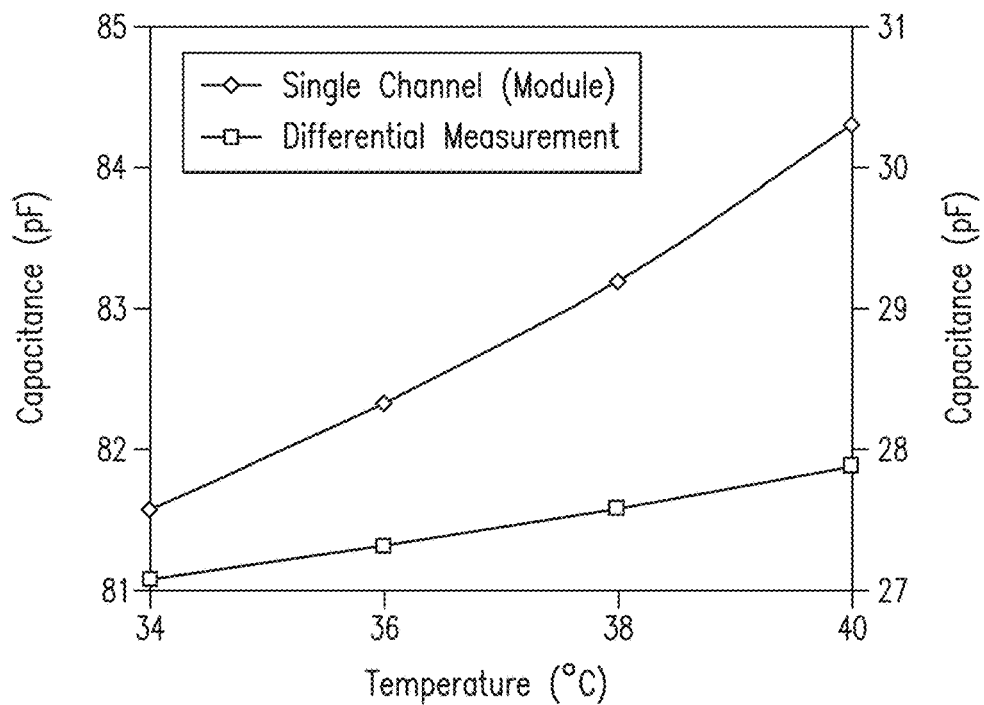

FIG. 12 is a plot showing a comparison of the capacitance output of a MEMS glucose sensor in changing temperature in single-module and differential measurements.

Figure 13:
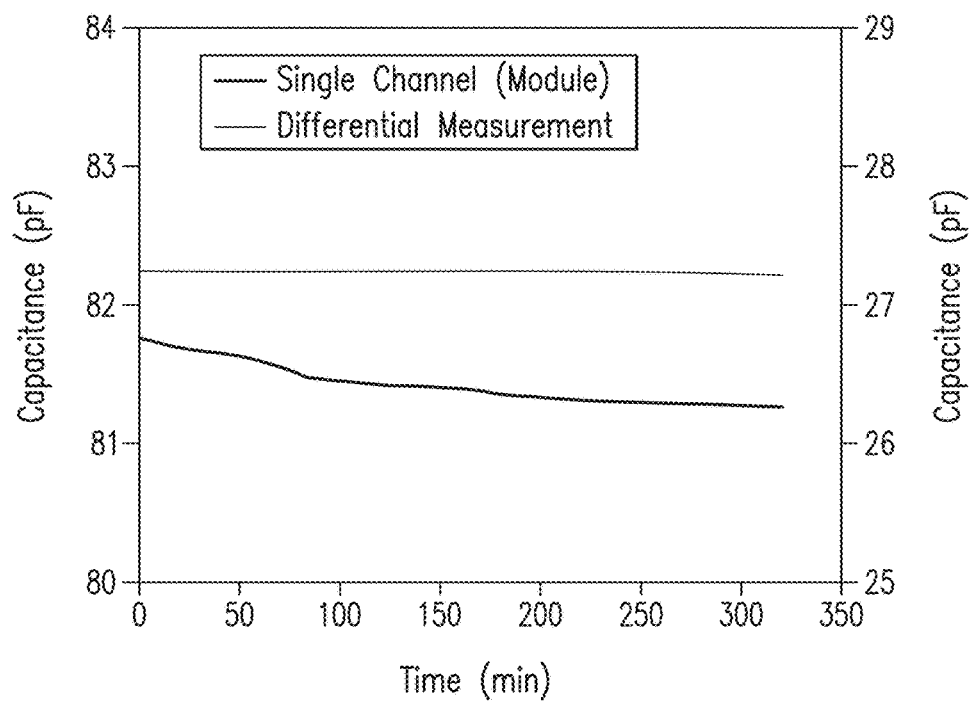

FIG. 13 is a plot showing a comparison of the capacitance output of a MEMS glucose sensor when the sensor is exposed to 90 mg/dL glucose solution for approximately 5 hours.

Figure 14A:
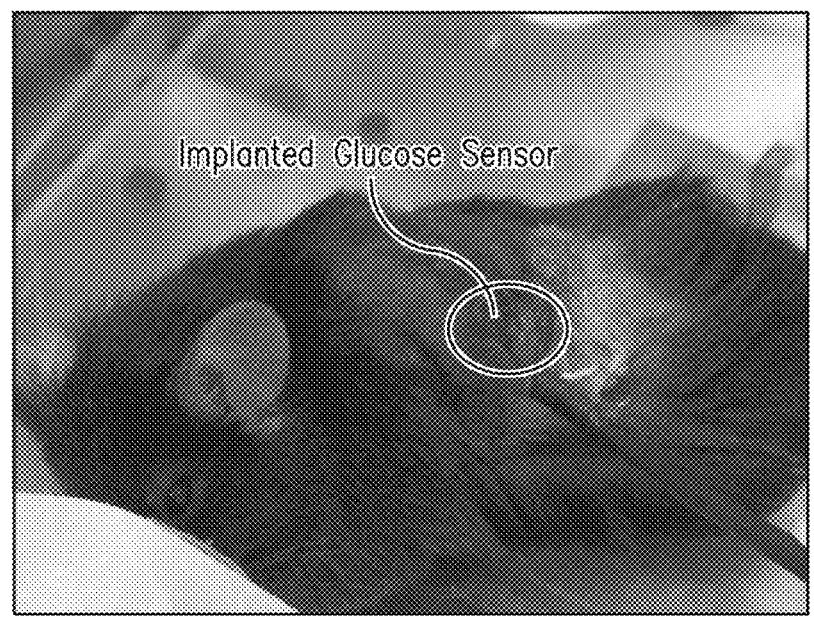
Figure 14B:
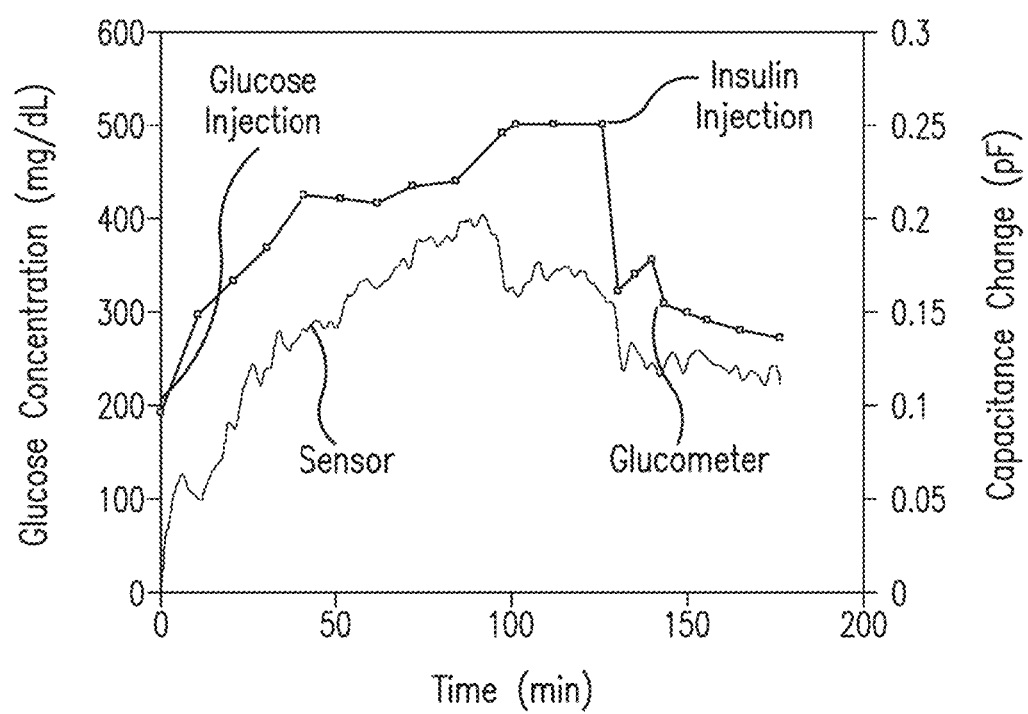

FIG. 14A is picture showing implanting a MEMS glucose sensor in a laboratory mouse FIG. 14B is a plot showing the differential capacitance change of the MEMS glucose sensor implanted in FIG. 14A as compared to readings from a commercial glucometer.

Figure 15:
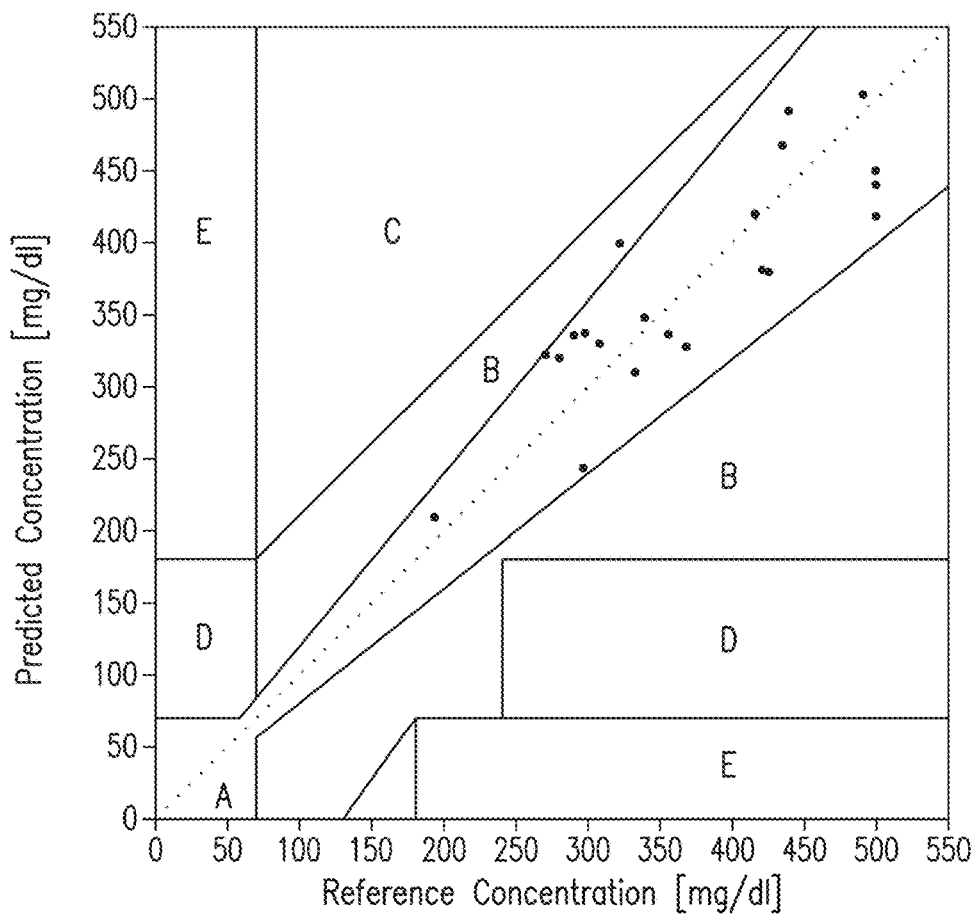

FIG. 15 is a plot showing Clarke error grid to assess the clinical accuracy of the estimated glucose value obtained from calibrating differential capacitance with reference glucose value.

Figure 16:
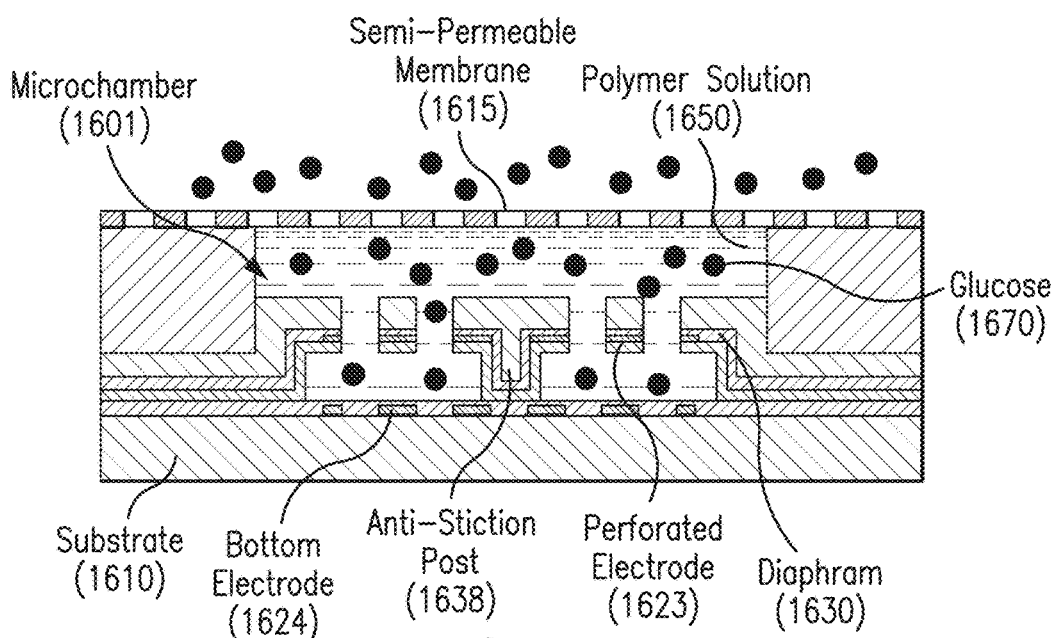

FIG. 16 is a schematic of a single-module MEMS dielectric glucose sensor according to some embodiments of the disclosed subject matter.

FIGS. 17A-17F are a diagram depicting a representative fabrication process of the single-module MEMS dielectric glucose sensor shown in FIG. 16: (a) Gold layer deposition and patterning to form a bottom gold electrode, and passivation of the electrode by Parylene; (b) Sacrificial photoresist layer deposition and patterning; (c) Parylene deposition and gold layer deposition and patterning to form a perforated electrode; (d) Parylene passivation layer deposition; (e) SU-8 deposition and patterning to form a diaphragm and a microchamber; (f) SU-8 patterning, sacrificial layer removal, and semi-permeable membrane bonding.

Figure 17A:
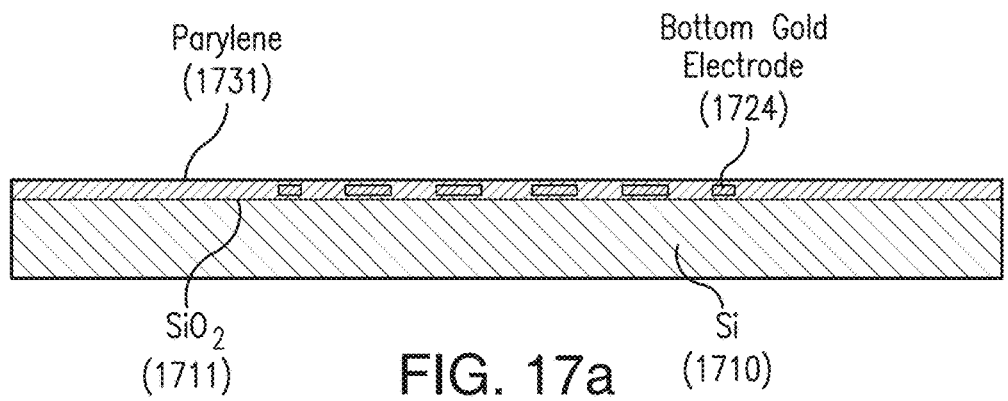
Figure 17B:
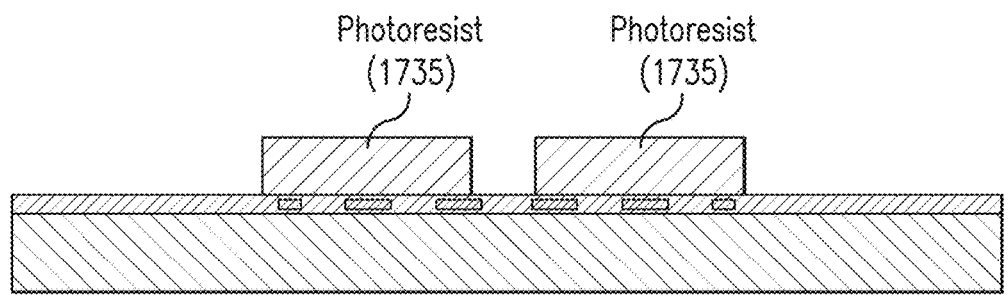
Figure 17C:
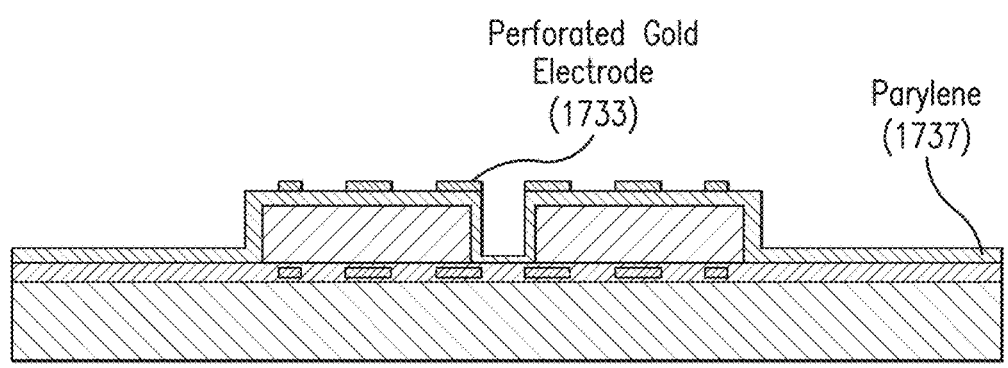
Figure 17D:
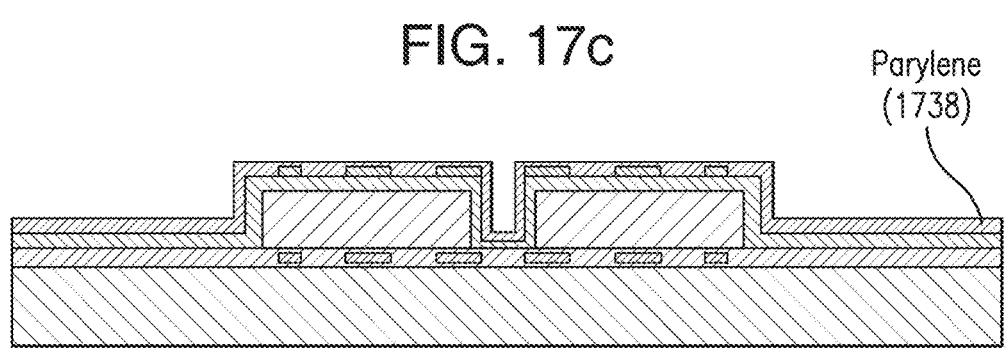
Figure 17E:
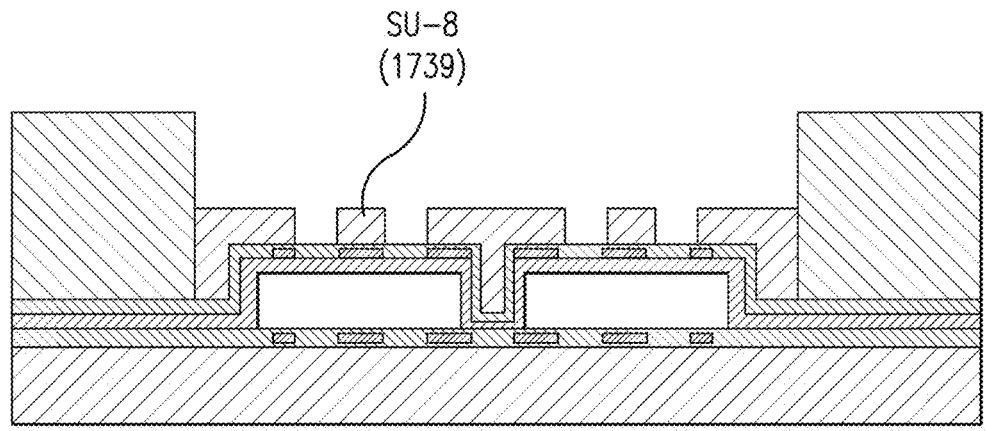
Figure 17F:
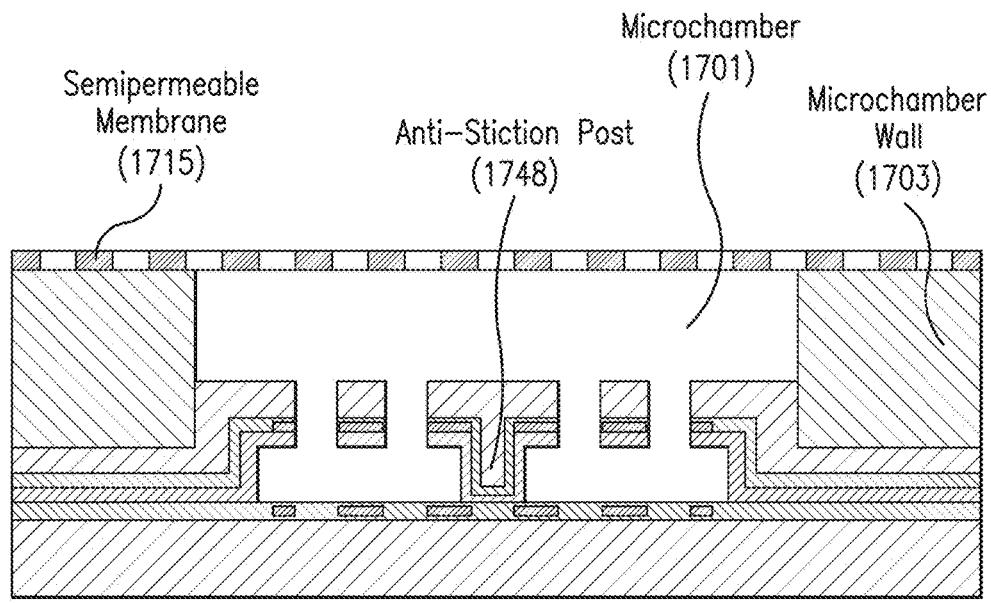
Figure 18:
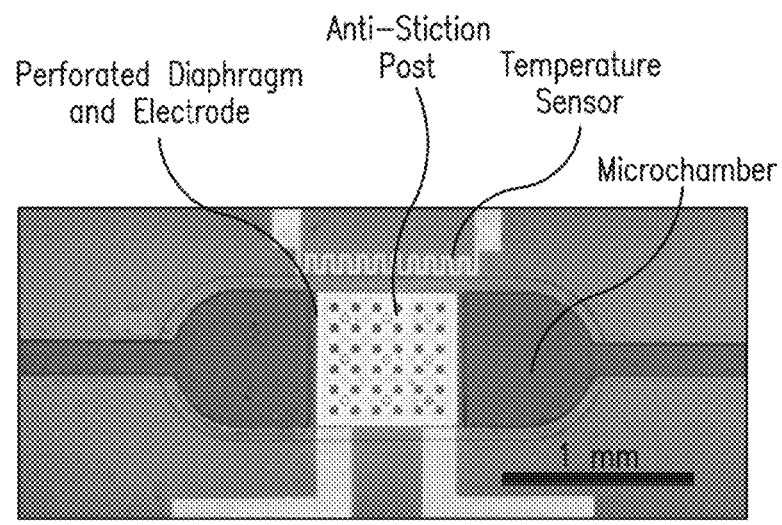

FIG. 18 are a micrograph image of a MEMS dielectric glucose sensor as fabricated by the process illustrated in FIGS. 17A-17F before packaging.

Figure 19:
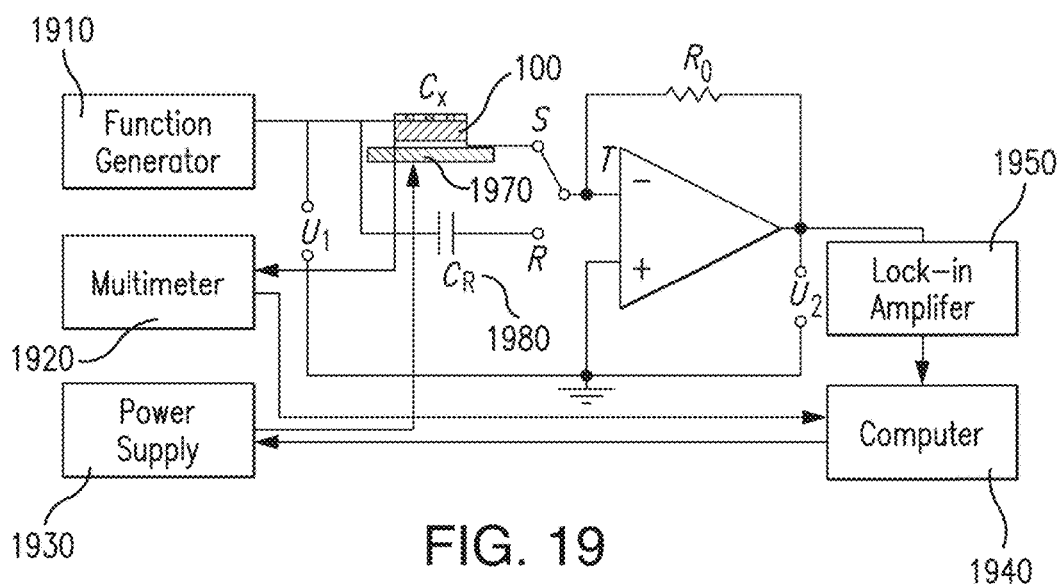

FIG. 19 is a diagram showing a representative setup and a capacitance/voltage transformation circuit for capacitance measurement of a MEMS dielectric glucose sensor according to some embodiments of the disclosed subject matter.

Figure 20:
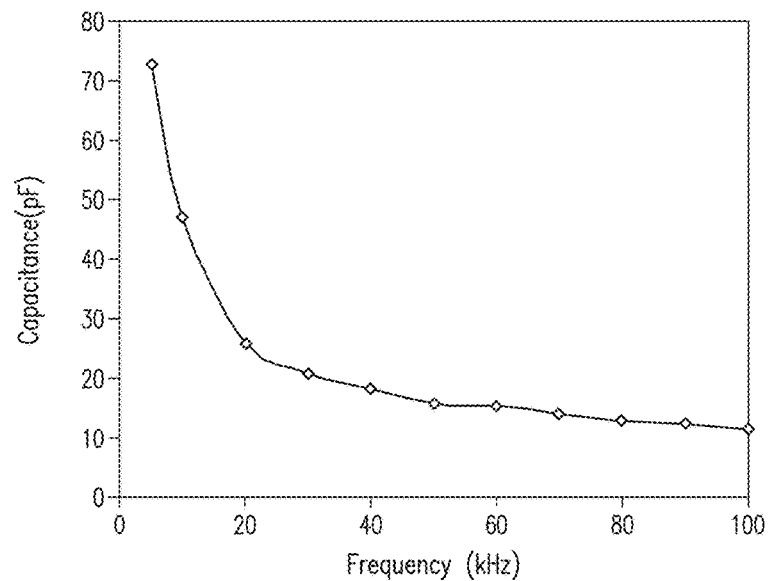

FIG. 20 is a plot showing frequency-dependent equivalent capacitance of a MEMS dielectric glucose sensor in the absence of glucose.

Figure 21:
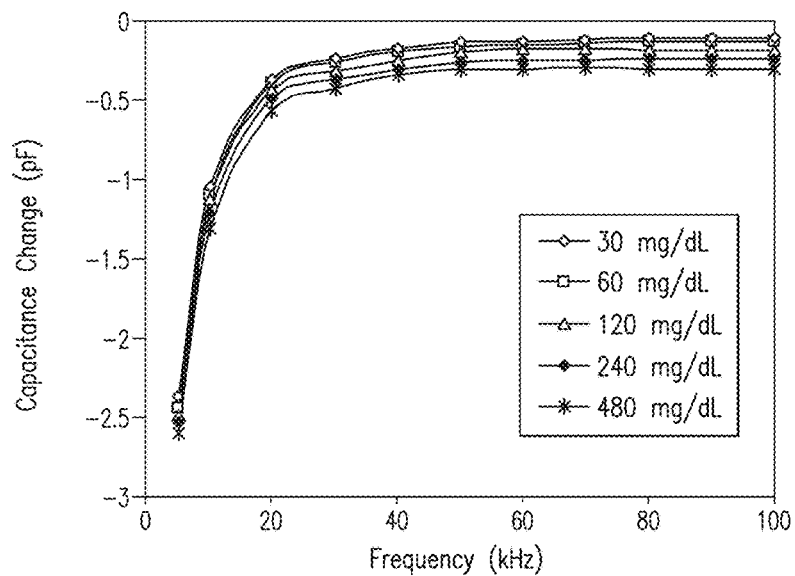

FIG. 21 is a plot showing the capacitance differences of the MEMS dielectric glucose sensor at various glucose concentrations as compared with the sensor capacitance in the absence of glucose.

Figure 22:
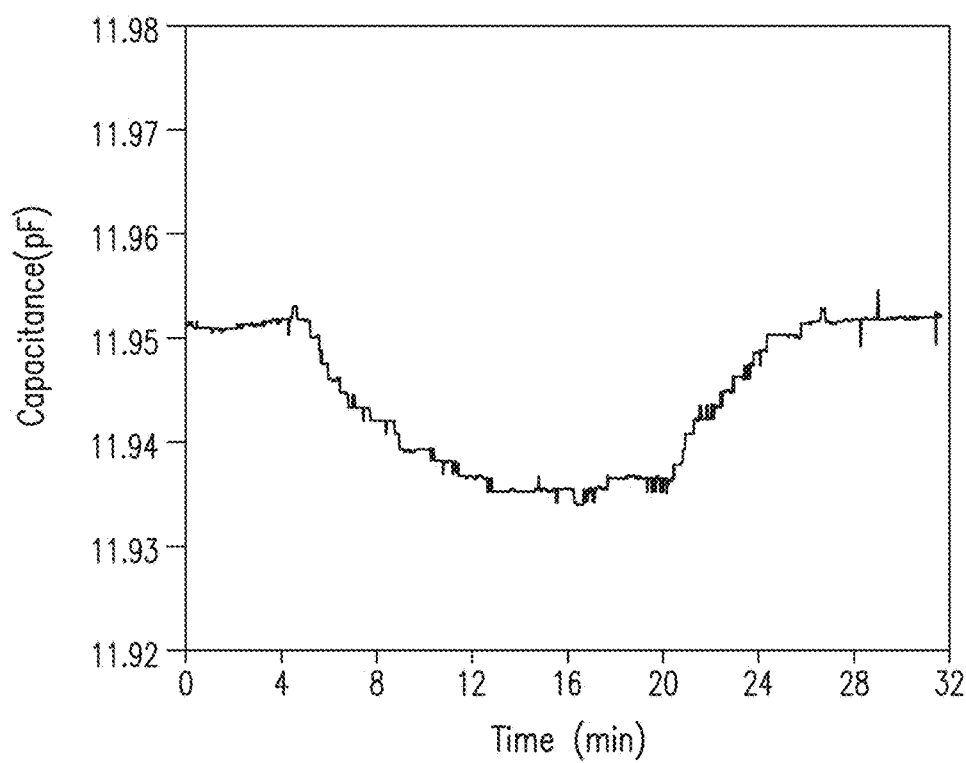

FIG. 22 is a plot showing time-dependent capacitance of the MEMS dielectric glucose sensor at 100 kHz as the sensor responded to glucose concentration changes from 60 to 120 mg/dL, which was then reversed to 60 mg/dL.

Figure 23:
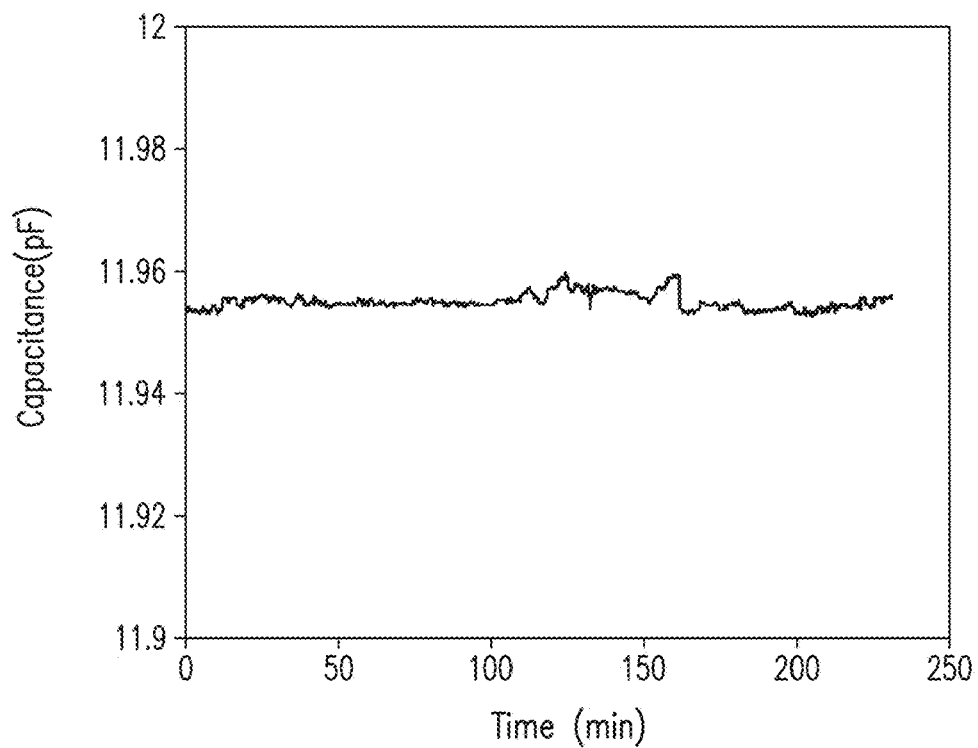

FIG. 23 is a plot showing the capacitance drift of the MEMS dielectric glucose sensor at 100 kHz over an extended time duration as the glucose concentration was held constant at 60 mg/dL.

Figure 24:
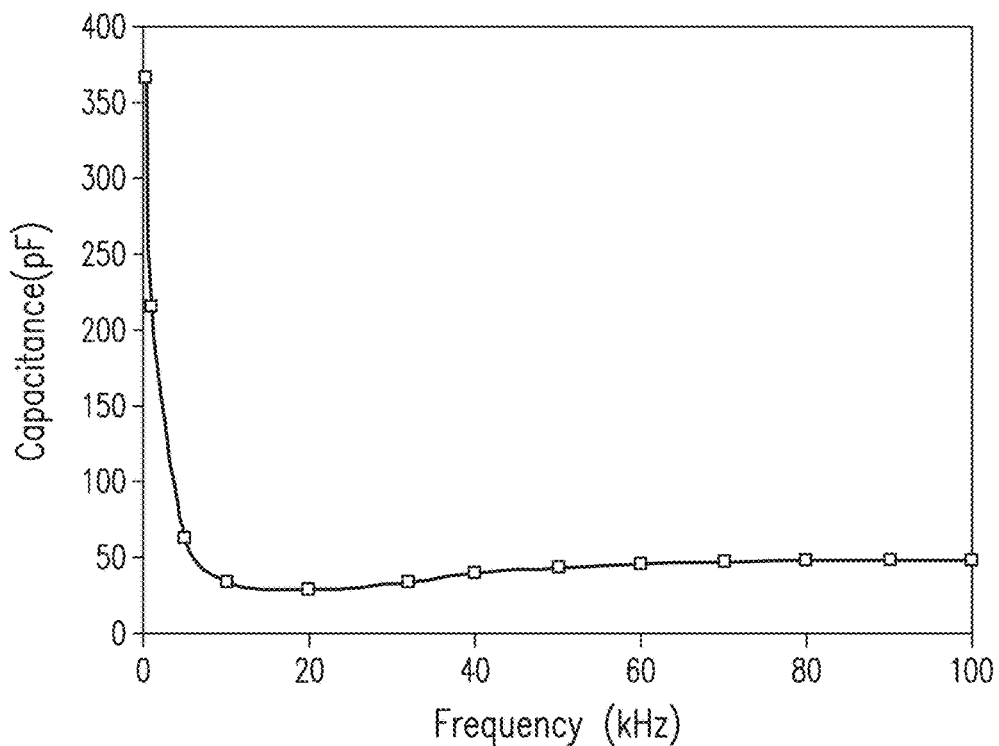

FIG. 24 is a plot showing the response of the MEMS dielectric glucose sensor to glucose free polymer solutions.

Figure 25:
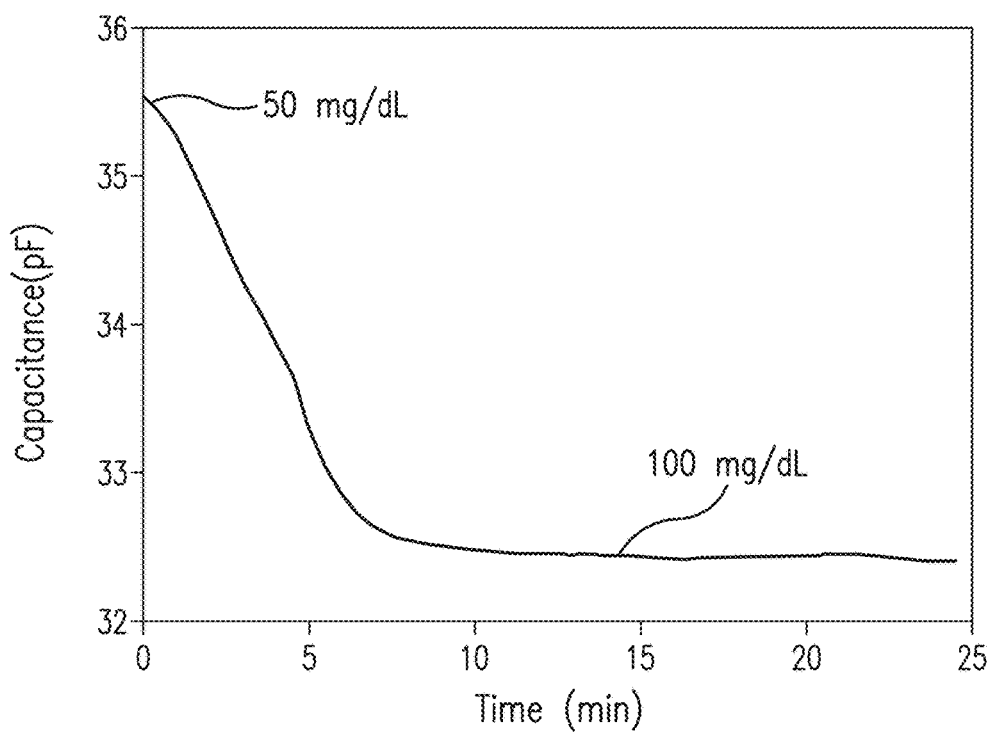

FIG. 25 is a plot showing time-dependent capacitance of the MEMS dielectric glucose sensor for a glucose concentration change (at 100 kHz).

Figure 26:
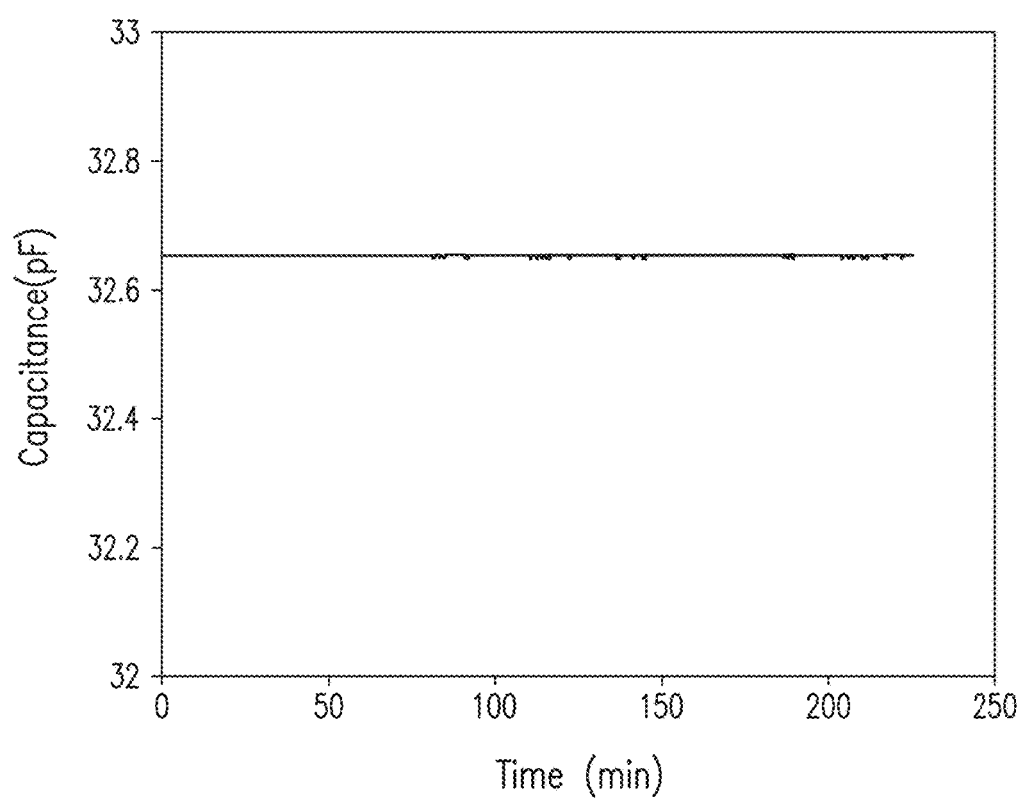

FIG. 26 is a plot showing the capacitance drift of the MEMS dielectric glucose sensor at 100 kHz over an extended time duration as the glucose concentration was held constant at 100 mg/dL.

Figure 1B:
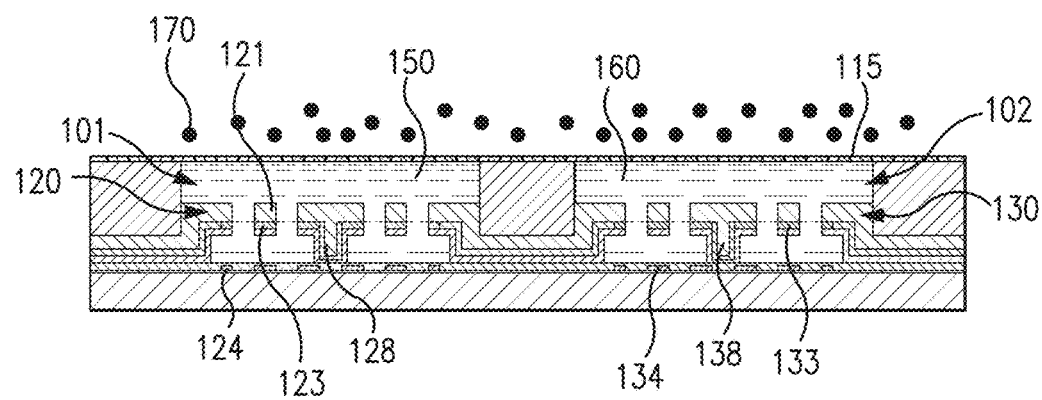

FIGS. 27A-27F are a diagram illustrating a representative process for fabricating a MEMS differential dielectric glucose sensor depicted in FIG. 1B: (A) Gold layer deposition and patterning to form bottom gold electrodes, and passivation of the electrodes by parylene; (B) Sacrificial photoresist layer deposition and patterning; (C) Parylene deposition and gold layer deposition and patterning to form perforated electrodes; (D) Parylene passivation layer deposition; (E) SU-8 deposition and patterning to form diaphragms and microchambers; (F) SU-8 patterning, sacrificial layer removal, and semi-permeable membrane bonding.

Figure 28A:
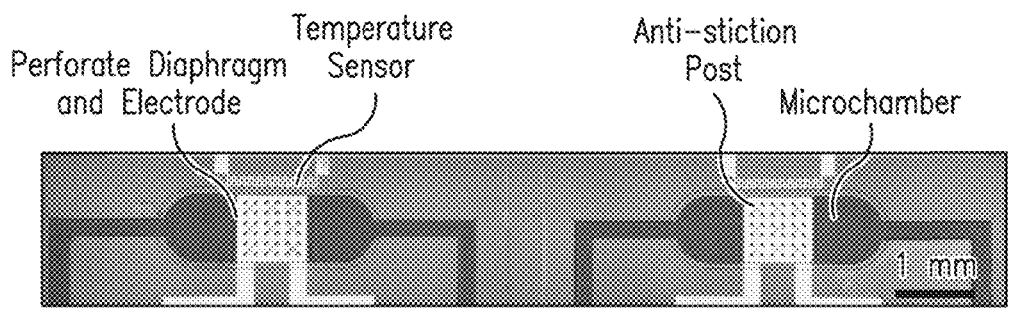
Figure 28B:
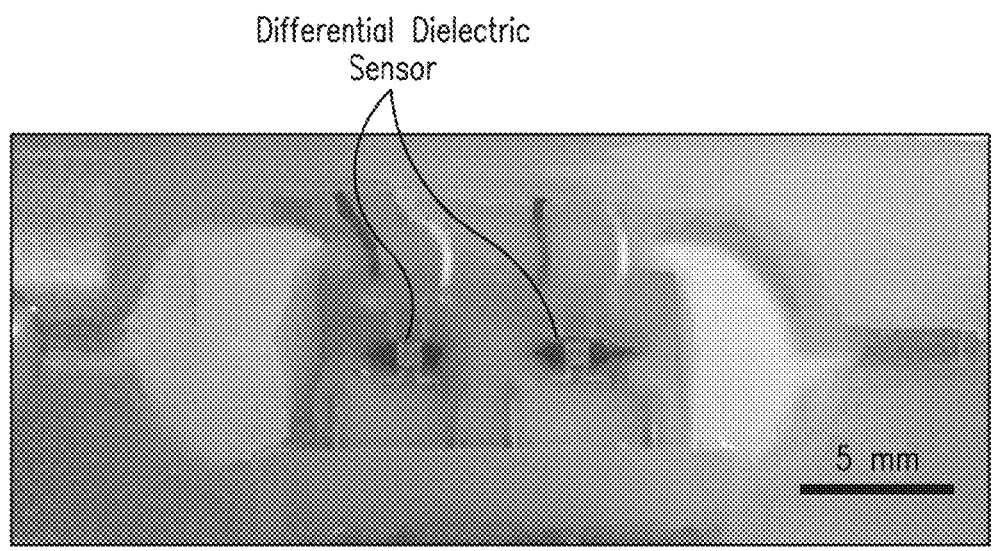

FIGS. 28A-28B are images of a differential MEMS glucose sensor according to some embodiments of the disclosed subject matter: (A) before, and (B) after packaging.

Figure 29:
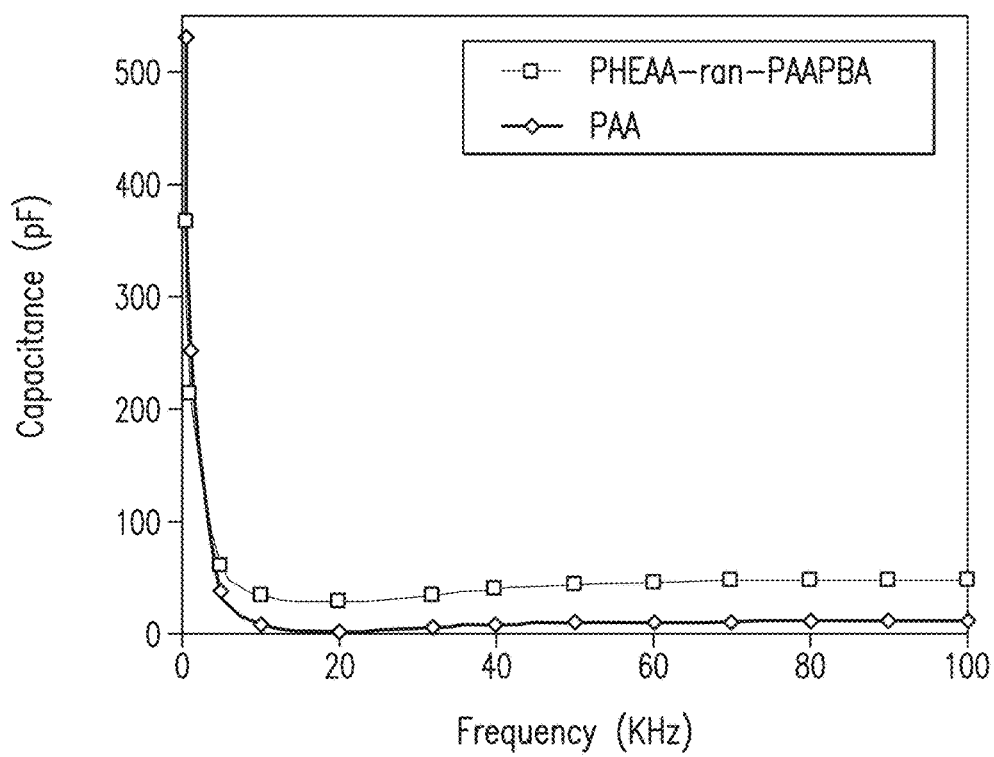

FIG. 29 is a plot showing the frequency responses of the PHEAA-ran-PAAPBA polymer solution and PAA polymer solution at 0 mg/dL glucose concentration when each was loaded in the sensing chamber of the differential MEMS glucose sensor of FIG. 28.

Figure 30:
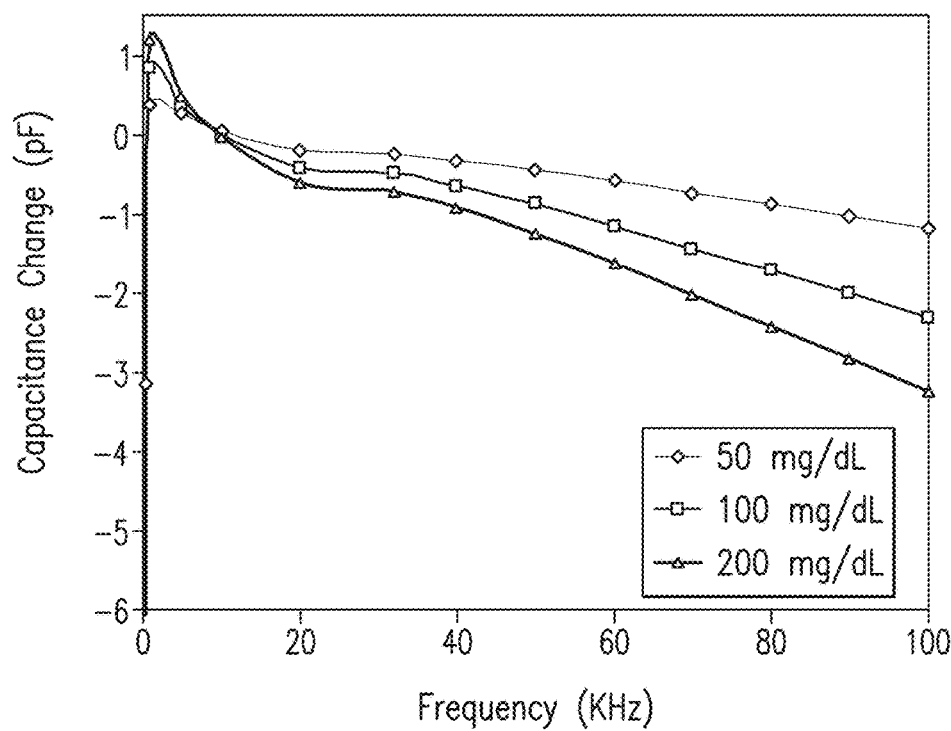

FIG. 30 is a plot showing the capacitance change of the differential MEMS glucose sensor filled with PHEAA-ran-PAAPBA solution at varying glucose concentration with respected to the capacitance at 0 mg/dL glucose concentration.

Figure 31:
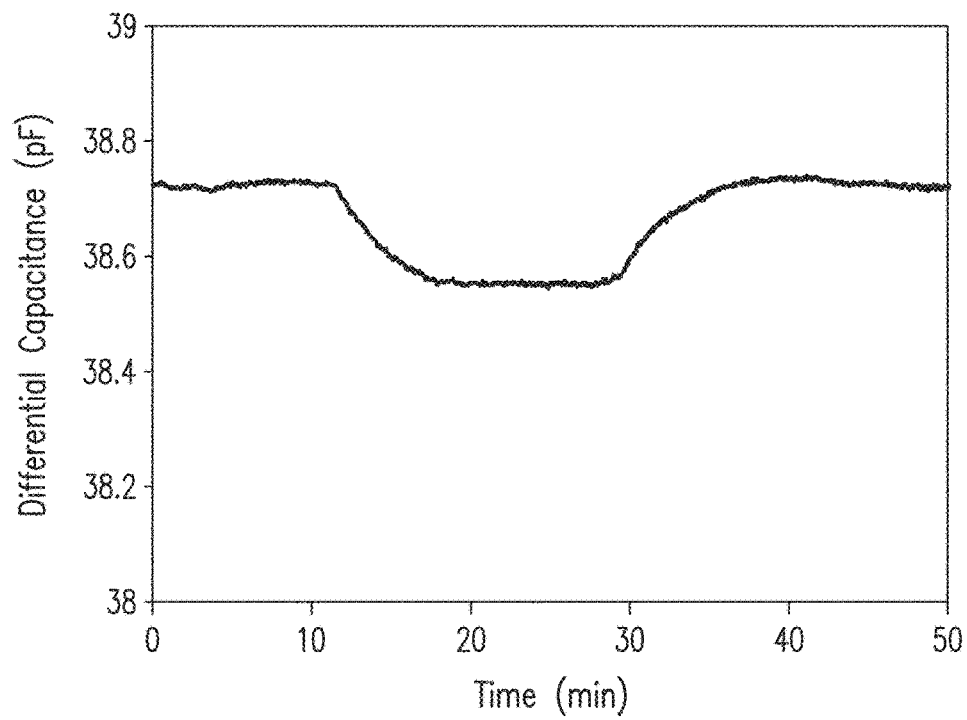

FIG. 31 is a plot showing the time-dependent capacitance of the differential MEMS glucose sensor at 32 kHz as the sensor responded to glucose concentration changes from 50 to 100 mg/dL, which was then reversed to 50 mg/dL.

Figure 32:
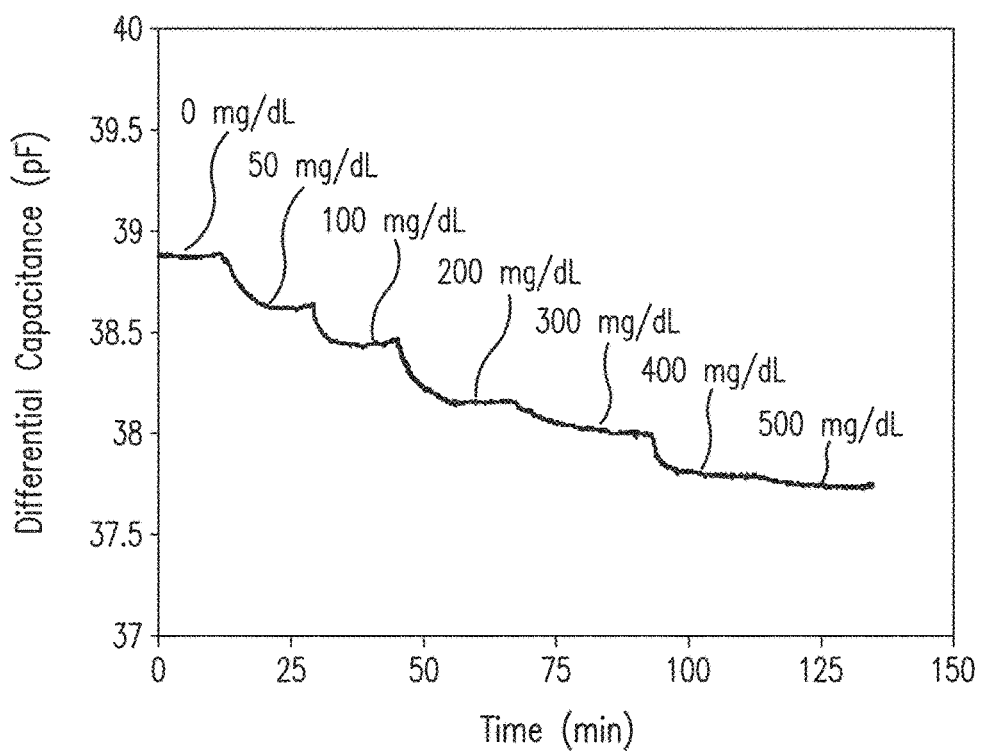

FIG. 32 is a plot showing the capacitance of the differential MEMS glucose sensor in response to a sequence of glucose concentrations.

Figure 33:
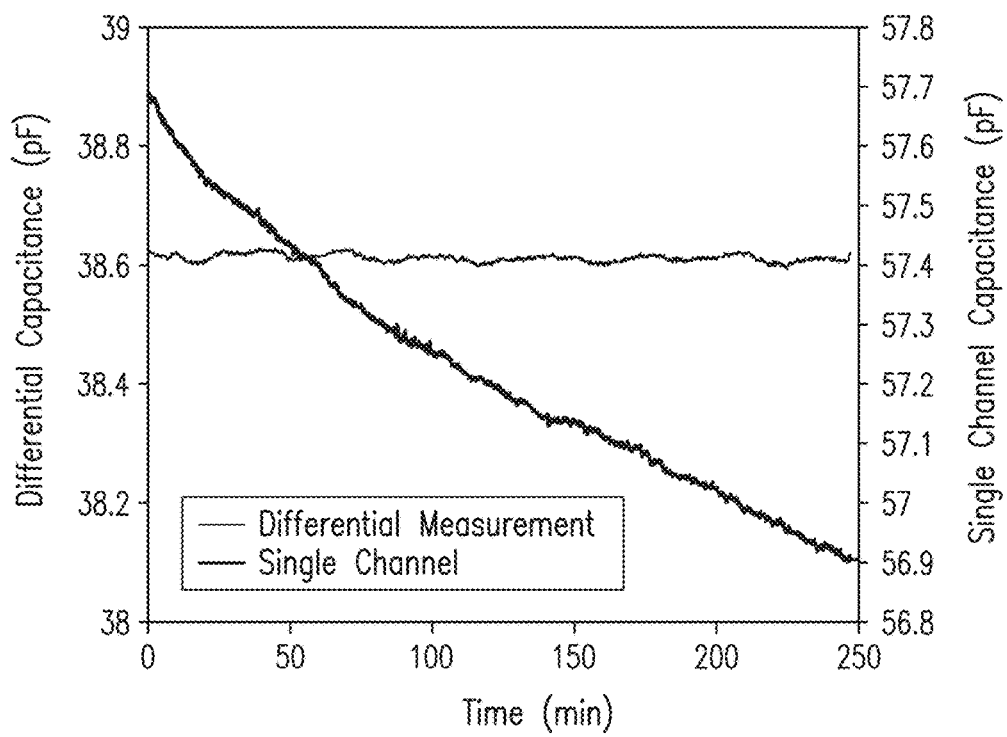

FIG. 33 is a plot showing the capacitance of the differential MEMS glucose sensor as compared to a single module MEMS glucose sensor over an extended time duration as the glucose concentration was held constant at 50 mg/dL.

Figure 34:
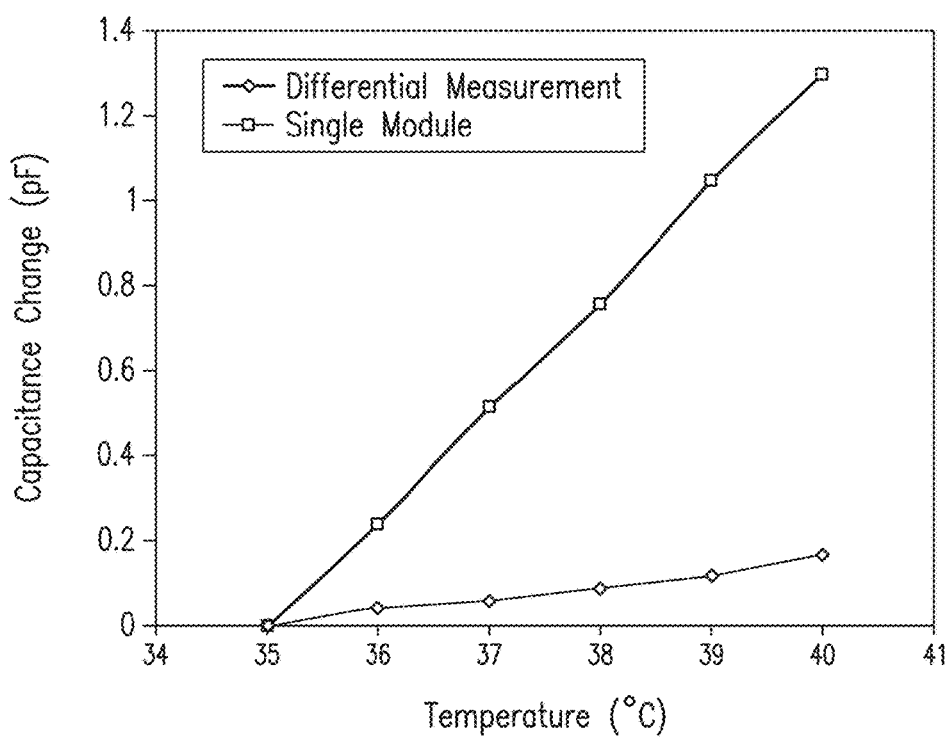

FIG. 34 is a plot showing a comparison of sensor capacitance output in changing temperature in single module and differential measurements.

Figure 35A:
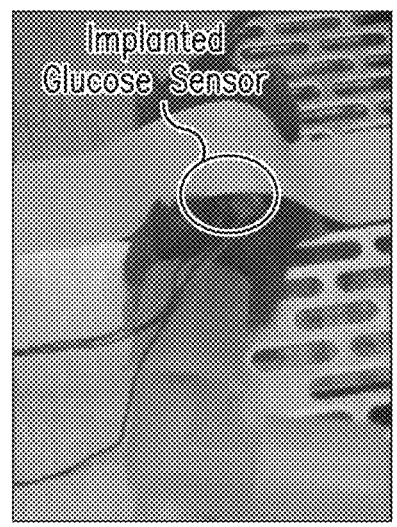

FIG. 35A is a picture showing sensor implantation in a laboratory mouse

Figure 35B:
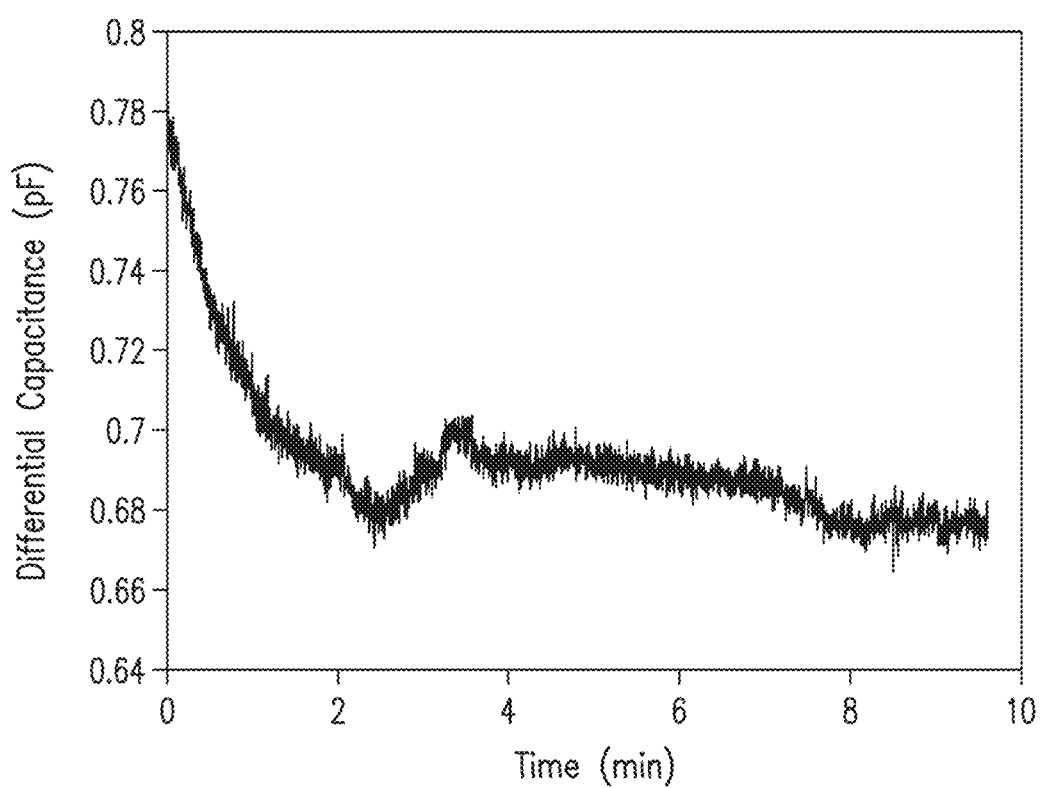

FIG. 35B is a plot of differential capacitance change of the implanted sensor according to FIG. 35A during the initialization.

Figure 36A:
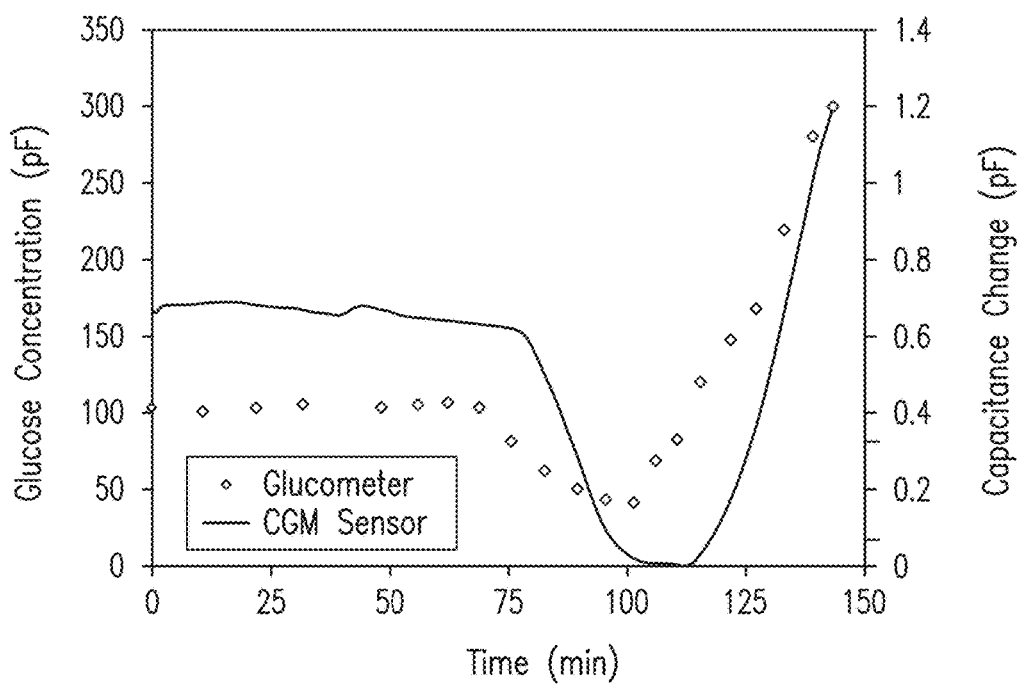
Figure 36B:
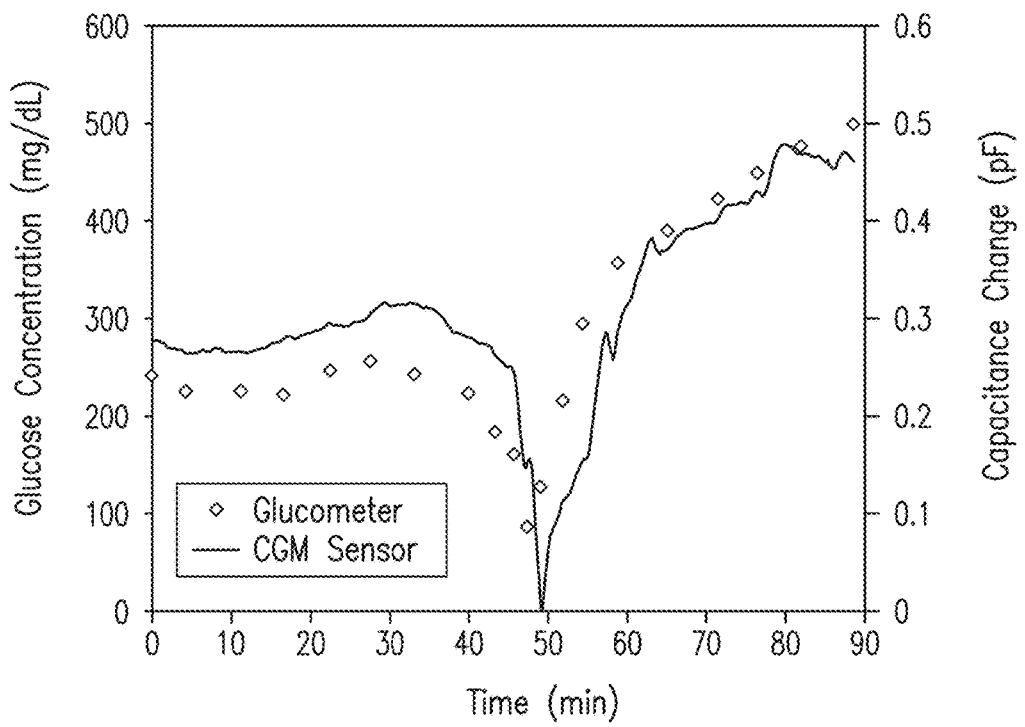
Figure 36C:
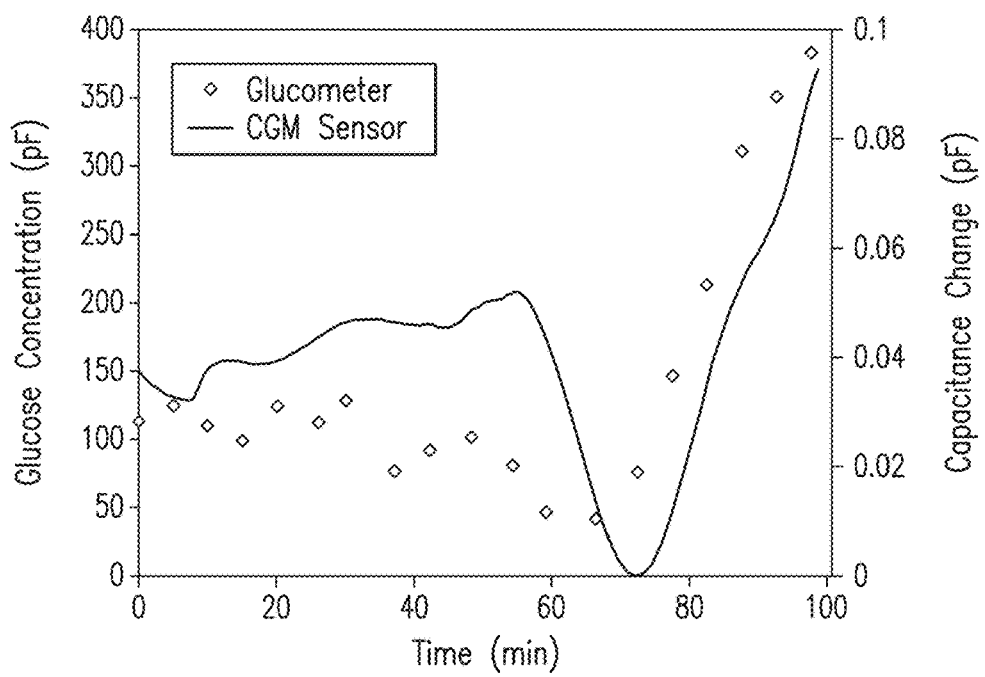

FIGS. 36A-36C are plots for differential sensor capacitance changes as compared to readings from a commercial glucometer of test subject mouse (A) one, (B) two, and (C) three.

Figure 37:
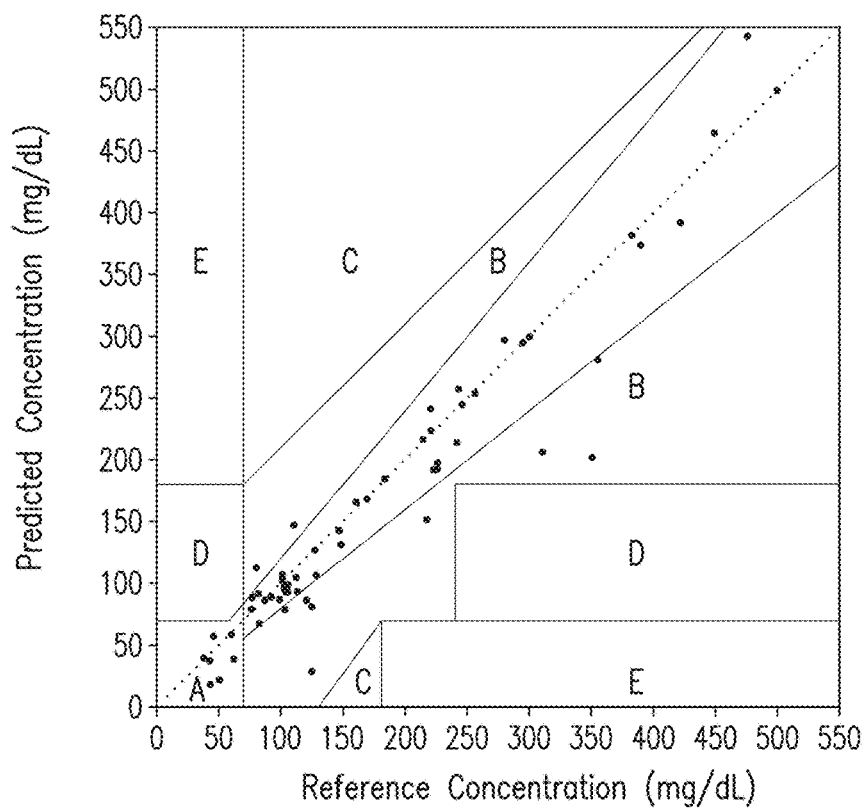

FIG. 37 is a plot of Clarke error grid to assess the clinical accuracy of estimated glucose values obtained from calibrating differential capacitance with reference glucose values.

Figure 38A:
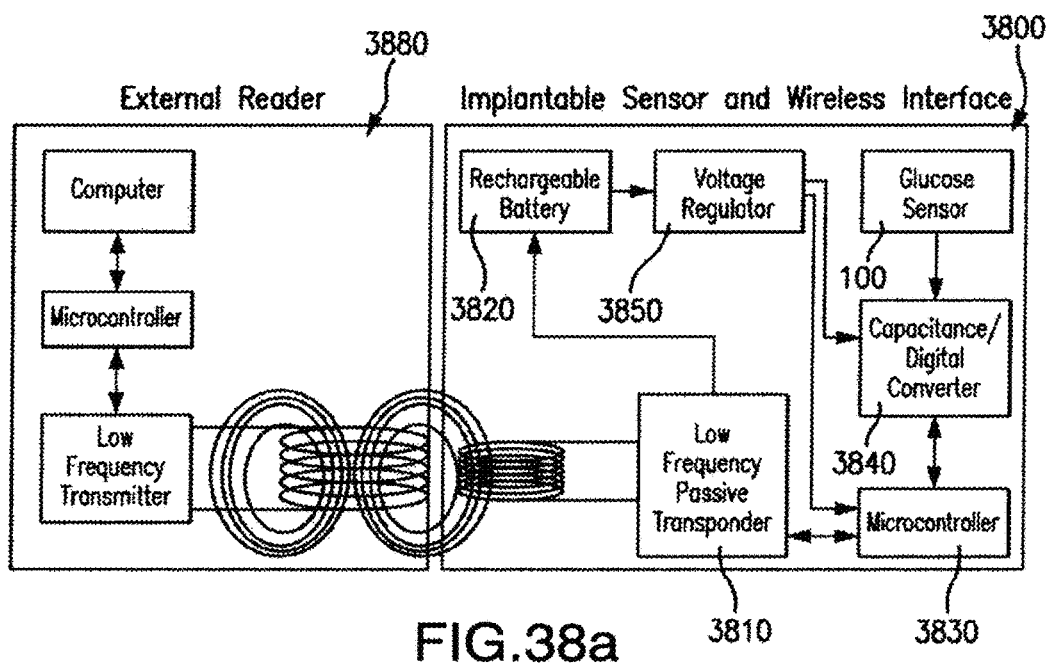

FIG. 38A is a schematic diagram showing a wireless communication between an implantable sensor and an external reader according to some embodiments of the disclosed subject matter.

Figure 38B:
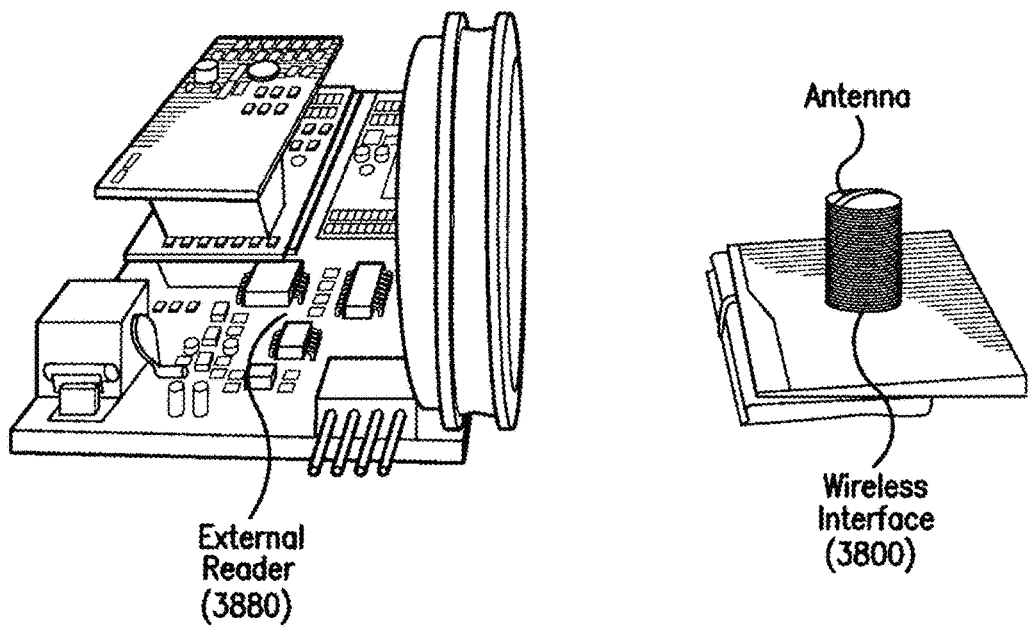

FIG. 38B is an image showing an external reader and a wireless interface used in an example of the disclosed subject matter.

Figure 39:
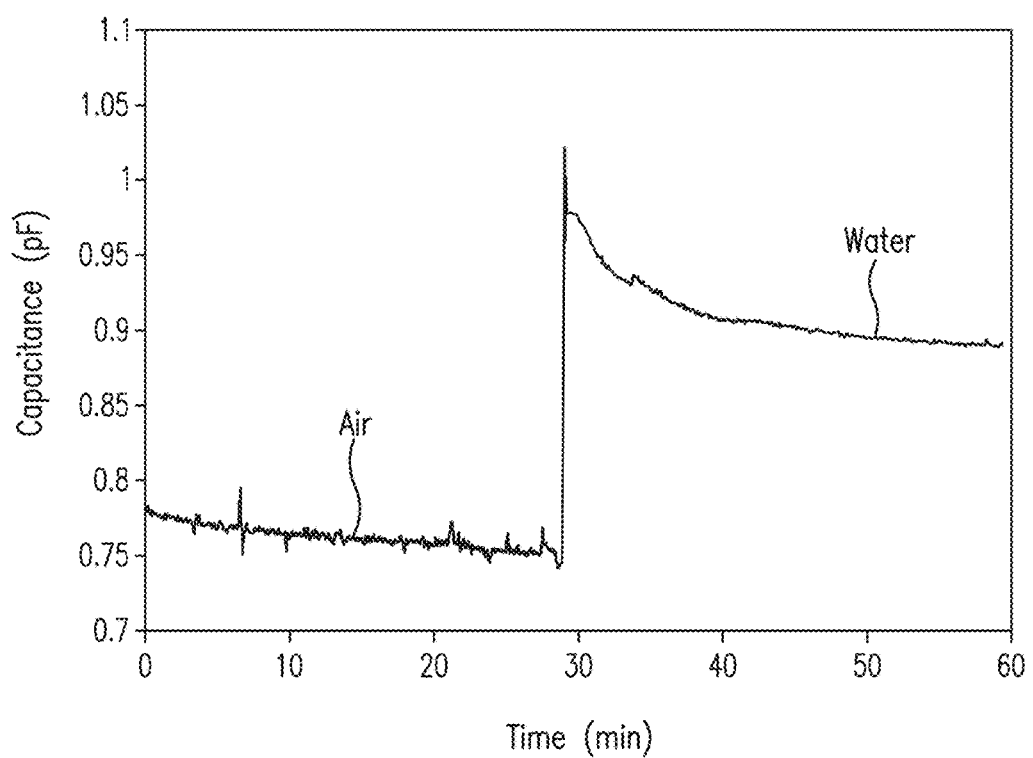

FIG. 39 is a plot showing the results of an example for testing the basic function of the wireless interface by changing the dielectrics sandwiched between two electrodes from air to water.

DETAILED DESCRIPTION

The disclosed subject matter provides for devices and techniques to monitor target analytes. More specifically, the disclosed subject matter provides for MEMS-based sensors and systems that can be used for continuous analyte monitoring, including continuous glucose monitoring (CGM). As used in, the microdevices are also referred to as sensors.

As used herein, the term "analyte" is a broad term and is used in its ordinary sense and includes, without limitation, any chemical species the presence or concentration of which is sought in material sample by the sensors and systems disclosed herein. For example, the analyte(s) include, but not are limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones. In one embodiment, the analyte is glucose. In various embodiments, the analytes can be other metabolites, such as lactate, fatty acids, cysteines and homocysteines.

As used herein, the term "suspended element" refers to a thin film structure suspended in the microchamber(s) of the microdevice. The suspended element can include subparts, e.g., a thin film electrode, a passivation layer. In some embodiments, the suspended element includes a magnetically active component that can move in response to an external magnetic field.

As used herein, the term "vibrational element" refers to a mechanical moving part, which is capable of vibrating. The vibrational element as used in presently disclosed subject matter includes, but is not limited to, a vibrational diaphragm. The vibrational element can be, or a part of the suspended element.

The microdevices of the disclosed subject matter can be either viscosity-based or permittivity based. FIG. 1A illustrates the structure of an example viscosity-based microdevice. As shown in FIG. 1A, the microdevice includes a semi-permeable membrane structure 115, a substrate 110, a first microchamber 101 (hereinafter also referred to as the sensing chamber) and a second microchamber 102 (hereinafter also referred to as the reference chamber). Each of the two microchambers 101 and 102 is formed between the semi-permeable membrane structure 115 and the substrate 101, and includes a suspended element 120 and 130, respectively. The first microchamber 101 is adapted to receive a solution 150 including the polymer, and the second microchamber is adapted to receive a reference solution 160 for screening effects not caused by the target analyte.

As shown in FIG. 1A, the two microchambers 101 and 102 are isolated from each other (not fluidically connected), each sealed by the substrate 110, chamber side walls 103, 104, and 105, respectively. The configuration of the two microchambers can be identical. The semi-permeable membrane structure 115 can be a continuous semi-permeable membrane that covers and seals the two microchambers. Alternatively, the semi-permeable membrane can include two semi-permeable membrane portions that each covers and seals the sensing chamber and reference chamber, respectively. The semi-permeable membrane structure is permeable to the target analyte 170 and impermeable to the polymer. Therefore, when the sample that can contain target analyte 170 is placed in contact with the semi-permeable membrane structure, the target analyte 170, if present in the sample, permeates through the semi-permeable membrane structure 115 and enters the first microchamber 101 and the second microchamber 102, respectively.

The sensing chamber can be loaded with a solution 150 that includes a polymer, also referred to as the sensing polymer or target analyte-sensitive polymer hereinafter, that binds with the analyte. The sensing polymer is prevented from escaping from the first microchamber through the semi-permeable membrane structure. The sensing polymer can be biocompatible. In one embodiment, the biocompatible polymer can reversibly bind to the analyte of interest. The binding between the polymer and the analyte can result in changes of the physical characteristics (e.g., the viscosity and/or permittivity) of the polymer solution, which can be measured to determine the presence and amount of the analyte in the sample.

For example, when the analyte is glucose, through proper adjustment of the composition percentage of the boronic acid moieties on the polymer and polymer concentrations, the polymer can detect and differentiate glucose from other monosaccharides and disaccharides. Applying this polymer to the sensor as disclosed herein can enable highly reliable, continuous monitoring of glucose in ISF in subcutaneous tissue.

As noted, the binding between the polymer and the analyte of interest can be reversible. For example, the binding and dissociation between the target analyte and the sensing polymer can be an equilibrium phenomenon driven by the concentration of the analyte in the sensing chamber. As the analyte can move freely in and out of the sensing chamber through the semi-permeable membrane which the polymer cannot, the amount of the analyte bound with the sensing polymer depends on the concentration of the analyte in the sample.

In one embodiment, a suitable polymer having boronic acid moieties can be formed as a copolymer of at least two monomers, where one of the monomers includes at least one boronic acid functional group. A copolymer can be synthesized with these monomers via classic free radical copolymerization processes. In various embodiments, a suitable polymer includes, but is not limited to, a polymer that contains boronic acid groups, or other receptor groups that recognize the given analytes. In one embodiment, the polymer is PAA-ran-PAAPBA, which is an amphiphilic copolymer containing two components, hydrophilic polymer segment polyacrylamide (PAA) and hydrophobic polymer segment poly(3-acrylamidophenylboronic acid) (PAAPBA).

A solution of PAA-ran-PAAPBA can undergo a viscosity change as well as a permittivity change when interacting with glucose molecules, as discussed in US Patent Application Publication No. 20120043203, assigned to the common assignee, the disclosure of which is incorporated herein by reference in its entirety. In another embodiment, the sensing polymer is PHEAA-ran-PAAPBA, which is an amphiphilic copolymer containing two components: PAAPBA and poly(N-hydroxyethyl acrylamide) (PHEAA). PAAPBA is a hydrophobic glucose-sensitive component, while PHEAA is a hydrophilic and nonionic component, and primarily serving to improve the overall water solubility of the entire copolymer. When added to an aqueous solution of PHEAA-ran-PAAPBA, similar to PAA-ran-PAAPBA, glucose binds reversibly to the phenylboronic acid moieties in the PAAPBA segments to form strong cyclic boronate ester bonds, while having almost no response to other potential interferents, such as fructose, galactose, and sucrose.

To screen out effects not caused by the target analyte, for example, environmental factors such as temperature, the reference chamber can also be loaded with a solution of another polymer (the reference polymer). The reference polymer does not bind with the target analyte. Also, the reference polymer should not bind with or otherwise react with other substance in the sample solution to impact the property of the reference solution in a similar way as the target analyte impacts the corresponding property in the sensing polymer solution. The reference polymer can be selected to have similar hydrophilic blocks to those in the sensing polymer, but have no phenylboronic acid moieties. For example, glucose-unresponsive PAA or PHEAA can be used as a reference polymer for glucose detection. The viscosity of PAA (or PHEAA) solution is glucose-independent. The analyte-free viscosity of the sensing polymer solution can be similar to that of the reference polymer solution.

When the microdevice is viscosity-based, as shown in FIG. 1A, the suspended elements 120 and 130 of the sensing chamber and the reference chamber can each act as a vibrational diaphragm, which can be actuated by an external alternating field. The suspended elements (120, 130) each can include structural elements (121, 131), e.g., made from parylene, for structural integrity, passivation, and support for other components. For example, suspended element 120 and 130 can each include a magnetically active component 122 and 132, respectively, e.g., made of a magnetic material such as permalloy.

When an alternating electromagnetic field is applied, the suspended element 120 (as well as 130) can vibrate. The source of the electromagnetic field, its relative configuration with the microdevice, and the mechanism in which the varying electromagnetic field interact with the vibrational diaphragm can be as disclosed in US Patent Application Publication No. 20120043203, or modifications thereof as will be appreciated by those skilled in the art. Therefore, when the target analyte binds with the polymer, the viscosity change of the polymer solution can influence the vibration of the suspended element 120, while the vibration of the suspended element 130 in the reference chamber will not change. The vibration of the suspended element 120 can be measured by the capacitance of a capacitor formed by a top electrode 123 included in the suspended element 120, a bottom electrode 124 formed on the substrate, and an air gap 125 therebetween.

Similarly, the vibration of the suspended element 130 can be measured by the capacitance of a capacitor formed by a top electrode 133 included in the suspended element 130, a bottom electrode 134 formed on the substrate, and an air gap 135 therebetween. The top and bottom electrode can be made from any common materials suitable for use in electrodes, such as gold, copper, other metals or alloys. By measuring the difference of the vibrational behaviors, such as magnitude, of the suspended element 120 and 130, the presence and/or amount of the analyte in the sample can be determined.

FIG. 1B illustrates the structure of an example permittivity-based microdevice. The reference numerals in FIG. 1B represent corresponding elements in FIG. 1A. While similar to FIG. 1A, the suspended element 120 and 130 each include openings, or perforations, that allow the polymer solution and the reference solution to fill the gap between the respective suspended element and the substrate. In addition, the suspended elements can also be supported by antistiction post (128 and 138) formed from the substrate for structural stability. In this manner, the capacitance of the capacitor of formed between the top electrode 123, bottom electrode 124, and the polymer solution filled therebetween can be measured to detect any permittivity change caused by the analyte, and compared with the permittivity change of the reference solution. In some embodiments, the device does not include a reference chamber, and the permittivity change of the sensing chamber is directly correlated with the analyte presence and/or concentration.

Exemplary techniques for fabrication of the devices illustrated in FIGS. 1A and 1B will be discussed in further detail in Example 1 and Example 4.

Semi-permeable membranes are well known in the art. The semi-permeable membranes suitable for the microdevices of the disclosed subject matter can be obtained from commercial sources and selected based on pore sizes or cut-off molecular weight. In one embodiment, the semi-permeable membrane is selected to be cellulose acetate.

In certain embodiments, the disclosed subject matter provides an implantable monitor comprising a MEMS affinity device as described above coupled with a wireless interface. The wireless interface can include a capacitance digital converter coupled with the microdevice and adapted to produce a digital signal representing a measurement of the target analyte in the interstitial of the subject; a microcontroller coupled with the capacitance digital converter; and a transponder coupled with the microcontroller to transmit the digital signal received from the capacitance digital converter to an external reader.

In various embodiments of the disclosed subject matter, the sensor can be used to determine the level of an analyte in the body, for example oxygen, lactase, insulin, hormones, cholesterol, medicaments, viruses, or the like. The sensor can use any known method to provide an output signal indicative of the concentration of the target analyte. The output signal is typically a raw data stream that is used to provide a useful value of the measured analyte concentration. In general, before the devices is used to detect or monitor a target analyte, they are first calibrated using samples containing known amount of the target analyte to obtain correlations between sensor response (e.g., capacitance readout) and the known concentration of the calibration sample. Thereafter, in the monitor of the target analyte, the pre-established correlations can be used to interpret the output signals of the sensor and determine the presence and/or concentration of the target analyte in a test sample.

In certain embodiments of the disclosed subject matter, the sensor is used to monitor glucose as the target analyte. In these embodiments, the sensor can measure a concentration of glucose or a substance indicative of the concentration or presence of the glucose by using a specific polymer in the sensor.

The sensor can also be used for other applications. In addition to diabetes, the proposed miniature CGM device can also be used for glucose monitoring for other diseases (e.g., glycogen storage disease and hyperinsulinaemic hypoglycaemia).

The method can be extended to other metabolites, such as lactate, fatty acids, cysteines and homocysteines. For example, in emergency medicine, lactate monitoring can be used to predict possible organ failure of trauma patients, organ transplant patients, and patients with other critical conditions.

Further, the methods disclosed herein can be used as a reliable method for long-term monitoring of metabolites. Such methods can have great military significance. For example, a miniature device for glucose detection with fully electronic readout would have significant applications in protecting armed forces in the field. It can also provide a platform to enable the delivery of drug treatments and nutritional supplements to protect and enhance performance in military personnel.

Moreover, the disclosed method can be applied to the diagnosis of disease. For example, the development of boronic acid based glucose sensing systems can be extended to other analytes, such as human viruses and bacteria, since many of those microorganisms carry glycoproteins on the exterior surface that can be targeted by the boronic acid based binding motifs.

Metabolic monitoring is of great utility to environmental monitoring. Changes in the concentrations of metabolites are the precursors and products of enzymatic activity, and can be associated with biological function and regulation. Metabolic monitoring hence can be used for environmental monitoring, e.g., risk assessment of chemicals and diagnosis of diseases in wild animals. It can also be used as a tool to better understand the underlying mechanisms of action of toxic compounds in the environment.

Additional aspects and embodiments of the disclosed subject matter are illustrated in the following examples, which are provided for better understanding of the disclosed subject matter and not limitation. In all the examples, glucose is used as the target analyte. As such, for convenience, the disclosed microdevices will be also referred to as glucose sensors.

Example 1. A MEMS Differential Viscometer

Affinity glucose sensors based on viscosity detection using cantilever or diaphragm based vibrational elements are disclosed, e.g., in U.S. Patent Application Publication No. 20120043203. These devices can include a single sensing element (hence are also referred to as "single-module" devices herein) that measures glucose-induced viscosity changes in PAA-ran-PAAPBA polymer solutions. The results have demonstrated the feasibility of these devices in CGM. However, requirements for closed-loop temperature control and minimum environmental disturbances during the sensor operation can present difficulties for implantable applications for these sensors, in which the simplicity in device design and stability in device performance are desired.

Illustrated herein is a MEMS differential glucose sensor that can reject undesired common mode interferences through differential measurements, allowing accurate glucose detection. This sensor includes two magnetically driven vibrating diaphragms each situated inside a microchamber. One of the microchambers (the sensing chamber) is filled with a sensing solution of PHEAA-ran-PAAPBA, while the other microchamber (reference chamber) contains a reference solution of PHEAA that does not bind or otherwise react with glucose or other components of the sample under analysis. As glucose permeates through a semi-permeable membrane into each chamber, the viscosity of the sensing polymer solution increases due to glucose binding, while the viscosity of the reference solution only changes with environmental disturbances. Thus, measurement of the viscosity difference between the two chambers through differential capacitive detection of the vibration damping allows determination of the glucose concentrations while rejecting common mode disturbances. In-vitro and in-vivo data as described in connection with FIGS. 7, 8, 12-15 demonstrate the value of this sensor for highly stable subcutaneous CGM applications.

Figure 2:
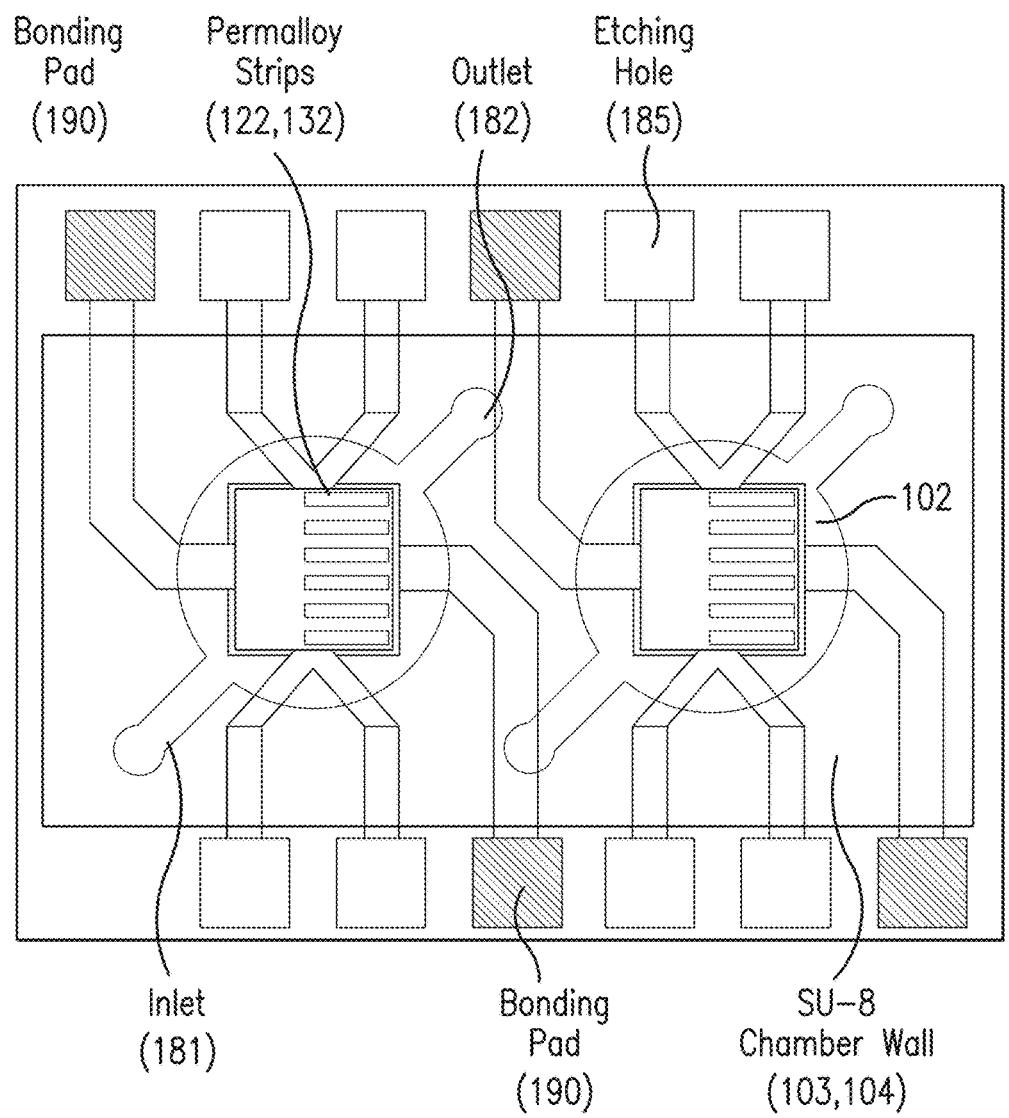
FIG. 2 is a schematic top view of a microdevice according to some embodiments of the disclosed subject matter.

The structure of an example CGM sensor is illustrated in FIG. 1 (side view). FIG. 2 is a top view of the sensor as fabricated according to the method disclosed in connection with FIG. 4. A pair of surface machined freestanding diaphragms (120, 130), one situated inside a sensing microchamber 101 (sensing diaphragm 120) while the other inside a reference microchamber 102 (reference diaphragm 130), each vibrate under an external AC magnetic field. A top (moving) electrode (123, 133) is embedded in each of the diaphragms and is separated from a fixed electrode (124, 134) on a substrate below by an air gap, forming a diaphragm position-sensing capacitor. Magnetically responsive permalloy thin-film strips (122, 132) are integrated on each of the diaphragms (120, 130) and are passivated along with the moving electrodes to avoid direct contact with the polymer solution 150 and reference solution 160. The CGM sensor as depicted in FIG. 2 also includes an inlet 181 and outlet 182 for introducing and withdrawing the polymer solution, bonding pads 190 for providing electric connectivity for the electrodes, and etching hole 185 for etching the photoresist, as will be further described in connection with FIG. 4.

Figure 3A:
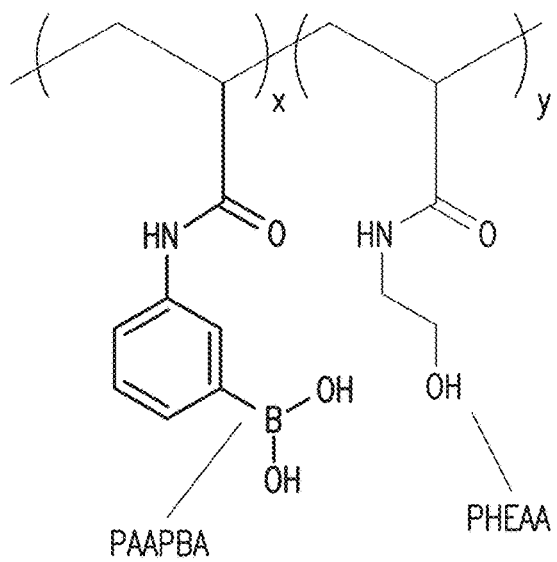
FIG. 3A is a diagram showing the composition of Poly (N-hydroxyethylacrylamide-ran-3-acrylamidophenylboronic acid) (PHEAA-ran-PAAPBA), a glucose-sensitive polymer.
Figure 3B:
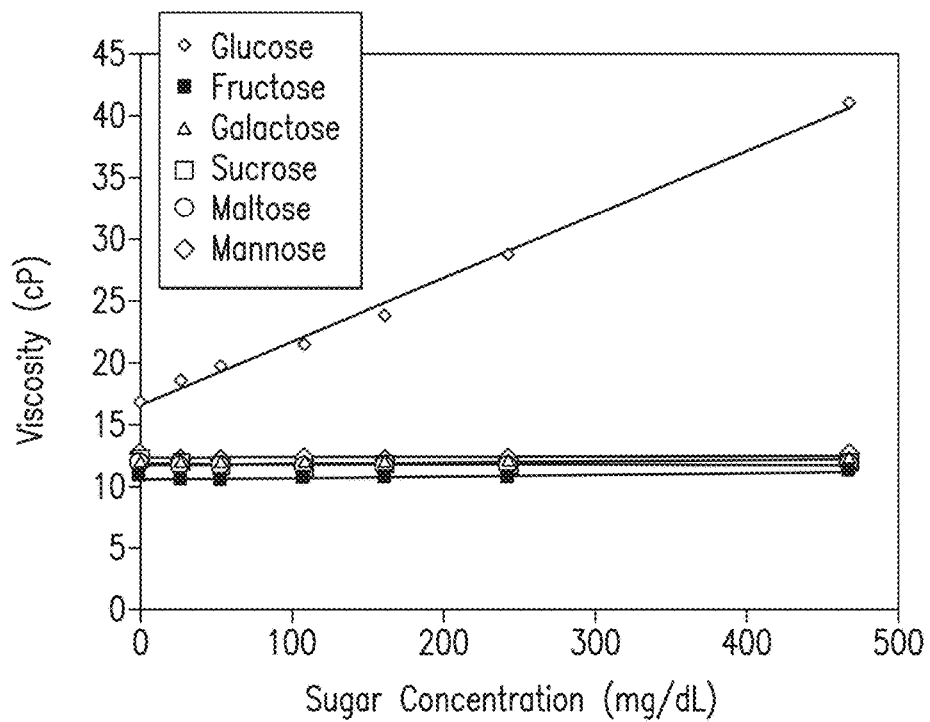
FIG. 3B is a plot illustrating the specificity of the polymer shown in FIG. 3A toward glucose in the presence of other sugars.

The glucose sensitive polymer PHEAA-ran-PAAPBA utilized in the device is a synthetic polymer that recognizes glucose by specific affinity binding. Specifically, PHEAA-ran-PAAPBA is an amphiphilic copolymer containing two components: PAAPBA and poly(N-hydroxyethyl acrylamide) (PHEAA) (FIG. 3A). PAAPBA is a hydrophobic glucose-sensitive component, while PHEAA is a hydrophilic and nonionic component, and primarily serving to improve the overall water solubility of the entire copolymer. When added to an aqueous solution of PHEAA-ran-PAAPBA, glucose binds reversibly to the phenylboronic acid moieties in the PAAPBA segments to form strong cyclic boronate ester bonds, resulting in an increase in the viscosity of the solution (FIG. 3B), while having almost no response to other potential interferents, such as fructose, galactose, and sucrose. Glucose-unresponsive PAA is used as a reference polymer. The viscosity of PAA solution is glucose-independent.

Figure 4A:
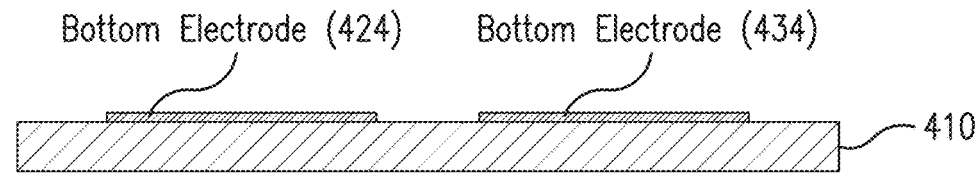
Figure 4B:
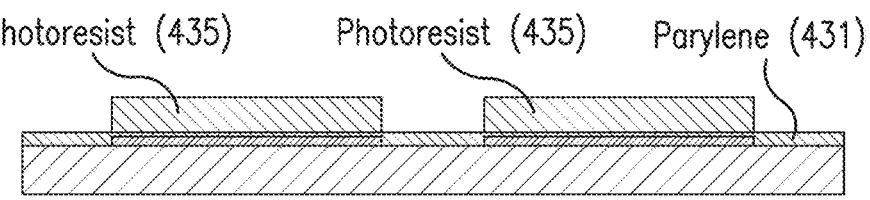
Figure 4C:
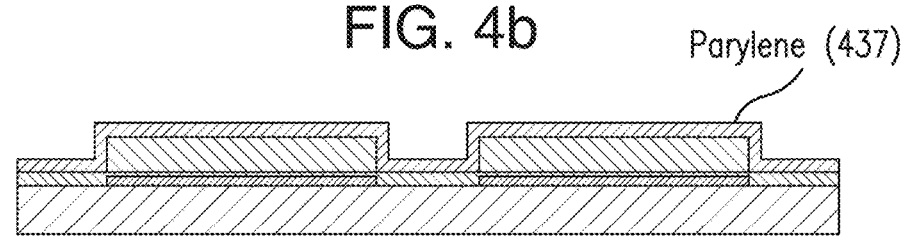
Figure 4D:
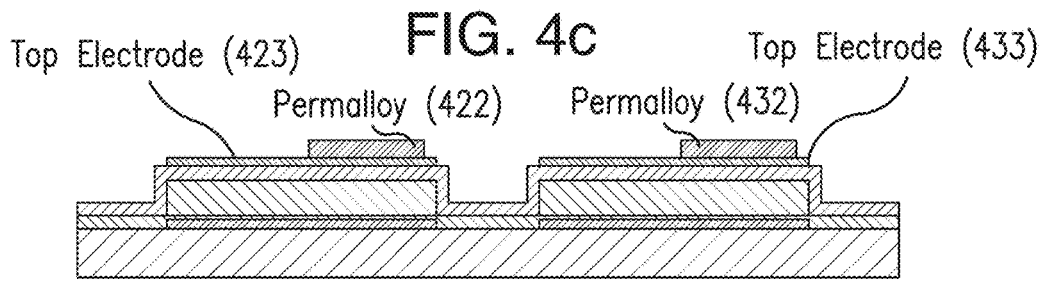
Figure 4E:
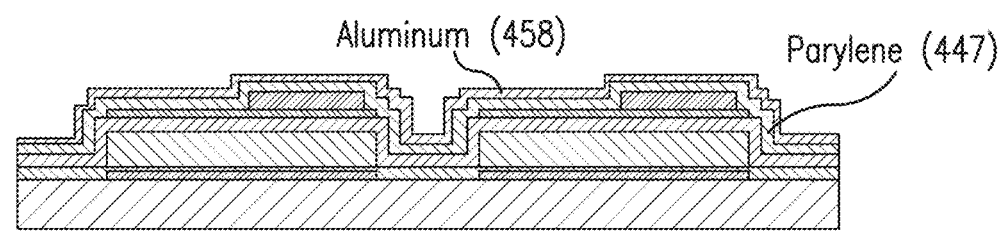
Figure 4F:
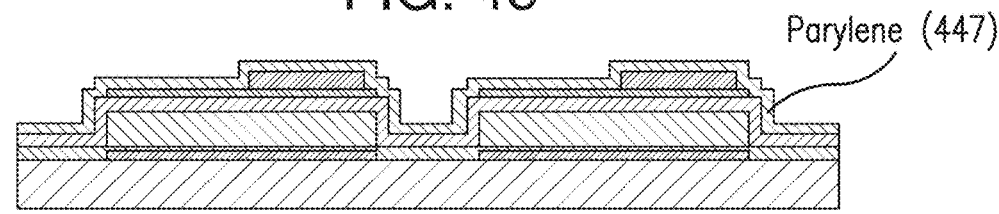

To fabricate the device as shown in FIGS. 1A and 2, chrome (5 nm) and gold (100 nm) were first deposited and patterned to form two electrodes 424 and 434 (500 μm×500 μm) on a $SiO_2$ coated silicon wafer 410 (FIG. 4A), followed by the deposition of a parylene passivation layer 431 (1 μm in thickness). A sacrificial photoresist layer 435 (5 μm) was then spin-coated and patterned to define electrode air gaps (FIG. 4B), followed by the deposition of an additional parylene layer 437 (1 μm in thickness) (FIG. 4C). A second layer of chrome (5 nm) and gold (100 nm) were next deposited for the top electrodes 423 and 433 and Permalloy seed layer. Subsequently, defined by a photoresist pattern (5 μm in thickness), strips of Permalloy 422, 432 (220×35×3 μm) were electroplated (FIG. 4D). This was followed by removal of the photoresist, patterning of the top electrodes (500×500 μm), and deposition of an additional parylene passivating layer 447 (3 μm) and an aluminum mask (458). Eight etching holes (250×250 μm) were opened through the parylene layers and reactive ion etching to expose the sacrificial photoresist (FIG. 4E), which was then removed by acetone (80° C.) to release the diaphragms (520×520 μm) (FIG. 4F). These etching holes were then sealed by epoxy (Devcon Inc.). After wafer dicing (FIG. 5) and wire bonding, a chip was bonded to an SU-8 sheet (thickness: 80 μm), in which holes (1 mm in diameter) of appropriate sizes were patterned to define the microchambers (0.06 μL in volume) as well as the inlets and outlets for the polymer solution handling. This SU-8 sheet was in turn bonded using epoxy to a regenerated cellulose acetate semi-permeable membrane (Membrane Filtration Products, Inc.) with a suitable thickness (for example 20 μm) and a suitable molecular weight cutoff (e.g., 6000 Da).

Chemicals and reagents used in the example include PHEAA-ran-PAAPBA and PAA, which were synthesized in house by free radical polymerization, as described, for example, in Li S, et al., "Synthesis and development of poly(N-hydroxyethyl acrylamide)-ran-3-acrylamidophenylboronic acid polymer fluid for potential application in affinity sensing of glucose." J Diabetes Sci Technol 5:1060-1067 (2011). D-(+)-glucose were purchased from Sigma-Aldrich. PBS, pH 7.4, was prepared by diluting a Ringer's stock solution (Nasco Inc.) with sterile water (Fisher Scientific) at a ratio of 1:9.

To prepare the sensing polymer solution, 284 mg of PHEAA-ran-PAAPBA with an hydroxyethylacrylamide (HEAA) to AAPBA molar ratio of 20 (or approximately 5% of PAAPBA content in the polymer) and a molecule weight of 188,600, was dissolved in 6 mL of PBS, while the reference polymer solution was prepared by dissolving 142 mg of PAA in PBS (6 mL). Glucose stock solution (1 M) was prepared by dissolving glucose (180 mg) in PBS to 10 mL. A series of glucose concentrations (60, 90, 180, 360, and 500 mg/dL) were prepared by further diluting the stock solution with PBS.

During testing, the microchambers were filled with solutions of PHEAA-ran-PAAPBA and PAA, respectively. To facilitate in-vitro device characterization, a test cell (volume: 300 μL) was constructed from an acrylic sheet directly above the MEMS sensor. A glucose solution at a given concentration was introduced into the test cell, where it was allowed to permeate through the semi-permeable membrane of the sensor to interact with PHEAA-ran-PAAPBA in the sensing chamber. Because the volume of the test cell was 5000 times larger than the microchambers, it was reasonable to assume that the glucose concentration inside the microchambers equalized to the given glucose concentration in the test cell when the glucose permeation reached an equilibrium.

FIG. 6 is an exemplary setup for characterization of the MEMS differential glucose sensor. The diaphragm vibrations were excited and measured using the setup in both the in-vitro and in-vivo tests. A cylindrical magnet 610 attached perpendicularly to the shaft 615 of a brushless DC motor 620 (Anaheim Automation) powered by power supply 630. The cylindrical magnet 610 can be spun with a maximum rated speed of 4000 RPM. The motor shaft 615 is parallel to the plane of the MEMS sensor 100 and perpendicular to the Permalloy strips in the sensor, which were hence subjected to an AC magnetic field, inducing the vibration of the diaphragms. The average diaphragm vibration amplitudes were measured by a capacitance digital converter (CDC) 640 which is coupled with the MEMS sensor 100 and also communicates with a computer 650. The CDC used herein was Σ-Δ CDC (Analog Devices, AD7746), which converted the amount of charges on the sensor electrodes to a capacitance value. The CDC is capable of measuring a capacitance change of ±4 pF with a measurement resolution and accuracy at 4 aF and 4 fF, respectively. To measure the differential capacitance, the CDC applied an AC excitation voltage to the fixed electrodes of the sensing and reference diaphragms, while the moving electrodes in the diaphragms were connected to the C+ and C− pins of the CDC, respectively. The capacitances of the sensing and reference electrodes at rest were 81.5 and 63.5 pF, respectively, both of which were beyond the measurement range of the CDC. As a result, the nominal excitation voltage of the CDC (3.3 V) was trimmed to accommodate the measurement range (±4 pF).

The device temperature was uncontrolled throughout the tests, except for the characterization of device temperature stability, in which the device was varied among physiological temperature via closed-loop temperature control. In in-vivo testing, the sensor was implanted in the subcutaneous tissue of a sedated mouse whose glucose concentration was controlled by glucose and insulin injections. The implanted glucose sensor continuously measured the glucose level in ISF, while a commercial glucometer (Freestyle Lite®) sampled blood sugar levels in the mouse's tail at specified frequencies.

Sensor Response to Glucose at Physiological Relevant Concentrations

Sensor response to various glucose concentrations was investigated to characterize the device resolution in glucose detection. The differential diaphragm vibration was measured at physiologically relevant glucose concentrations while the magnet spun at a fixed frequency of 13 Hz. As the glucose concentration changed from 0 to 500 mg/dL, the differential capacitance of the device decreased steadily from 28 to 27.4 pF, reflecting a decrease in the difference of the diaphragm vibration amplitudes and an increase in the viscous damping due to glucose binding with PHEAA-ran-PAAPBA (FIG. 7). The device resolution is, thus, determined to be approximately 0.003 mg/dL with a measuring accuracy of 3.3 mg/dL, which is sufficient for implantable glucose sensors. In addition, the results exhibit increased time constants at higher glucose concentrations. This can be caused by the increase in the viscosity of the polymer solution, which slowed down the glucose diffusion. Sensor capacitance was also observed to become saturated at high glucose concentrations. As a result the relation between glucose concentrations and the differential capacitance is nonlinear and can be represented by a quadratic equation. As the sensitivity of glucose sensors typically changes after implantation, the relation obtained in-vitro is only qualitative for in vivo sensor calibration. The glucose response of the device has demonstrated that the device can detect physiologically relevant glucose concentrations and can be used in implantable glucose monitoring.

The sensor was also exposed to glucose solutions whose concentrations were changed back and forth between two different values to characterize the device time responses. For example, glucose concentration was initially allowed to be equilibrated at 60 mg/dL in the test cell and microchambers. Next, the solution in the test cell was replaced with another glucose solution at 90 mg/dL. When the glucose concentration inside the microchambers had equilibrated to 90 mg/dL, the reverse process was initiated, in which the test cell was refilled with a 60 mg/dL glucose concentration. The process of solution refilling of the test cell (within 10 seconds) was sufficiently fast as compared to the glucose concentration equilibration. During the equilibration processes, the differential sensor capacitance, at a fixed frequency of 13 Hz, was measured as a function of time.

The result of the time response measurement is shown in FIG. 8. As the glucose concentration varies from 60 to 90 mg/dL, the differential sensor capacitance decreases with time, corresponding to a decrease in the sensing diaphragm vibration amplitude as well as an increase in the viscous damping to the diaphragm vibration. The capacitance finally saturates to a constant level, reflecting that the process of glucose permeation and binding have reached a dynamic equilibrium. Considering the glucose concentration change as a step input, the time constant of system's step response is determined to be approximately 1.48 minutes. In the reverse process, the glucose concentration in the test cell is decreased from 90 to 60 mg/dL. The sensor capacitance increases with time, indicating an increase in the vibration amplitude of the sensing diaphragm due to the reduced viscous damping. The time constant for the reverse process is approximately 2 minutes. The longer reverse time constant could be due to the smaller diffusivity of glucose molecules in the initially more viscous polymer solution. Time constants at other glucose concentrations can be obtained from FIG. 7, in which an average time constant of approximately 3 minutes is observed. Note that these time constants compare favorably with response times of commercially available systems, which range from 5 to 15 minutes.

The reversibility of the device response can be obtained by comparing differences in sensor output between two separated measurements at the same glucose concentration. For example, as shown in FIG. 8, the sensor output varies from 27.642 (averaged between 0 and 7 minutes) to 27.485 pF (averaged between 12 and 27 minutes) as the glucose concentration varies from 60 to 90 mg/dL. The sensor output then returns to 27.636 pF (averaged between 32 and 36 minutes) when the glucose concentration is reversed to 60 mg/dL. The difference between the average sensor outputs over the two periods with the glucose concentration at 60 mg/dL is only about 6 fF, or 217 ppm. Note that this reversibility is achieved without temperature control, and is acceptable for implantable applications.

The time constant of the device can be effectively represented by glucose diffusion time in the sensing microchamber, which can be assessed by a simulation using COMSOL Multiphysics with a simplified device model as depicted in FIG. 9 at different initial glucose levels and various glucose concentration changes. As shown in FIG. 9, a diaphragm sealed inside a microchamber by a semi-permeable membrane has been considered as a two-dimensional rectangular region, which contains four walls labeled from 1 to 4. Among them, wall 1 and wall 4 separated by a distance of 80 μm represent the membrane and the sensor diaphragm respectively. And wall 2 and wall 3 are considered sidewalls of the microchamber separated by a distance of 1 mm. The resultant area represents the microchamber filled with a PHEAA-ran-PAAPBA polymer solution at various glucose concentrations. The glucose diffusion coefficient in water is selected to be $7 \times 10^{-10}$ m$^2$/s, which can be used to determine other constants in the Einstein-Stokes equation: $D_g = k_B T / (6 \pi \eta r)$, where $D_g$ is the glucose diffusion coefficient. $k_B$ is the Boltzmann's constant. T is the absolute temperature. η is the viscosity of the polymer solution and r is the radius of the glucose molecule.

Simulated device time responses was first obtained when the glucose concentration changes from 60 to 90 mg/dL and then reserves back to 60 mg/dL. In the simulation, the glucose concentration at wall 1 is fixed at 90 mg/dL, while the rectangular region has an initial glucose concentration of 60 mg/dL. In the reverse process, the glucose concentration at wall 1 is fixed at 60 mg/dL, while the initial glucose concentration in the rectangular region is 90 mg/dL. The time-dependent glucose concentration on wall 4 was obtained as shown in FIGS. 10 and 11. The time constants for the glucose increase and decrease processes are 1.67 and 1.99 minutes, respectively. The simulation results correctly predict the order of magnitude of the time constants determined from the test data. In particular, these results indicate that a large time constant in the reverse process, which is consistent with these measurements.

The same simplified device model also allows for simulation of the device time responses to other glucose concentration changes, as have been presented in FIG. 7. The glucose concentrations in the sensing microchamber are initially at 0, 60, 180, and 360 mg/dL, respectively, and then gradually approach the glucose concentrations at wall 1 that are correspondingly fixed at 60, 180, 360, and 500 mg/dL, respectively. The time constants of these processes are determined by simulation to be 1.3, 1.7, 2.3, and 3.3 minutes, respectively, which are consistent with measured results (FIG. 7).

The ability of the device to resist the temperature variations was also characterized. The temperature of the device was altered from 34 to 40° C. under a closed-loop controlled heating system at a fixed glucose concentration of 60 mg/dL. Both the differential capacitance and single-module capacitance were obtained (FIG. 12). As the device temperature changed by 6° C., the differential and the single-module capacitance changed by 0.8 and 2.72 pF, respectively, indicating that the differential measurements effectively compensated the interference from the temperature variations. The compensation effect of differential measurements to temperature variations can be only partial, as the sensing and the reference diaphragm can respond to temperature changes differently. However, in reality, much smaller and slower temperature variations can be expected in in-vivo applications.

The glucose-independent drift in differential and single-module sensor capacitance was assessed at a fixed glucose concentration without controlling the temperature. The sensor was exposed to a 60 mg/dL glucose solution over an extended period about 5 hours (FIG. 13). During this period, the CDC was programmed to record the differential and the single-module capacitance alternatively under the same environmental conditions (e.g., temperature variations, lighting, and osmotic pressure). It was observed that the drift in differential sensor capacitance was significantly smaller than the single-module capacitance. The differential capacitance of the sensor changes from 27.24 to 27.23 pF (measured at 0 and 320 minutes respectively), indicating a drift at approximately 1.8 fF/hour, while this value becomes 94 fF/hour in the single-module measurements. The large drift in the single-module measurements is probably caused by the temperature variations and osmotic pressure, which are largely compensated in the differential measurements. These results demonstrate that this differential device is capable of compensating for environmental disturbances and providing excellent stability, which is ideal for long-term implantable CGM.

In-vivo characterization of the device was performed with a laboratory mouse. The glucose sensor was implanted in the subcutaneously tissue of a sedated lab mouse to measure the glucose concentration in ISF continuously (FIG. 14A), while a commercial glucometer sampled the glucose level in the capillary blood from the tail tip of the mouse every 10 minutes after glucose injection and every 5 minutes after insulin intervention. FIG. 14B shows the measurement data, which are given in terms of the change of the differential capacitance, calculated with respect to the value at the time of the first glucometer reading. It can be seen that this device output closely follows the commercial glucometer readings as the mouse's blood sugar levels vary over a 3-hour period. This result indicates consistency between the sensor output and the glucometer reading, and supports use of this glucose sensor for long-term CGM.

The differential sensor capacitance ($C_{out}$) was calibrated to obtain estimated blood glucose values ($\hat{G}_1$). A quadratic equation was used to represent the relation between $G_{out}$ and ISF glucose concentrations ($G_2$). Here, $G_2$ can be expressed by $C_{out}$ as $$G_2 = aC_{out}^2 bC_{out} + c \tag{1}$$

where a, b, and c are constants that can be determined from $G_2$ and $C_{out}$. Due to the mass transfer of glucose, a physiological time lag of the concentrations between the ISF glucose and the blood glucose exists. The kinetics of glucose concentrations in blood ($G_1$) and ISF ($G_2$) can be expressed as $$dG_2/dt = -(k_{02} + k_{12})G_2 + k_{21}V_1/V_2 G_1 \tag{2}$$

where $k_{12}$ is the flux rate for forward glucose transport across capillaries and $k_{21}$ is the flux rate for reverse glucose transport across capillaries. $k_{02}$ is the glucose uptake into subcutaneous tissues. $V_1$ and $V_2$ are volumes of the blood and the ISF respectively. $k_{12}$, $k_{21}$, $k_{02}$, $V_1$, and $V_2$ are all constants. The combination of equation (1) and (2) yields $$G_1 = a_1 C_{out}^2 + a_2 C_{out} + a_3 dC_{out}^2/dt + a_4 dC_{out}/dt + a_5 \tag{3}$$

where $a_1$, $a_2$, $a_3$, $a_4$, and $a_5$ are constants that can be determined by partial least squares fitting using six blood glucose values ($G_1$) from glucometer and their corresponding $C_{out}$ from the implanted sensor. After the determination of $a_1$, $a_2$, $a_3$, $a_4$, and $a_5$, the estimated glucose value $\hat{G}_1$ can be obtained using equation (3) with the known $a_1$, $a_2$, $a_3$, $a_4$, $a_5$, and $C_{out}$.

The clinical accuracy of the $\hat{G}_1$ as compared to $G_1$ can be quantified using a Clarke error grid, which has been divided into several zones (e.g., A, B, C, D, and E) to represent different levels of accuracy. For example, if a point falls into Zone A or Zone B, the measurement is either clinically accurate or clinically acceptable. In contrast, if a point falls into another zone, then that the measurement might lead to problems, such as overcorrection, dangerous failure, and erroneousness. In these measurements, all points in the Clarke error grid exclusively fall into Zone A (95.3%) and Zone B (4.7%), while no point falls into other zones (FIG. 15). These results indicate a good clinical accuracy of the measurements, showing a great promise to apply this affinity sensor for long-term in-vivo glucose monitoring.

The results as described in connection with FIGS. 7-15 in this Example establish that the sensor experienced a decrease in the differential capacitance of approximately 0.6 pF when the glucose concentration increased from 0 to 500 mg/dL. The time constant of the sensor was approximately 1.48 minutes during a glucose concentration change from 60 to 90 mg/dL. The sensor also exhibited excellent reversibility; the differential capacitance of the sensor measured at two separated measurements at 60 mg/dL glucose concentration agreed within 99.97%.

In addition, by varying the device temperature from 34 to 40° C. at a glucose concentration of 60 mg/dL, the differential capacitance changed by 0.8 pF, which is at least three times smaller than the change in the single-module capacitance, indicating the sensor's ability in resisting temperature variations. By exposing the sensor to a 60 mg/dL glucose concentration for an extended measurement period of 5 hours, the differential sensor output exhibited low drift (1.8 fF/h), which is appropriate for long-term, stable CGM. Moreover, the results as described in connection with FIGS. 14-15 indicate that the sensor output closely follows blood glucose concentrations in laboratory mice as measured by a commercial glucometer. Clarke error grid analysis using the calibrated in-vivo sensor data (FIG. 15) have demonstrated the clinically accuracy of the sensor measurements.

Example 2: A Dielectric Affinity Sensor

U.S. Patent Application Publication No. 20120043203 discloses a dielectric CGM sensor that has no moving structure, and thus can be stable in face of environmental disturbances. In this example, a dielectric glucose sensor with a perforated electrode is described. The change in permittivity in the polymer solution as a result of glucose-polymer binding can be measured from the capacitance of the capacitor formed between the electrodes. Results from in-vitro characterization of this sensor as described in FIGS. 20-26 demonstrate that this dielectric sensor can be useful in CGM.

FIG. 16 shows a schematic diagram of a single-module MEMS dielectric glucose sensor used in this Example. The sensor includes a microchamber 1601 filled with a glucose-sensitive polymer solution 1650 and sealed by a semi-permeable membrane 1615. A perforated electrode 1623 embedded in a diaphragm 1630 is separated from a bottom electrode 1624 (which also can be perforated) on a substrate 1610 below by the polymer solution 1650. Environmental glucose 1670 that permeates through the semi-permeable membrane binds with the polymer and changes the permittivity of the polymer solution. As the polymer solution can permeate through the top perforated electrode 1624, it can fill the gap between the perforated electrode 1624 and substrate 1610. The anti-stiction posts 1638 can support the diaphragm 1630 and prevent the diaphragm from collapsing while providing additional resistance to environmental disturbances (e.g., shock, vibration, etc.)

The perforated electrode 1623 embedded in the diaphragm 1630 forms a parallel plate capacitor with the passivated bottom electrode 1624 on the substrate. The glucose-sensitive polymer used here was PAA-ran-PAAPBA, which interacts with glucose by specific affinity binding as described in U.S. Patent Application Publication No. 20120043203. In brief, when added to an aqueous solution of PAA-ran-PAAPBA, glucose binds reversibly to phenylboronic acid moieties in AAPBA segments to form strong cyclic boronate ester bonds, resulting in a change in the permittivity of the dielectric solution as well as a change in the sensor capacitance.

In an electric field, a number of polarization mechanisms contribute to the permittivity of the polymer solution as well as the measured sensor capacitance. These polarization effects are time-dependent in a harmonic electric field, and are influenced by the polymer molecular structure. The solution of PAA-ran-PAAPBA can undergo a molecular structure change when the polymer binds to the glucose. Thus, at a given frequency, the permittivity can change, which can be measured to determine the glucose concentration. The permittivity of the polymer solution is a complex and can be written as $\varepsilon^* = \varepsilon' - i\varepsilon''$, in which the capacitive component $\varepsilon'$ represents the ability of the polymer solution to store the energy from the electric field, while the resistive component $\varepsilon''$ is related to energy loss. As $\varepsilon'$ is directly proportional to the device capacitance ($C_x$), any changes in $\varepsilon'$ can be determined from capacitance measurements.

The fabrication of the device started with deposition and patterning of a thin film gold layer to form a bottom electrode (1 mm×1 mm×100 nm) as well as a resistive temperature sensor on a $SiO_2$ 1711 coated silicon substrate 1710 (FIG. 17A). A parylene passivating layer 1731 (1 µm in thickness) was then deposited by chemical vapor deposition. Following the spin-coating and patterning of a sacrificial photoresist layer 1735 (3 µm in thickness) (FIG. 17B), an additional parylene layer 1737 (1.5 µm in thickness) was deposited. A gold layer was further deposited and patterned to form a perforated electrode 1733 (FIG. 17C), which was then passivated by another parylene layer 1738 (3 µm in thickness) (FIG. 17D) and a patterned SU-8 reinforcement layer 1739 (20 µm in thickness) (FIG. 17E), resulting in nine anti-stiction posts 1748 with diameters of 50 µm. A SU-8 layer 80 µm in thickness was finally spin-coated and patterned to form microchamber wall 1733 as well as an inlet and an outlet for polymer solution handling. The two successively coated SU-8 layers also acted as a mask for patterning of the underneath parylene layers by reactive ion etching to expose the sacrificial photoresist layer, resulting in a diaphragm with holes for glucose diffusion. The diaphragm was at last released by removal of the sacrificial layer in a photoresist stripper. A cellulose acetate semi-permeable membrane 1715 (Membrane Filtration Products, Inc) was in turn glued onto the microchamber 1701 (FIG. 17F) by epoxy (Decvon Inc). The sensor was encapsulated into an acrylic test cell with a total volume of approximately 1 mL. FIG. 18 shows images of the sensor before packaging.

The PAA-ran-PAAPBA polymer was synthesized in house by free radical polymerization (see S. Li et al., "Development of Novel Glucose Sensing Fluids with Potential Application to Microelectromechanical Systems-Based Continuous Glucose Monitoring," *Journal of Diabetes Science and Technology*, 2: 1066-1074, (2008); S. Li, et al., "Development of Boronic Acid Grafted Random Copolymer Sensing Fluid for Continuous Glucose Monitoring," *Biomacromolecules*, 10: 113-118, (2008)). To prepare the polymer solution, 284 mg of PAA-ran-PAAPBA, with an AA to AAPBA molar ratio of 20 (or approximately 5% PAAPBA content in the polymer) and a molecule weight of 170,700, was dissolved in 6 mL of phosphate buffer saline (PBS). The PBS buffer, pH 7.4, was prepared by diluting a Ringer's stock solution (Nasco) with sterile water (Fisher Scientific) at a ratio of 1:9. D-(+)-glucose was purchased from Sigma-Aldrich. Glucose stock solution (1 M) was prepared by dissolving glucose (1.8 g) in PBS to 10 mL. A series of glucose solutions (30 mg/dL, 60 mg/dL, 90 mg/dL, 120 mg/dL, 240 mg/dL, and 480 mg/dL) were prepared by further diluting the stock solution with PBS.

The microsensor was characterized using the setup shown in FIG. 19. In FIG. 19, the MEMS sensor 100 was integrated into a capacitance/voltage transformation circuit driven by a sinusoidal input from a function generator 1910 (Agilent, 33220A). The sensor is also coupled with a multimeter 1920 for outputting measurement result. The temperature of the polymer solution in the MEMS sensor 100 was maintained at 37° C. via closed-loop control by a Peltier heater 1970 (Melcor, CP14) powered by power supply 1930. The voltage of the Peltier heater 1970 is also controlled according to the feedback from the on-chip temperature sensor. Further details of FIG. 19 can be found in X. Huang, et al., "A Dielectric Affinity Microbiosensor," *Appl. Phys. Lett.*, 96: 033701-033703, (2010). All tests were conducted at frequencies below 100 kHz as allowed by a lock-in amplifier 1950 (Stanford Research Systems, SR830), which measured the amplitude and the phase shift of the output voltage from the circuit, and communicates with the computer 1940. The equivalent capacitance ($C_x$) that is directly related to the polymer permittivity was determined from the circuit outputs when the MEMS sensor 100 and a reference capacitance 1980 ($C_R$) are in turn coupled into the circuit by switching T between position S and R.

The device glucose response was measured under an E-field at a range of driving frequencies. The device's equivalent capacitance as a function of frequency for the glucose-free PAA-ran-PAAPBA polymer solution was first obtained. As shown in FIG. 20, the sensor capacitance decreases consistently with the frequencies due to the frequency-dependent dielectric relaxation of the polymer. In addition, a rapid decrease of sensor capacitance from 72.7 to 20 pF was also observed with the frequency changed from 5 to 20 kHz. This can be attributed to interfacial polarization, which typically dominates at low frequency. By exposing the device to various glucose concentrations ranging from 30 to 480 mg/dL, the sensor capacitance decreases with increasing glucose concentrations at all measured frequencies (FIG. 21). For example, at 100 kHz frequency, the sensor capacitance decreases by 0.3 pF at 480 mg/dL with respected to the sensor capacitance in the glucose-free polymer solution. These results suggest that the glucose concentration can be determined through permittivity measurement at a fixed frequency (e.g., 100 kHz).

The glucose-dependent permittivity or capacitance changes of the device can be attributed to a number of polarization mechanisms, such as electronic polarization, ionic polarization, dipolar reorientation, counterion polarization, and interfacial polarization. First, the electronic polarization and the ionic polarization are referred to the distortion of electron cloud and displacement of ions in the applied E-field, respectively. Second, the dipolar reorientation involves alignment with the applied E-field of permanent dipoles, which, for PAA-ran-PAAPBA, can include AAPBA and AA segments rigidly attached to the polymer backbone. Third, in the counterion polarization, appending groups of PAA-ran-PAAPBA are negatively charged, and cations (e.g., $Na^+$, $K^+$, and $H_3O^+$) are attracted to form a counterion cloud. Under the E-field, the counterions migrate unevenly within the cloud to contribute a net dipole moment.

The interfacial polarization involves dipole moments due to electrical double layers formed at the interfaces of the ionic buffer with polymer molecules (i.e., Maxwell-Wagner-Sillars polarization) as well as the passivated electrode surfaces (electrode polarization). These interfacial polarization effects dominate the low-frequency regions, and are generally exhibited as a sharp decline of permittivity with increasing frequencies. The relaxation frequency of electronic and ionic polarization is on the order of 1 THz, and interfacial polarization is on the order of 1 GHz, while those of dipole reorientation and counterion polarization are on the order of a few kHz to a few tens of kHz. Thus, all of these polarization mechanisms can be significant for the polymer, and the relaxation behavior apparent from the rapid drop of the measured capacitance at frequencies lower than 20 kHz (FIG. 20) can be mainly due to the interfacial polarization.

At the above measurement frequencies, the polarization behavior of PAA-ran-PAAPBA is influenced by glucose binding. As AAPBA segments bind with glucose at a two to one ratio to form cyclic esters of boronic acid by eliminating two hydroxyl groups. This can cause a decrease of net permanent dipole moments, thereby reducing the energy storage ability of the polymer solution as well as the capacitive component ($\varepsilon'$) in the permittivity. Furthermore, glucose binding can lead to variations in the net charge of polymer segments as well as changes in the polymer conformations, which would alter the electric double layer structure and result in changes in Maxwell-Wagner-Sillars and counterion polarization. Moreover, the crosslinking of polymer after glucose binding can increase the elastic resistance of the permanent dipoles in polymer to alignment with the E-field, leading to a decrease in $\varepsilon'$. The combination of these effects explains that at a given frequency, the measured sensor capacitance decreased with glucose concentrations (FIG. 21).

To characterize the device time response, the glucose concentration was allowed to be equilibrated at 60 mg/dL in the test cell and the microchamber. Next, the solution in the test cell was replaced with another glucose solution at 120 mg/dL. When the glucose concentration inside the sensor chamber had equilibrated to 120 mg/dL, the reverse process was initiated, in which the test cell was refilled with a glucose solution at 60 mg/dL again. The process of glucose sample introduction was typically within a few seconds, which was sufficiently fast when compared with the time for the glucose concentration equilibration. Throughout this concentration equilibrium process, an AC voltage of a fixed frequency of 100 kHz was applied to the sensor, and the sensor capacitance changes at this frequency were obtained.

From the data (FIG. 22), it can be seen that as the glucose concentration varies from 60 to 120 mg/dL, the sensor capacitance decreases with time, corresponding to a decrease in the permittivity of the polymer solution due to glucose binding. The sensor capacitance finally saturates to a constant level, reflecting that the process of glucose permeation and binding have reached a dynamic equilibrium. Assume that the glucose concentration change as a step input, the time constant of the device represents the time it takes the system's step response to reach 63.2% of its final value. The time constants for the forward and reverse processes are approximately 2.49 and 3.08 minutes respectively. The longer reverse time constant could be due to the smaller diffusivity of glucose molecules in the initially more viscous polymer solution and have been confirmed by the simulation in Example 1.

The reversibility of the device response can be obtained by comparing differences in sensor output between two separated measurements at the same glucose concentration. For example, as shown in FIG. 22, the sensor capacitance at 60 mg/dL glucose concentration varies from 11.951 (averaged over the period between 0 and 5 minutes) to 11.952 pF (averaged over the period between 26 and 31 minutes). The difference between the average sensor outputs over the two periods with the glucose concentration at 60 mg/dL is only about 1 fF, indicating that the sensor possesses excellent reversibility with respect to glucose concentration variations.

The drift of the device was investigated by exposing it to a constant glucose concentration (60 mg/dL) over an extended measurement period. The sensor capacitance at 100 kHz is shown in FIG. 23. It can be seen that the sensor capacitance is steady at 11.955 pF over a period of about 4 hours with slight drift. The low drift demonstrates that the device can offer highly stable measurements for long-term continuous glucose monitoring. However, some fluctuations during the measurement were also observed, which can be explained as the environmental disturbances, such as shocks, vibrations, and human activities, which randomly appear in the testing environment.

Example 3: Another Dielectric Affinity Sensor

In this example, the affinity sensor discussed in Example 2 is used, except that the polymer in the sensing chamber was changed to poly(N-hydroxyethyl acrylamide)-ran-3-acrylamidophenylboronic acid (PHEAA-ran-PAAPBA). Similar studies were performed on the frequency dependence of the sensor response, time response and drift of the sensor. FIG. 24 shows that in the absence of glucose, the sensor capacitance decreased monotonically from 0.5 to 20 kHz, and then increased slowly at higher frequencies where orientational polarization was significant. FIG. 25 shows the sensor's time response assessed at a fixed frequency of 100 kHz. In response to a step glucose concentration change from 50 to 100 mg/dL, the sensor showed a time constant of 4.7 minutes, which is acceptable for CGM and further improvable by optimizing the sensor geometry. The drift of the sensor over time is very small, as shown in FIG. 26.

Example 4: A Differential Dielectric Affinity Sensor

In Examples 2-3, glucose sensors based on permittivity detection are discussed. Each of these devices contains a single sensing element that measures the glucose-induced permittivity changes in the polymer solutions. The results demonstrate the use of these devices in long-term and stable CGM. However, as the dielectric property of polymer solutions is very sensitive to disturbances, these dielectric sensors require closed-loop temperature control to maintain the device temperature, and exhibit limited resistance to environmental interferences. As a result, noticeable fluctuations of the sensor signal can be observed in the drift measurement (FIG. 23).

Differential sensing has been successfully applied in the development of the viscometric glucose sensor, as illustrated in Example 1, which shows an improved stability in face of common mode disturbances. In this example, a MEMS differential dielectric sensor having two microchambers utilizing permittivity measurement is discussed. The glucose concentration can be determined from the permittivity difference between the sensing and the reference solutions, which is measured as the differential capacitance. The test results in this example as described in connection with FIGS. 29-37 demonstrate that the sensor allows sensitive and specific detection of glucose at physiologically relevant concentrations with improved stability to external interferences, showing a great promise to apply the differential dielectric sensor for fully implantable, long-term CGM.

The structure of this sensor is depicted in FIG. 1B. In brief, this sensor includes a pair of perforated electrodes (123, 133) situated inside a sensing microchamber 101 and a reference microchamber 102, respectively. The sensing chamber 101 contains a solution of a glucose sensitive polymer 160, while the reference chamber 102 is filled with a solution of a reference polymer 160 that is not responsive to glucose. The microchambers 101 and 102 are sealed with a semi-permeable membrane, which prevents the polymers from escaping from the microchambers, while allowing environmental glucose to diffuse through. The perforated electrodes (123, 133) are embedded in suspended diaphragms (120, 130) that are supported by arrays of anti-stiction posts (128, 138). These posts prevent the diaphragms from collapsing, while offering additional support for the diaphragms from environmental disturbances. Each of the perforated electrodes is separated from a bottom electrode (124, 134) by a gap that is also filled with the sensing polymer solution 150 or the reference polymer solution 160, resulting in a capacitor with the polymer solution as dielectrics. As glucose permeates through the semi-permeable membrane into each chamber, the permittivity of the sensing polymer solution is changed due to glucose binding, while the permittivity of the reference solution is unchanged due to a lack of glucose binding. The permittivity difference between the sensing and the reference solution can be determined from differential capacitance, which also allows determination of the glucose concentrations while rejecting permittivity changes caused by environmental fluctuations. The differential sensor uses PHEAA-ran-PAAPBA as glucose sensitive polymer, and PAA as a reference polymer, same as described in Example 1.

Figure 27A:
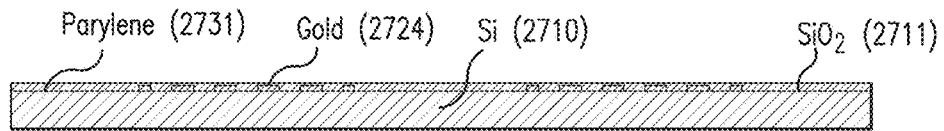
Figure 27B:
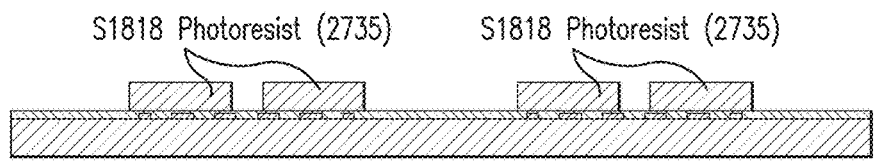
Figure 27C:
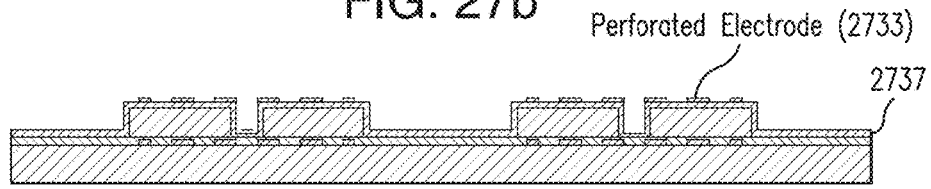
Figure 27D:
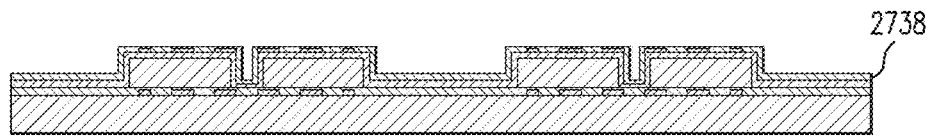
Figure 27E:
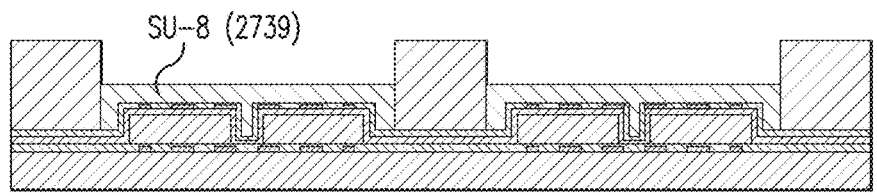
Figure 27F:
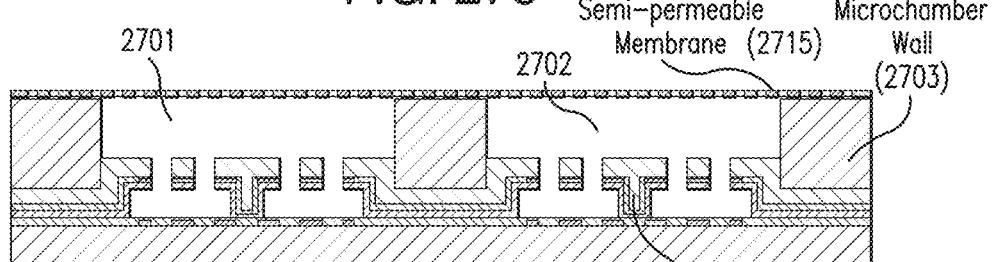

The procedure to fabricate the differential sensor in this example is schematically shown in FIGS. 27A-27F, which are similar to FIGS. 17A-17F (which are for single-module sensor). A thin film gold layer was deposited and patterned to form bottom electrodes 2724 (1 mm×1 mm×100 nm) as well as resistive temperature sensors on a silicon substrate 2710 coated with silicon oxide 2711 (FIG. 27A). A parylene passivating layer 2731 (1 μm in thickness) was then deposited by chemical vapor deposition. Following the spin-coating and patterning of a 5 μm sacrificial photoresist layer 2735 (FIG. 27B), an additional parylene layer 2737 (1.5 μm in thickness) was deposited. A gold layer was further deposited and patterned to form top perforated electrodes 2733 (FIG. 27C), which was then passivated by another parylene layer 2738 (3 μm in thickness) (FIG. 27D) and a succeeding SU-8 reinforcement layer 2739 (20 μm in thickness) (FIG. 27E), resulting in nine anti-stiction posts 2748 with diameters of 50 μm for each perforated electrode. A SU-8 layer 80 μm in thickness was finally spin-coated and patterned to form microchamber walls as well as inlets and outlets for polymer solution handling. The two successively coated SU-8 layers also acted as a mask to pattern the underneath parylene layers by reactive ion etching to expose the sacrificial photoresist layer and form diaphragms with holes for glucose diffusion. The diaphragms were released by the removal of sacrificial layer in photoresist stripper. A CA semi-permeable membrane 2715 (Membrane Filtration Products, Inc) was in turn glued onto the two microchambers 2701 and 2702 by epoxy (Decvon Inc) (FIG. 27F). The differential sensor was encapsulated into an acrylic chamber with a total volume of approximately 1 mL. FIG. 28 shows images of the sensor before and after packaging.

Two setups were used to characterize the device. First, a capacitance/voltage converter circuit similar to what is depicted in FIG. 19 was used to measure the frequency response of both the sensing and the reference polymer. Specifically, this circuit measures the single-module capacitance of the sensing or the reference electrodes under an AC E-filed with an amplitude of 10 mV and a frequency varied from 0.5 to 100 kHz. The amplitude and the phase of the output voltage from the circuit are captured by a lock-in-amplifier (SR830) to calculate the sensor capacitance using previously reported equations. This setup is further simplified using an Σ-Δ CDC (Analog Devices, AD7746), which converts the amount of charges on the capacitive sensor electrodes to a capacitance value. This CDC processes a measurement capacity of ±4 pF in capacitance changes with a resolution at 4 aF and an accuracy at 4 ff. To measure the differential capacitance, the CDC applies a square wave at a frequency of 32 kHz to the bottom electrodes, while the perforated electrodes are connected to capacitance measurement pins of the CDC. The initial capacitances of the sensing and the reference electrodes were determined to be 57.8 and 19.2 pF, respectively, which were beyond the measurement range of CDC. Thus the effective excitation voltage from the CDC was trimmed from a designated value of 3.3 V to an appropriate value to accommodate the measurement range.

The CDC can be programmed to obtain either the capacitance difference of the sensing and the reference electrodes or the single-module capacitance solely from the sensing electrode.

Chemicals and reagents used in the this example include PHEAA-ran-PAAPBA, which was synthesized in house by free radical polymerization with an HEAA to AAPBA molar ratio of 20 (or approximately 5% PAAPBA content in the polymer) and a molecule weight of 188600. PAA was also synthesized by a similar process as PHEAA-ran-PAAPBA using acrylamide monomer. D-(+)-glucose was purchased from Sigma-Aldrich. PBS, pH 7.4, was prepared by diluting a Ringer's stock solution (Nasco) with sterile water (Fisher Scientific) at a ratio of 1:9. PHEAA-ran-PAAPBA (284 mg) and PAA (142 mg) were dissolved in PBS (6 mL) to obtain a sensing and a reference solution, respectively. Glucose stock solution (1 M) was prepared by dissolving glucose (180 mg) in PBS to 10 mL. A series of glucose concentrations (50, 100, 200, 300, 400, and 500 mg/dL) were prepared by further diluting the stock solution with PBS.

Both in-vitro and in-vivo testing was performed to characterize the device. First, the frequency responses of the electrodes with glucose-free sensing and reference solutions were characterized using the capacitance/voltage converter circuit. In addition, the frequency responses of the sensing polymer at selected glucose concentrations were also obtained. The time responses of the sensor upon glucose concentration changes were then obtained using the CDC, which was also used for all the following tests.

The frequency responses of the sensing and the reference electrodes to the E-field with a frequency from 0.5 to 100 kHz were obtained using the capacitance/voltage converter circuit. As shown in FIG. 30, when the polymer solutions contained no glucose, the frequency responses of the sensing and the reference electrodes, which are represented as the capacitances, decrease consistently from 0.5 to 20 kHz and afterwards undergo slow increases. The abnormally decreases of the electrode capacitances at low frequencies could be attributed to effects of electrode polarization and Maxwell-Wagner-Sillars polarization, which typically happen between the interface of two different media and are exhibited as a rapid decrease of permittivity at low frequencies.

The capacitance changes in the sensing electrodes after the binding between glucose and the polymer were also obtained at selected glucose concentrations from 50 to 200 mg/dL. As shown in FIG. 30, the electrode capacitance decreases with increasing glucose concentrations after 10 kHz. In contrast, at frequencies between 0.5 and 10 kHz, the capacitance increases with glucose concentrations. These frequency-dependent sensor responses suggest that the glucose-induced permittivity change through capacitance can be measured at a fixed excitation frequency.

At the measurement frequencies (lower than 100 kHz), a number of polarization mechanisms, such as electronic polarization, ionic polarization, orientational polarization, and interfacial polarization, can contribute to the measured electrode capacitances. The binding between glucose and PHEAA-ran-PAAPBA can involves complex dielectric changes. However, conjectural causes of the glucose-dependent capacitance changes observed in FIG. 30 can occur as follows. First, when glucose permeates through the semipermeable membrane, it interacts with AAPBA segments in PHEAA-ran-PAAPBA at a two to one ratio to form cyclic ester of boronic acid, resulting in the elimination of two hydroxyl groups. This can cause a decrease of the net permanent dipole moments in the polymer solution, thereby reducing the ability of the polymer solution in energy storage and thus the permittivity. Second, glucose binding can lead to variations in the net charge of polymer segments as well as in the polymer conformations, which would alter the electric double layer structure and result in changes in Maxwell-Wagner-Sillars and counterion polarization. Moreover, the crosslinking of polymer after glucose binding can increase the viscoelastic resistance of the permanent dipoles on the polymer backbone to alignment with the E-field, leading to a decrease in the permittivity. As a result, the electrode capacitance exhibited a decrease with glucose concentrations at most of measured frequencies in FIG. 30. Although the underling cause of the crossover of electrode capacitances at a frequency about 10 kHz requires further investigation, it can be possible due to the glucose-induced changes in the interfacial polarization effect.

Time-resolved measurements of the differential capacitance in response to glucose concentration changes were also performed, which allowed for assess the time responses and reversibility of the sensor. For example, the glucose concentration was initially allowed to be equilibrated at 50 mg/dL in the test cell and the microchambers. Next, the solution in the test cell was replaced with another glucose solution at 100 mg/dL. When the glucose concentration inside the microchambers had equilibrated to 100 mg/dL, the reverse process was initiated, in which the test cell was refilled with a glucose solution at 50 mg/dL. The process of solution refilling of the test cell lasted about 10 s, which was sufficiently fast when compared with the glucose concentration equilibration.

From the 1 data (FIG. 31), it can be seen that, as the glucose concentration varies from 50 to 100 mg/dL, the differential sensor capacitance decreases with time, corresponding to a decrease in the permittivity of the polymer solution. The capacitance finally saturates to a constant level, reflecting that the process of glucose permeation and binding has reached a dynamic equilibrium. The time constant of this process was approximately 2.6 minutes. In the reverse process, the glucose concentration in the test cell decreased from 100 to 50 mg/dL. The capacitance increases with time due to an increase of the permittivity of the sensing polymer solution. The time constant of the reverse process was approximately 3.8 minutes. The longer time constant of the reverse process can be due to the smaller diffusivity of glucose molecules in the initially more viscous polymer solution. Note that these time constants are comparable with the response times of commercial systems, which range from 5 to 15 minutes, and can be further improved by shortening the distance between the semipermeable membrane and the electrodes.

The reversibility of the device responses can be obtained by comparing differences in sensor outputs between two separated measurements at the same glucose concentration. For example, as shown in FIG. 31, the differential sensor capacitance varies from 38.633 (averaged over the period between 6 and 11 minutes) to 38.626 pF (averaged over the period between 40 and 50 minutes). The difference between the differential capacitance over the two periods is about 7 fF or 180 ppm. This reversibility was achieved without delicate temperature control as the single-module dielectric sensors, but solely depended on differential measurements to compensate for the environmental disturbances, indicating that the differential dielectric sensor can be applied for long-term, implantable CGM.

The glucose response of the sensor was further assessed by sequentially exposing the device to physiologically relevant glucose concentrations from 50 to 500 mg/dL. The measurement started with glucose-free sensing and reference polymer solutions. After the differential capacitance became stable, glucose solutions at escalated concentrations were quickly introduced into the test cell of the sensor. From FIG. 32, the sensor capacitance decreases steadily with the glucose concentration from 38.88 to 37.74 pF, indicating a measurement resolution of 0.002 mg/dL with an accuracy of 1.75 mg/dL. The differential capacitance was observed to have the tendency to become saturated at higher glucose concentrations. This indicates that the relationships between differential sensor capacitances and glucose concentrations are nonlinear, and can be represented by a quadratic equation, which is useful in the in-vivo sensor calibration.

The drift of the sensor output was investigated by exposing the sensor to 50 mg/dL glucose solution over a long period. During this period, the CDC was continuously switched between the differential and the single-module measurements. From FIG. 33, the differential capacitance is steady at 38.62 pf over a period about 4 h. In contrast, a significant drift about 0.2 pF/h is observed in the single-module capacitance, which varies from 57.68 to 56.9 pF. The drift in the single module measurement is possibly due to environmental variations and osmotic pressure, which have been mostly compensated by the differential measurement. These results indicate that the differential measurement effectively resists the drift in the sensor output and exhibits excellent stability that is suitable for long-term CGM.

The sensor stability in face of sudden temperature variations was obtained in both differential and single-module measurements to demonstrate the ability of the sensor in rejecting temperature fluctuations, which generally exist in in-vivo environments. To simulate the actual implantation environment, the temperature of the device was altered among physiological temperatures under a closed-loop controlled heating system. As can be seen from FIG. 34, the differential sensor capacitance has significantly less change and thus, better temperature stability as compared with the single-module capacitance. As the device temperature is changed from 35 to 40° C., the differential capacitance changes by 0.15 pF, corresponding to a 1.3 pF change in the single-module capacitance. This result indicates that differential measurements effectively compensate the influence from temperature variations. Here, the compensation of the differential measurement is only partial, as the temperature-induced capacitance changes are reduced rather than completely eliminated. This can be explained by the mismatch of the thermal-electric properties between the sensing and the reference polymer and inconsistence during the fabrication of the sensing and the reference electrodes, leading to different capacitive responses upon temperature changes. The temperature stability can be further improved by careful selection of the reference polymer to achieve a similar thermal-electric property as the sensing polymer.

The device was characterized in-vivo with three sedated laboratory mice. FIG. 35A is a picture showing sensor implantation in one such sedated laboratory mouse. The glucose sensors implanted in the subcutaneous tissue of the sedated mice measured the glucose concentrations in ISF continuously, while a commercial glucometer sampled the blood sugar levels in the tail of the mice every 5 minutes.

After sensor implantation, the devices were initiated for 10 to 30 minutes to allow the equilibrium of glucose and saline in microchambers with the environmental ISF. During this process, glucose in the ISF permeated through the semi-permeable membrane and diffused into the polymer solutions, which were originally free of glucose before implantation. Simultaneously, the differences in the saline composition between the polymer solutions and ISF were also eliminated through ion exchanges. An exemplary sensor response for this setup process was shown in FIG. 35B, in which the differential sensor capacitance decreases over time from 0.78 to 0.68 pF, indicating a decrease in the permittivity of the PHEAA-ran-PAAPBA polymer solution due to affinity binding between the glucose and the sensing polymer. The differential capacitance is eventually leveled, indicating the completion of the sensor initialization and the readiness of implantation measurements.

Both the differential sensor outputs and the glucometer readings were recorded after device initialization. During measurements, blood glucose levels were first allowed to be purely managed by the metabolism of the sedated mice without intervention from glucose or insulin injections. The glucose levels of mice were then reduced to hypoglycemia through insulin injections, and, afterward, increased to hyperglycemia via glucose injections. The glucometer readings and the changes of the differential capacitance calculated with respect to the value at the time of the first glucometer reading are shown in FIG. 36 for all tested mice. It can be seen that the device output closely followed the commercial glucometer readings as the blood glucose levels vary over the measurement periods ranging from 90 to 150 minutes. Time lags between the differential capacitance and the glucometer readings when glucose levels undergo rapidly changes exist for all tested mice. The lags, which range from 5 to 15 minutes, depend on individual tested subjects as well as the response times of the tested glucose sensors.

The differential capacitance of the sensor can be calibrated with the reference glucose values obtained from the glucometer using a previously introduced six-point calibration method, as discussed in Example 1. The clinical accuracy of the $\hat{G}_1$ as compared to $G_1$ can be quantified using a Clarke error grid (FIG. 37), which has five zones labeled with letters from A to E, representing different levels of measurement accuracy. All 61 measured points were calibrated and the corresponding $\hat{G}_1$ was obtained. Here, all points fall exclusively fall into Zone A (83.6%) and Zone B (16.4%), whit no point falling into other zones. These results indicate that the differential dielectric sensors achieve clinical accuracy and good consistency with the glucometer.

The test results in this Example demonstrate that this differential dielectric sensor can be used for subcutaneously implanted devices for long-term, stable, and reliable CGM in diabetes management.

Example 5. An Implantable Monitor Including a MEMS Affinity Sensor and a Wireless Interface In this example, active telemetry is used to construct a wireless interface for the implanted glucose sensors. A photograph of a wireless interface 3800 and an external reader 3880 are shown in FIG. 38B. Although the dimension of this wireless interface is still relative large for fully implantable applications, it allows for verification of the feasibility of this wireless interface, and provides a convenient and reliable tool for in-vivo animal studies.

As schematically illustrated in FIG. 38A, the wireless interface 3800 contains a low frequency passive transponder 3810 (Texas Instruments, TMS37157), a microcontroller 3830 (Microchip technology, PIC16LF1829), a CDC 3840 (Analog Devices, AD7746), a voltage regulator (Texas Instruments, TPS76901), and a rechargeable battery 3820. Integrated with a glucose affinity sensor 100, this wireless interface can record and send out a 24 bits sensor capacitance value every 3 seconds. While not reading the data from the transponder, an external reader 3880 (Texas Instruments) provides a continuous RF signal to charge the battery 3820. The CDC 3840 can digitize the capacitance of the glucose sensors, and store the results into the EEPROM of the CDC. The saved data is then read via an I2C bus by the microcontroller 3830, which is then sent the data to the transponder 3810 through a SPI bus. The transponder 3810 modulates the digitized data by using two carry frequencies to represent "1" and "0". In addition, the transponder 3810 can harvest RF power from the external reader and provide a voltage at 3.6 V to the rechargeable battery 3820. All integrated circuit (IC) chips in the wireless interface feature low power consumption and are able to enter from working mode to sleep mode to save the energy when no operation is conducted.

The functioning of this wireless interface was tested as follows. A single-module dielectric affinity glucose sensor, such as described in Example 4, was coupled into the wireless interface 3800. This sensor contains a parallel plate capacitor formed by a perforated electrode and a bottom electrode. The sensor was original exposed in air, and the capacitance measured by the wireless interface was approximately 0.76 pF (FIG. 39). Then, the dielectrics sandwiched between the electrodes was changed from air to water. As a result, the sensor capacitance increased to 0.9 pF, indicating an increase in permittivity of the sensor dielectrics. This result demonstrates that the wireless interface has successfully measured the permittivity-induced capacitance change and can be applied to implantable glucose detection. In addition, the sensor capacitance measured by the interface is very stable in water, suggesting similar sensor stability in polymer solutions.

The foregoing merely illustrates the principles of the disclosed subject matter. Various modifications and alterations to the described embodiments will be apparent to those skilled in the art in view of the inventors' teachings herein. Features of existing methods can be integrated into the methods of the exemplary embodiments of the disclosed subject matter or a similar method. It will thus be appreciated that those skilled in the art will be able to devise numerous methods which, although not explicitly shown or described herein, embody the principles of the disclosed subject matter and are thus within its spirit and scope.

The invention claimed is:

1. An implantable monitor for monitoring a target analyte in interstitial fluid of a subject, comprising a microdevice coupled with a wireless interface;
   wherein the microdevice comprises:
      a semi-permeable membrane structure;
      a substrate; and
      a first microchamber and a second microchamber, each formed between the semi-permeable membrane structure and the substrate, each of the first and second microchambers comprising a suspended element positioned to be spaced apart from the substrate;
   wherein the suspended element in each of the first and second microchambers comprises a perforated top electrode and the substrate comprises a bottom electrode;
   wherein the first microchamber is adapted to receive a solution including a polymer capable of binding the target analyte;
   wherein the second microchamber is adapted to receive a reference solution for screening effects not caused by the target analyte;
   wherein perforations in the top electrode in the first microchamber are configured to allow the solution to fill a gap between the top electrode in the first microchamber and the bottom electrode;
   wherein perforations in the top electrode in the second microchamber are configured to allow the reference solution to fill a gap between the top electrode in the second microchamber and the bottom electrode;
   wherein the semi-permeable membrane structure is permeable to the target analyte and impermeable to the polymer, thereby when the sample is placed in contact with the semi-permeable membrane structure, the target analyte, if present in the sample, permeates the semi-permeable membrane structure and enters the first microchamber and the second microchamber, respectively, and the polymer is prevented from escaping from the first microchamber through the semi-permeable membrane structure.

2. The implantable monitor of claim 1, wherein the target analyte is glucose.

3. The implantable monitor of claim 1, wherein the wireless interface comprises:
   a capacitance digital converter coupled with the microdevice and adapted to produce a digital signal representing a measurement of the target analyte in the interstitial fluid of the subject;
   a microcontroller coupled with the capacitance digital converter; and
   a transponder coupled with the microcontroller to transmit the digital signal received from the capacitance digital converter to an external reader.

4. The implantable monitor of claim 3, wherein the capacitance digital converter is a $\Sigma$-$\Delta$ capacitance digital converter.

5. The implantable monitor of claim 3, wherein the transponder is adapted to modulate the digital signal by using a first carry frequency and a second carry frequency to respectively represent 1 and 0.

* * * * *